(12) United States Patent
Takahashi et al.

(10) Patent No.: US 7,977,327 B2
(45) Date of Patent: Jul. 12, 2011

(54) SUBSTITUTED PYRROLIDINE DERIVATIVE

(75) Inventors: Hisashi Takahashi, Edogawa-ku (JP);
Junichi Kuroyanagi, Edogawa-ku (JP);
Rie Miyauchi, Edogawa-ku (JP);
Masatoshi Nagamochi, Edogawa-ku (JP); Makoto Takemura, Edogawa-ku (JP); Isao Hayakawa, Edogawa-ku (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 11/596,318

(22) PCT Filed: May 13, 2005

(86) PCT No.: PCT/JP2005/008750
§ 371 (c)(1),
(2), (4) Date: Nov. 13, 2006

(87) PCT Pub. No.: WO2005/111015
PCT Pub. Date: Nov. 24, 2005

(65) Prior Publication Data
US 2008/0045520 A1   Feb. 21, 2008

(30) Foreign Application Priority Data
May 13, 2004  (JP) .................. 2004-143352

(51) Int. Cl.
*A61K 31/54* (2006.01)
(52) U.S. Cl. ..................... 514/183; 514/230.2
(58) Field of Classification Search .......... None
See application file for complete search history.

(56) References Cited

U.S. PATENT DOCUMENTS

| | | | |
|---|---|---|---|
| 4,782,180 A * | 11/1988 | Wemple et al. | 562/479 |
| 4,801,584 A | 1/1989 | Yokose et al. | |
| 4,864,023 A | 9/1989 | Yokose et al. | |
| 6,656,952 B2 * | 12/2003 | Takemura et al. | 514/312 |
| 2006/0264428 A1 | 11/2006 | Takahashi et al. | |

FOREIGN PATENT DOCUMENTS

| | | |
|---|---|---|
| EP | 0 208 210 A1 | 1/1987 |
| EP | 1 712 554 A1 | 10/2006 |
| JP | 62 215572 | 9/1987 |
| JP | 63-132891 A | 6/1988 |
| JP | 5 59052 | 3/1993 |
| JP | 5 163244 | 6/1993 |
| JP | 7 300416 | 11/1995 |
| JP | 8 259561 | 10/1996 |
| WO | 98 58923 | 12/1998 |
| WO | WO 03/076428 A1 | 9/2003 |
| WO | WO 03/097634 A1 | 11/2003 |
| WO | WO 2004/058261 A1 | 7/2004 |

OTHER PUBLICATIONS

Kawakami K, Takahashi H, Ohki H, Kimura K, Miyauchi S, Miyauchi R, Takemura M. Studies on 8-methoxyquinolones: synthesis and antibacterial activity of 7-(3-amino-4-substituted)pyrrolidinyl derivatives. Chem Pharm Bull (Tokyo). 48(11):1667-72, 2000.*
Williams et al (Foye's Principles of Medicinal Chemistry, 5th Ed., pp. 59-61, 2002).*
Penning et al (J Med Chem 40:1347-1365, 1997).*
U.S. Appl. No. 12/422,726, filed Apr. 13, 2009, Takahashi, et al.
Katsuhiro Kawakami, et al., "Synthesis and Antibacterial Activity of Novel Pyridobenzoxazine Analogues", Chemical and Pharmaceutical Bulletin, vol. 46, No. 11, 1998, pp. 1710-1715.
Japanese Office Action issued Jan. 5, 2011 in Japanese Patent Application No. 2006-513359 published Apr. 20, 2006.
D. Bouzard, et al., "Fluoronaphthyridines and Quinolones as Antibacterial Agents. 2. Synthesis and Structure-Activity Relationship of New 1-*tert*-Butyl 7-Substituted Derivatives", Journal of Medicinal Chemistry, 1990, vol. 33, No. 5, pp. 1344-1352.
K. W. Lee. et al., "Quantitative structure-activity relationship (QSAR) study by use of theoretical descriptors: quinolone and naphthyridine", Bulletin of the Korean Chemical Society, 1994, vol. 15, No. 12, pp. 1070-7079.

* cited by examiner

*Primary Examiner* — Brandon J Fetterolf
*Assistant Examiner* — Craig Ricci
(74) *Attorney, Agent, or Firm* — Oblon, Spivak, McClelland, Maier & Neustadt, L.L.P.

(57) ABSTRACT

A quinolone antibacterial compound, or a salt or hydrate of the compound, for the treatment of infectious diseases, which exhibit potent antibacterial activity and higher selective toxicity against Gram-positive and Gram-negative bacteria, which do not cause side effects (e.g., convulsion), which exhibit higher safety, and which has a structure of formula (I):

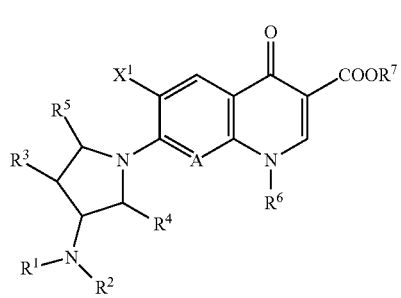

19 Claims, No Drawings

SUBSTITUTED PYRROLIDINE DERIVATIVE

TECHNICAL FIELD

The present invention relates to a synthetic quinolone antibacterial drug which is useful as a drug, an veterinary drug, a fishery drug, or an antibacterial preservative; and more particularly to a synthetic quinolone antibacterial drug containing a 1,4-dihydro-4-oxoquinoline-3-carboxylic acid (hereinafter abbreviated as "quinolone") skeleton having, at position 7, a 3-amino-4-aliphatic-hydrocarbon-group-substituted-pyrrolidin-1-yl group. The term "synthetic quinolone antibacterial drug" encompasses a synthetic quinolone antibacterial drug containing merely a quinolone skeleton, and a synthetic quinolone antibacterial drug containing, as a basic skeleton, a quinolone-based skeleton further having a condensed ring, as in the case of 2,3-dihydro-7-oxo-7H-pyrido[1,2,3-de][1,4]benzoxazine-6-carboxylic acid (hereinafter abbreviated as "pyridobenzoxazine").

BACKGROUND ART

Since the discovery of norfloxacin, synthetic quinolone antibacterial drugs have been improved in their antibacterial activity and pharmacokinetics, and many compounds have been employed in the clinical field as chemotherapeutic agents which are effective for almost all systemic infectious diseases.

However, in recent years, bacteria exhibiting low sensitivity to synthetic quinolone antibacterial drugs have become increasingly common in the clinical field. For example, there has been an increase in Gram-positive bacteria which exhibit resistance to drugs other than synthetic quinolone antibacterial drugs and exhibit low sensitivity to synthetic quinolone antibacterial drugs, including β-lactam-insensitive Gram-positive cocci such as *Staphylococcus aureus* (MRSA) and *Streptococcus neumoniae* (PRSP), and aminoglycoside-antibacterial-drug-insensitive *Enterococcus* (VRE). Therefore, particularly in the clinical field, demand has arisen for a drug exhibiting higher efficacy on Gram-positive cocci.

As has been shown, when administered in combination with nonsteroidal anti-inflammatory drugs (NSAIDs), some synthetic quinolone antibacterial drugs cause side effects, including convulsion, central actions (e.g., mild central nervous disorders such as stagger, headache, and insomnia, and severe side effects such as convulsion), phototoxicity (photosensitivity), hepatotoxicity, cardiotoxicity (fatal-arrhythmia-inducing abnormality which is observed as abnormal electrocardiogram), and abnormal blood glucose level. Therefore, demand has arisen for development of a synthetic quinolone antibacterial drug exhibiting higher safety (see, for example, Non-Patent Document 1).

As has been known, the antibacterial activity, pharmacokinetics, and safety of a synthetic quinolone antibacterial drug are greatly affected by the structure of a substituent which is present at position 7 (or a position corresponding thereto) of the quinolone skeleton. Quinolone derivatives in which the quinolone skeleton is substituted, at position 7, with a 3-amino-4-methylpyrrolidin-1-yl group have been known to exhibit potent antibacterial activity to Gram-negative and Gram-positive bacteria (see, for example, Non-Patent Documents 2 and 3).

However, most of the aforementioned 3-amino-4-methylpyrrolidin-1-yl-group-substituted quinolone derivatives exhibit high incidence of chromosomal aberration, potent cytotoxicity, potent mouse or rat bone marrow micronucleus induction, and low selective toxicity, as compared with the case of quinolone derivatives having, as a substituent, a substituted or non-substituted piperazinyl group. Therefore, such a 3-amino-4-methylpyrrolidin-1-yl-group-substituted quinolone derivative acts on bacteria and as well on eukaryotic cells (see Non-Patent Document 3), and thus is difficult to employ as a drug or a veterinary drug. In practice, such a quinolone derivative has not yet been employed clinically.

Known quinolone derivatives substituted at position 7 with a 3-amino-4-alkylpyrrolidin-1-yl group, which are related to the compound of the present invention, are described below (see Patent Documents 1 and 2).

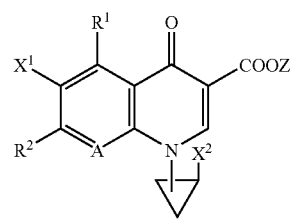

[F1]

The substituents of a compound of this formula are defined in Patent Document 1, etc. Although the substituents may be denoted by symbols that are common to those as used herein, the definitions provided in the prior art should be considered as irrelevant to those of the present invention. Specifically disclosed is merely a compound in which the substituent at position 4 of a pyrrolidinyl group (corresponding to the group $R^2$) is a methyl group.

Patent Documents 3 and 4 disclose a compound having the following structure; specifically, merely a compound in which the substituent at position 4 of a pyrrolidinyl group is a methyl group (the substituents of this compound are defined in Patent Document 3, etc., and thus, even when the substituents are represented by the same symbols as used herein, they are irrelevant to those as defined herein).

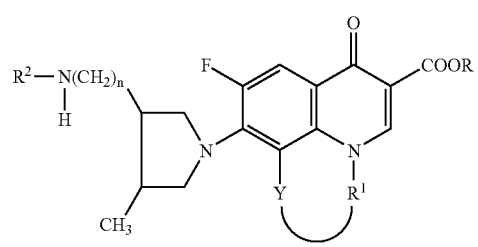

[F2]

Patent Documents 3 and 4 also disclose a compound having the following pyridobenzoxazine skeleton. The compound, in which the substituent at position 7 is a cis-3-amino-4-methylpyrrolidin-1-yl group, is a diastereomeric mixture.

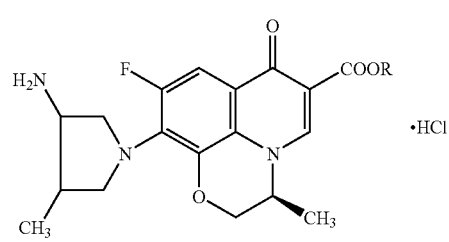

[F3]

Patent Document 5 discloses a compound having the following structure, in which the substituent at position 4 of a pyrrolidinyl group (corresponding to the group R²) is a methyl group, and the substituent at position 1 of the quinolone skeleton (corresponding to the group R¹) is a 2-fluorocyclopropyl group (the substituents of the compound disclosed in Patent Document 5 are defined in Patent Document 5, and thus, even when the substituents are represented by the same symbols as used herein, they are irrelevant to those as defined herein). According to this patent document, the 1-position substituent is preferably a non-substituted cyclopropyl group.

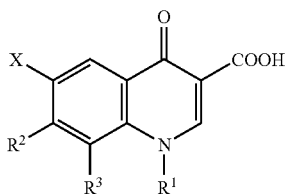

[F4]

Patent Document 6 does not disclose a compound in which the 1-position substituent is a halogenocyclopropyl group.

Patent Document 7 discloses a compound in which the substituent at position 4 of a pyrrolidinyl group is an ethyl group, but does not describe specific examples of the compound. In addition, the substituent at position 1 of the quinolone skeleton is limited to a non-substituted cyclopropyl group.

Patent Documents 8 and 9 disclose a compound in which the substituent at position 4 of a pyrrolidinyl group (corresponding to the group R¹) is an ethyl group (the substituents of the compound disclosed in Patent Documents 8 and 9 are defined in Patent Document 8, etc., and thus, even when the substituents are represented by the same symbols as used herein, they are irrelevant to those as defined herein). However, the substituent at position 1 of the quinolone skeleton is a non-substituted cyclopropyl group.

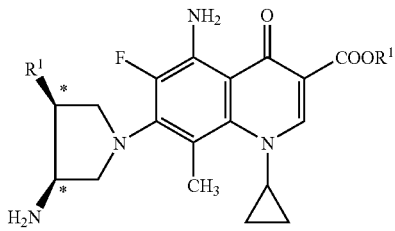

[F5]

Patent Documents 10 and 11 disclose a compound having the following structure.

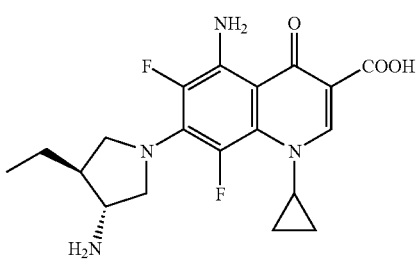

[F6]

Patent Document 1: Specification of JP Patent No. 2917010
Patent Document 2: Specification of U.S. Pat. No. 5,587,386
Patent Document 3: Specification of European Patent No. 208210
Patent Document 4: Specification of U.S. Pat. No. 4,753,953
Patent Document 5: JP-A-SHO63-264461
Patent Document 6: U.S. Pat. No. 4,855,292
Patent Document 7: JP-A-SHO64-83068
Patent Document 8: WO 96/22988 pamphlet
Patent Document 9: JP-A-HEI8-259561
Patent Document 10: Specification of European Patent No. 242789
Patent Document 11: Specification of U.S. Pat. No. 4,886,810
Non-Patent Document 1: Clinical Application of New Quinolone Agent, edited by Hiroyuki Kobayashi, Iyaku Journal Co., Ltd. (2001)
Non-Patent Document 2: International Journal of Antimicrobial Agents, Vol. 16, p. 5 (2000)
Non-Patent Document 3: Journal of Antimicrobial Chemotherapy, Vol. 33, p. 685 (1994)

DISCLOSURE OF THE INVENTION

Problems to be Solved by the Invention

Therefore, the present invention contemplates provision of a quinolone antibacterial agent and a drug for the treatment of infectious diseases (hereinafter may be referred to as an "infectious disease treating drug"), which exhibit potent antibacterial activity and higher selective toxicity against Gram-positive and Gram-negative bacteria, which do not cause side effects (e.g., convulsion), and which exhibit higher safety.

Means for Solving the Problems

In view of the foregoing, the present inventors have conducted extensive studies, and as a result, have found that a compound represented by the following formula (I), a salt of the compound, or a hydrate of the compound or the salt exhibits antibacterial activity against Gram-positive and Gram-negative bacteria at a level almost comparable to that of a known synthetic quinolone antibacterial drug, and exhibits such a higher safety that it can be employed as an antibacterial drug or an infectious disease treating drug. The present invention has been accomplished on the basis of these findings.

Accordingly, the present invention provides a compound represented by the following formula (I):

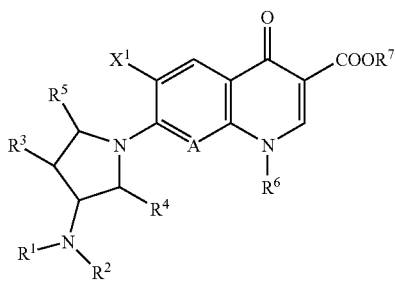

[F7]

I

[wherein R¹ represents a hydrogen atom, a C1-C6 alkyl group, or a substituted carbonyl group derived from an amino acid, a dipeptide, or a tripeptide;
R² represents a hydrogen atom or a C1-C6 alkyl group, and, when either one or each of R¹ and R² is an alkyl group, the alkyl group may be substituted with a group selected from the group consisting of a hydroxyl group, an amino group, a halogen atom, a C1-C6 alkylthio group, and a C1-C6 alkoxy group;

$R^3$ represents a C2-C6 alkyl group, a C2-C6 alkenyl group, or a C3-C6 cycloalkyl group;

$R^4$ and $R^5$ each independently represents a hydrogen atom or a C1-C6 alkyl group;

$R^6$ represents a C3-C6 halogenocycloalkyl group;

$R^7$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, a C1-C6 alkyl group, a C2-C7 alkoxymethyl group, or a phenylalkyl group formed of a C1-C6 alkylene group and a phenyl group;

$X^1$ represents a hydrogen atom or a halogen atom; and

A represents a nitrogen atom or a partial structure represented by the following formula (II):

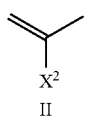

[F8]

II (wherein $X^2$ represents a C1-C6 alkyl group or a C1-C6 alkoxy group; $X^2$ and the aforementioned $R^6$ may together form a cyclic structure so as to contain a part of the quinolone nucleus; the thus-formed ring may contain, as a ring-constituting atom, an oxygen atom, a nitrogen atom, or a sulfur atom; and the ring may be substituted with a C1-C6 alkyl group which may have a substituent)];

a salt, or a hydrate thereof.

The present invention also provides 7-[(3S,4S)-3-amino-4-ethylpyrrolidin-1-yl]-6-fluoro-1-[(1R,2S)-2-(S) -fluorocyclopropyl]-1,4-dihydro-8-methoxy-4-oxoquinoline-3-carboxylic acid, a salt, or a hydrate thereof; 7-[(3S,4S)-3-amino-4-ethylpyrrolidin-1-yl]-6-fluoro-1-[(1R,2S)-2-fluorocyclopropyl]-1,4-dihydro-8-methyl-4-oxoquinoline-3-carboxylic acid, a salt, or a hydrate thereof; and (3S)-10-[(3S,4S)-3-amino-4-ethylpyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof.

The present invention also provides a drug, an antibacterial drug, and an infectious disease treating drug, each of the drugs containing, as an active ingredient, a compound represented by formula (I), a salt, or a hydrate thereof.

The present invention also provides a method for treating a pathological condition, characterized by comprising administration of an effective amount of a compound represented by formula (I), a salt, or a hydrate thereof; and a method for treating an infectious disease, characterized by comprising administration of an effective amount of a compound represented by formula (I), a salt, or a hydrate thereof.

The present invention also provides a method for producing a drug, characterized by comprising incorporation of a compound represented by formula (I), a salt, or a hydrate thereof; a method for producing an antibacterial drug, characterized by comprising incorporation of a compound represented by formula (I), a salt, or a hydrate thereof; and a method for producing an infectious disease treatment drug, characterized by comprising incorporation of a compound represented by formula (I), a salt, or a hydrate thereof.

The present invention also provides use of a compound represented by formula (I), a salt, or a hydrate thereof for producing a drug; use of a compound represented by formula (I), a salt, or a hydrate thereof for producing an antibacterial drug; and use of a compound represented by formula (I), a salt, or a hydrate thereof for producing an infectious disease treating drug.

EFFECTS OF THE INVENTION

The substituted pyrrolidine derivative of the present invention exhibits low convulsion-inducing effect and chromosomal-aberration-inducing effect, and higher safety, although the antibacterial activity of the derivative against Gram-positive and Gram-negative bacteria is almost comparable to that of a known synthetic quinolone antibacterial drug. Therefore, the substituted pyrrolidine derivative of the present invention is useful as an antibacterial drug or an infectious disease treatment drug.

BEST MODE FOR CARRYING OUT THE INVENTION

Now will be described the substituents of a compound of the present invention represented by formula (I).

$R^1$ represents a hydrogen atom, a C1-C6 alkyl group, or a substituted carbonyl group derived from an amino acid, a dipeptide, or a tripeptide. $R^2$ represents a hydrogen atom or a C1-C6 alkyl group. Examples of the C1-C6 alkyl group represented by $R^1$ or $R^2$ include linear alkyl groups such as methyl, ethyl, n-propyl, n-butyl, and n-pentyl; and branched alkyl groups such as isopropyl, isobutyl, sec-butyl, and tert-butyl. Preferably, each of $R^1$ and $R^2$ is a hydrogen atom; or one of $R^1$ and $R^2$ is a hydrogen atom, and the other is a C1-C6 alkyl group. Particularly preferably, each of $R^1$ and $R^2$ is a hydrogen atom; or one of $R^1$ and $R^2$ is a hydrogen atom, and the other is a methyl group.

A compound of formula (I) in which $R^1$ is a substituted carbonyl group derived from an amino acid, a dipeptide, or a tripeptide is useful as a prodrug. Examples of substituents employed for producing such a prodrug include a substituted carbonyl group derived from an amino acid (e.g., glycine, alanine, or aspartic acid), a dipeptide (e.g., glycine-glycine, glycine-alanine, or alanine-alanine), or a tripeptide (e.g., glycine-glycine-alanine or glycine-alanine-alanine).

When either one or each of $R^1$ and $R^2$ is an alkyl group, the alkyl group may be substituted with a group selected from the group consisting of a hydroxyl group, an amino group, a halogen atom, a C1-C6 alkylthio group, and a C1-C6 alkoxy group. When the alkyl group is substituted with a hydroxyl group or an amino group, more preferably, such a substituent is present on the terminal carbon atom of the alkyl group. Preferred hydroxyl-group-containing alkyl groups include hydroxyalkyl groups having three or less carbon atoms, such as a hydroxymethyl group, a 2-hydroxyethyl group, a 2-hydroxypropyl group, and a 3-hydroxypropyl group. Preferred amino-group-containing alkyl groups include aminoalkyl groups having three or less carbon atoms, such as an aminomethyl group, a 2-aminoethyl group, a 2-aminopropyl group, and a 3-aminopropyl group.

When the alkyl group is substituted with a halogen atom, the alkyl group may be any of C1-C6 linear and branched alkyl groups, and the halogen atom is preferably a fluorine atom. No particular limitation is imposed on the number of fluorine atom(s), and such a fluoroalkyl group may be a monofluoroalkyl group to a perfluoroalkyl group. Examples of the fluorine-substituted alkyl group include a monofluoromethyl group, a difluoromethyl group, a trifluoromethyl group, and a 2,2,2-trifluoroethyl group.

When the alkyl group is substituted with an alkylthio group or an alkoxy group, the alkyl group may be a linear or branched alkyl group, and the alkyl group constituting the alkylthio or alkoxy group may be a linear or branched alkyl group. The alkylthio-group-containing alkyl group is preferably an alkylthiomethyl group, an alkylthioethyl group, or an alkylthiopropyl group, and the alkylthio group is preferably a C1-C3 alkylthio group. More preferred alkylthio-group-containing alkyl groups include a methylthiomethyl group, an ethylthiomethyl group, and a methylthioethyl group. The alkoxy-group-containing alkyl group is preferably an alkoxymethyl group, an alkoxyethyl group, or an alkoxypropyl group, and the alkoxy group is preferably a C1-C3 alkoxy group. More preferred alkoxy-group-containing alkyl groups include a methoxymethyl group, an ethoxymethyl group, and a methoxyethyl group.

Examples of the C2-C6 alkyl group represented by $R^3$ include linear alkyl groups such as ethyl, n-propyl, n-butyl, and n-pentyl; and branched alkyl groups such as isopropyl, isobutyl, sec-butyl, and tert-butyl. An ethyl group, an n-propyl group, or an isopropyl group is preferred, with an ethyl group being particularly preferred. Examples of the C3-C6 cycloalkyl group include a cyclopropyl group, a cyclobutyl group, a cyclopentyl group, and a cyclohexyl group. A cyclopropyl group or a cyclobutyl group is preferred, with a cyclopropyl group being particularly preferred. Examples of the C2-C6 alkenyl group include a vinyl group, a 1-propenyl group, a 2-propenyl group, and an isopropenyl group. A vinyl group or an isopropenyl group is preferred, with a vinyl group being particularly preferred. Of these substituents represented by $R^3$, an ethyl group is particularly preferred.

$R^4$ and $R^5$ each independently represents a hydrogen atom or a C1-C6 alkyl group. Preferably, each of $R^4$ and $R^5$ is a hydrogen atom. The C1-C6 alkyl group may be a C1-C6 alkyl group similar to that described above.

A C3-C6 halogenocycloalkyl group, which is represented by $R^6$, refers to any of the aforementioned cycloalkyl groups substituted with one or two halogen atoms (e.g., fluorine, chlorine, and bromine). Such a cycloalkyl group is preferably a monohalogenocyclopropyl group or a dihalogenocyclopropyl group, particularly preferably a monofluorocyclopropyl group.

Examples of the substituent represented by $R^7$ include a hydrogen atom, a phenyl group, an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, any of the aforementioned C1-C6 alkyl groups, a C2-C7 alkoxymethyl group, and a phenylalkyl group formed of a C1-C6 alkylene group and a phenyl group. A C2-C7 alkoxymethyl group refers to a methyl group substituted with any of the aforementioned C1-C6 alkoxy groups. Specific examples of the C2-C7 alkoxymethyl group include a methoxymethyl group, an ethoxymethyl group, and a propoxymethyl group. Specific examples of the phenylalkyl group formed of a C1-C6 alkylene group and a phenyl group include a phenylmethyl group and a phenethyl group. Of these substituents represented by $R^7$, a hydrogen atom is particularly preferred.

A quinolone carboxylic acid derivative in which the carboxylic moiety is esterified is useful as a synthetic intermediate or a prodrug. Examples of the ester useful as a synthetic intermediate include an alkyl ester, a benzyl ester, an alkoxyalkyl ester, a phenylalkyl ester, and a phenyl ester. Examples of the ester useful as a prodrug (i.e., an ester which is readily cleaved in vivo to form a free carboxylic acid) include an acetoxymethyl ester, a pivaloyloxymethyl ester, an ethoxycarbonyl ester, a choline ester, a dimethylaminoethyl ester, a 5-indanyl ester, a phthalidinyl ester, a 5-alkyl-2-oxo-1,3-dioxol-4-ylmethyl ester, and a 3-acetoxy-2-oxobutyl ester.

$X^1$ represents a hydrogen atom or a halogen atom. A hydrogen atom or a fluorine atom is preferred, with a fluorine atom being particularly preferred.

In the partial structure represented by A, $X^2$ represents a C1-C6 alkyl group or a C1-C6 alkoxy group. The C1-C6 alkyl group may be any of the aforementioned C1-C6 alkyl groups. The C1-C6 alkoxy group may be an alkoxy group derived from the C1-C6 alkyl group. Of these substituents, a C1-C3 alkyl group or a C1-C3 alkoxy group is preferred, with a methyl group or a methoxy group being particularly preferred. The partial structure may be a cyclic structure which is formed by $X^2$ and $R^6$ so as to contain a part of the quinolone nucleus. The thus-formed ring is preferably a 5- to 7-membered ring, particularly preferably a 6-membered ring. The thus-formed ring may be saturated or unsaturated. The cyclic structure may contain, as a ring-constituting atom, an oxygen atom, a nitrogen atom, or a sulfur atom, and may be substituted with any of the aforementioned C1-C6 alkyl groups. Preferably, the thus-formed cyclic structure contains an oxygen atom, and is substituted with a methyl group. The partial structure which forms the cyclic structure is preferably a structure represented by the formula: —O—CH$_2$—CH(—CH$_3$)— (the carbon atom on the extreme right is bonded to the nitrogen atom of the quinolone skeleton).

The compound (I) of the present invention having such a partial structure preferably has, as a basic skeleton, a pyridobenzoxazine skeleton represented by the following formula (A):

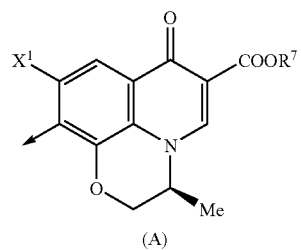

(A)

[F9]

[In formula A, the arrow denotes a bond to be connected with the aforementioned pyrrolidine ring, and $X^1$ and $R^7$ have the same meanings as defined above.]

In the compound of the present invention represented by formula (I), the substituent at position 7 (or the substituent at position 10 in the case where the compound has a pyridobenzoxazine skeleton); i.e., a 3-amino-4-aliphatic-group-substituted-pyrrolidin-1-yl group is represented by the following formula (B).

[F10]

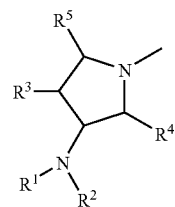

(B)

Therefore, the compound has four optical isomers based on the asymmetric carbons at positions 3 and 4 of this substituent. Of these optical isomers, 3,4-cis isomers are preferred, and a (3S,4S)-configuration or (3S,4R)-configuration isomer is more preferred, with a (3S,4S)-configuration isomer represented by the following formula (B1) being particularly preferred.

[F11]

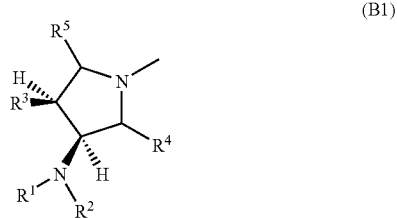

(B1)

[In formulas (B) and (B1), $R^1$, $R^2$, $R^3$, $R^4$ and $R^5$ have the same meanings as defined above.]

The stereochemistry of the halogenocyclopropyl group represented by $R^6$ is preferably such that the halogen atom and the quinolone carboxylic acid skeleton are in a 1,2-cis configuration with respect to the cyclopropane ring. As used herein, the term "cis configuration" refers to the case where the halogen atom and the quinolone carboxylic acid skeleton are in a cis configuration with respect to the cyclopropane ring. The cis configuration may be a (1R,2S)-configuration or a (1S,2R)-configuration, but the former is preferred.

When the compound of the present invention represented by formula (I), which has such a structure that produces diastereomers, is to be administered to an animal or a human, preferably, a compound containing a single diastereomer is selected for administration. The expression "a compound containing a single diastereomer" refers to the case where the compound does not contain an additional diastereomer at all, and as well the case where the compound contains an additional diastereomer to such an extent that the additional diastereomer does not affect the physical constant and activity of the compound. As used herein, the expression "stereochemically single" refers to the case where, when a compound has optical isomers, the compound is formed of a single optical isomer, or the compound contains an additional optical isomer to such an extent that the additional optical isomer does not affect the physical constant and activity of the compound. The compound (I) of the present invention is preferably a compound in which the substituents at positions 3 and 4 of the 7-position substituent are in a (3S,4S)-configuration, and the halogen atom and the quinolone carboxylic acid skeleton are in a (1R,2S)-configuration or a (3S,4S)-configuration with respect to the cyclopropane ring of the halogenocyclopropyl group represented by $R^6$. In view that the aforementioned pyridobenzoxazine skeleton contains a quinolone skeleton, a compound having the pyridobenzoxazine skeleton is particularly preferred.

The compound (I) of the present invention may be in a free form, or may be in the form of an acid addition salt or a carboxylic salt. Examples of the acid addition salt include inorganic acid salts such as hydrochloride, sulfate, nitrate, hydrobromide, hydroiodide, and phosphate; and organic acid salts such as sulfonates (e.g., methanesulfonate, benzenesulfonate, and p-toluenesulfonate) and carboxylates (e.g., acetate, citrate, maleate, fumarate, and lactate). Examples of the carboxylic salt include alkali metal salts such as lithium salt, sodium salt, and potassium salt; alkaline earth metal salts such as magnesium salt and calcium salt; ammonium salt; triethylamine salt; N-methylglucamine salt; and tris-(hydroxymethyl)aminomethane salt. The free form, acid addition salt, or carboxylic salt of the compound (I) of the present invention may be present in the form of a hydrate.

Specific examples of the compound (I) of the present invention include:

7-[(3S,4S)-3-amino-4-ethylpyrrolidin-1-yl]-6-fluoro-1-[(1R,2S)-2-(S)-fluorocyclopropyl]-1,4-dihydro-8-methoxy-4-oxoquinoline-3-carboxylic acid, a salt, or a hydrate thereof (Compound No. 1);

7-[(3S,4S)-3-amino-4-ethylpyrrolidin-1-yl]-6-fluoro-1-[(1R,2S)-2-fluorocyclopropyl]-1,4-dihydro-8-methyl-4-oxoquinoline-3-carboxylic acid, a salt, or a hydrate thereof (Compound No. 2);

(3S)-10-[(3S,4S)-3-amino-4-ethylpyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof (Compound No. 3);

7-[(3S,4S)-3-amino-4-propylpyrrolidin-1-yl]-6-fluoro-1-[(1R,2S)-2-fluorocyclopropyl]-8-methoxy-1,4-dihydro-4-oxoquinoline-3-carboxylic acid, a salt, or a hydrate thereof (Compound No. 4);

7-[(3S,4S)-3-amino-4-propylpyrrolidin-1-yl]-6-fluoro-1-[(1R,2S)-2-fluorocyclopropyl]-8-methyl-1,4-dihydro-4-oxoquinoline-3-carboxylic acid, a salt, or a hydrate thereof (Compound No. 5);

(3S)-10-[(3S,4S)-3-amino-4-propylpyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof (Compound No. 6);

(3S)-10-[(3S,4S)-3-amino-4-vinyl-1-pyrrolidinyl]-9-fluoro-2,3-dihydro-3-methyl-7-oxo-7H-pyrido[1,2,3-de][1,4]benzoxazine-6-carboxylic acid, a salt, or a hydrate thereof (Compound No. 7);

7-[(3S,4S)-3-amino-4-cyclopropylpyrrolidin-1-yl]-6-fluoro-1-[(1R,2S)-2-fluorocyclopropyl]-8-methoxy-1,4-dihydro-4-oxoquinoline-3-carboxylic acid, a salt, or a hydrate thereof (Compound No. 8);

(3S)-10-[(3S,4S)-3-amino-4-cyclopropylpyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof (Compound No. 9);

(3S)-10-[(3S)-3-amino-4-isopropyl-1-pyrrolidinyl]-9-fluoro-2,3-dihydro-3-methyl-7-oxo-7H-pyrido[1,2,3-de][1,4]benzoxazine-6-carboxylic acid, a salt, or a hydrate thereof (Compound No. 10);

(3S)-10-[(3S,4R)-3-amino-4-ethylpyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof (Compound No. 11);

7-[(3S,4S)-3-ethyl-4-methylaminopyrrolidin-1-yl]-6-fluoro-1-[(1R,2S)-2-fluorocyclopropyl]-8-methoxy-1,4-dihydro-4-oxoquinoline-3-carboxylic acid, a salt, or a hydrate thereof (Compound No. 12);

(3S)-10-[(3S,4S)-3-ethyl-4-methylaminopyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof (Compound No. 13);

7-[(3S,4S)-3-amino-4-ethylpyrrolidin-1-yl]-1-[(1R,2S)-2-fluorocyclopropyl]-8-methyl-1,4-dihydro-4-oxoquinoline-3-carboxylic acid, a salt, or a hydrate thereof (Compound No. 14);

7-[(3S,4S)-3-ethyl-4-methylaminopyrrolidin-1-yl]-6-fluoro-1-[(1R,2S)-2-fluorocyclopropyl]-8-methyl-1,4-dihydro-4-oxoquinoline-3-carboxylic acid, a salt, or a hydrate thereof (Compound No. 15);

7-[(3S,4S)-3-amino-4-isopropylpyrrolidin-1-yl]-6-fluoro-1-[(1R,2S)-2-fluorocyclopropyl]-8-methyl-1,4-dihydro-4-oxoquinoline-3-carboxylic acid, a salt, or a hydrate thereof (Compound No. 16); and 6-fluoro-1-[(1R,2S)-2-fluorocyclopropyl]-7-[(3S,4S)-3-isopropyl-4-methylaminopyrrolidin-1-yl]-8-methyl-1,4-dihydro-4-oxoquinoline-3-carboxylic acid, a salt, or a hydrate thereof (Compound No. 17).

Of these, particularly preferred are 7-[(3S,4R)-3-amino-4-ethylpyrrolidin-1-yl]-6-fluoro-1-[(1R,2S)-2-(S)-fluorocyclopropyl]-1,4-dihydro-8-methoxy-4-oxoquinoline-3-carboxylic acid, a salt, or a hydrate thereof (Compound No. 1); 7-[(3S,4R)-3-amino-4-ethylpyrrolidin-1-yl]-6-fluoro-1-[(1R,2S)-2-fluorocyclopropyl]-1,4-dihydro-8-methyl-4-oxoquinoline-3-carboxylic acid, a salt, or a hydrate thereof (Compound No. 2); or (3S)-10-[(3S,4R)-3-amino-4-ethylpyrrolidin-1-yl]-9-fluoro-2,3-dihydro-3-methyl-7-oxo-7H-pyrido[1,2,3-de][1,4]benzoxazine-6-carboxylic acid, a salt, or a hydrate thereof (Compound No. 3).

The compound of the present invention represented by formula (I) can be produced through a variety of methods. In a preferred production method, the compound is produced, for example, by reacting a compound represented by the following formula (VI-1) or (VI-2):

[F12]

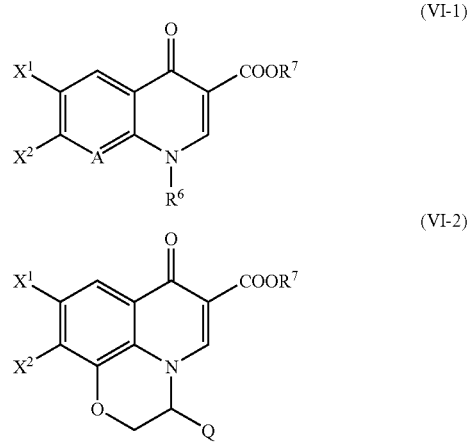

[wherein $R^6$, $R^7$, $X^1$ and A have the same meanings as defined above; $X^2$ represents a leaving group; and Q represents a C1-C6 alkyl group]

or a boron chelate obtained through conversion of the —COOR$^7$ moiety of this compound into —COOBF$_2$, —COOB(OAc)$_2$, or the like with a 3-amino-4-aliphatic-substituted-pyrrolidine derivative represented by the following formula (VII):

[F13]

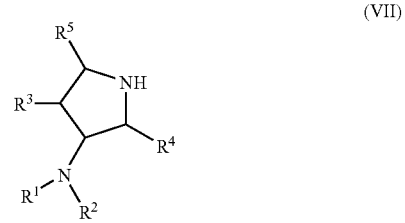

[$R^1$, $R^2$, $R^3$, $R^4$ and $R^5$ have the same meanings as defined above]

or an addition salt of the derivative. A compound represented by formula (VII) may be prepared upon use; i.e., the compound (VII) may be prepared, from a compound in which the nitrogen on the ring is protected, by removing the protective group during the course of reaction. Examples of the leaving group $X^2$ include substituted sulfonyloxy groups such as methanesulfonyloxy, trifluoromethanesulfonyloxy, benzenesulfonyloxy, and toluenesulfonyloxy; and halogen atoms. The addition salt may be any of the aforementioned addition salts. The production method is described in detail in, for example, WO 02/40478 pamphlet or specification of Japanese Patent Application No. 2003-336864. When a boron chelate is employed for reaction, the boron chelate may be produced through a known method. Reaction between a boron chelate and a compound of formula (VII) may be carried out in the presence of a base. After completion of reaction, the boron chelate moiety may be cleaved through hydrolysis in the presence of a base. Specifically, these steps may be performed through a known method.

Next will be described typical methods for producing 3-amino-4-aliphatic-substituted-pyrrolidine derivatives (in particular, (3S,4S)-3-amino-4-aliphatic-substituted-pyrrolidine derivatives). However, the pyrrolidine derivative production method is not limited to the below-described methods.

[F14]

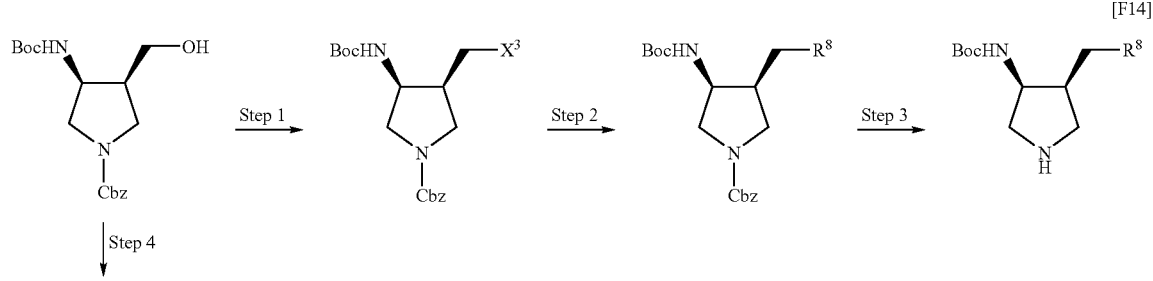

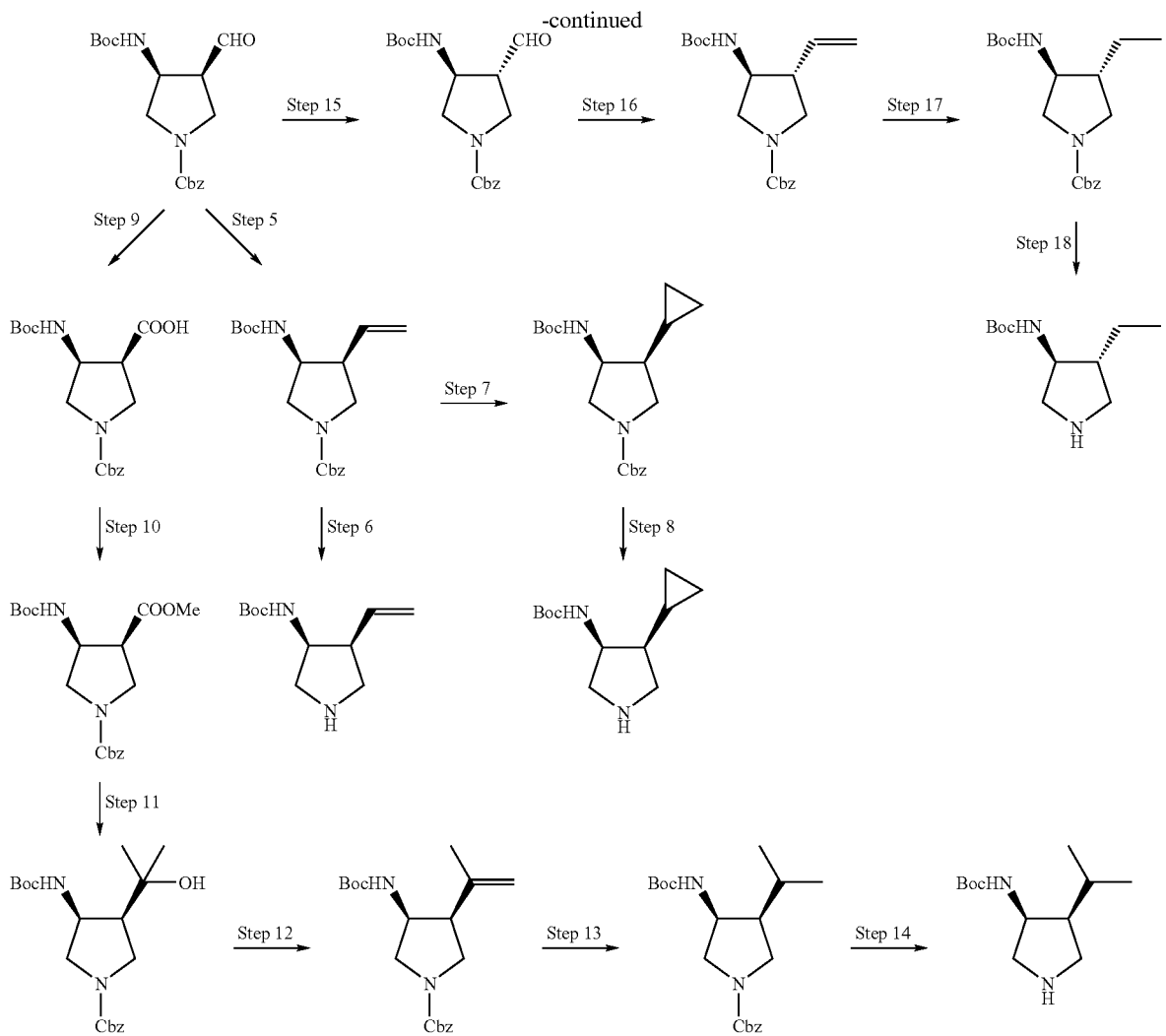

-continued

[In the reaction scheme, "Boc" denotes a tert-butoxycarbonyl group; "Cbz" denotes a benzyloxycarbonyl group; $X^3$ represents a leaving group for nucleophilic substitution; and $R^8$ has the same meaning as defined above in $R^3$.]

In step 1, a leaving group for nucleophilic substitution (step 2) is introduced into the hydroxymethyl moiety of (3S,4S)-1-benzyloxycarbonyl-3-(tert-butoxycarbonyl)amino-hydroxymethylpyrrolidine. (3S,4S)-1-benzyloxycarbonyl-3-(tert-butoxycarbonyl)amino-hydroxymethylpyrrolidine can be produced through the method described in WO 99/65918 pamphlet. Examples of the leaving group include substituted sulfonyloxy groups. A methanesulfonyloxy group, a trifluoromethanesulfonyloxy group, a benzenesulfonyloxy group, or a p-toluenesulfonyloxy group is preferred, with a p-toluenesulfonyloxy group being particularly preferred. The leaving group may be a halogen atom. The halogen atom is preferably a bromine atom or an iodine atom. Introduction of a substituted sulfonyloxy group or halogenation can be performed under generally employed conditions.

In step 2, a carbon-carbon bond is formed through nucleophilic substitution. Examples of the reaction reagent to be employed include organic alkyllithium reagents, which are generally employed for coupling reaction with an alkyl halide; Grignard reagents; and organocopper reagents employed for $S_N2$ substitution, such as Gilman reagents (e.g., dialkyl copper lithium-lithium halide and dialkyl copper lithium-Lewis acid complex). Of these, methyllithium is preferred. Generally, the reaction can be performed by use of a solvent which is inert to organic metal (e.g., an ether solvent such as diethyl ether or tetrahydrofuran). The reagent to be employed may be a commercially available one, or may be prepared upon use or in the reaction system.

In step 3, no particular limitation is imposed on the deprotection at position 1 of the pyrrolidine ring, so long as the deprotection is carried out under such conditions that the other functional groups and the configuration are not changed. In the case where, for example, the 1-position protective group is a benzyloxycarbonyl group, generally, catalytic reduction is performed by use of a palladium catalyst. In this case, ammonium formate or the like may be employed as a hydrogen source in place of hydrogen gas. Alternatively, the deprotection may be performed through, for example, a method employing an organosilane (e.g., triethylsilane), a method employing a strong acid (e.g., hydrobromic acid-acetic acid, trifluoroacetic acid, or trifluoromethanesulfonic acid-trifluoroacetic acid), or a method employing sodium-liquid ammonia (Birch reduction conditions). Preferably, a palladium catalyst is employed in a hydrogen atmosphere.

In step 4, no particular limitation is imposed on the oxidation of the hydroxymethyl group, so long as the oxidation is performed under generally employed conditions. Examples of the oxidizing reagent to be employed include Dess-Martin reagents, dimethyl sulfoxide (including Swern oxidation), ruthenium reagents such as tetrapropylammonium perruthenate (TPAP)/4-methylmorpholine N-oxide (NMO), and chromium oxide reagents such as pyridinium chlorochromate (PCC) and Collins reagent. Oxidation or post-reaction treatment is preferably performed under such conditions that isomerization of the formyl group at position 4 of the pyrrolidine ring [i.e., isomerization from a (4S)-form to a (4R)-form] does not occur. When such isomerization occurs, an undesireble enantiomer [i.e., (4R)-form] can be separated through chromatography or a similar technique. Among the aforementioned oxidation conditions, oxidation employing a Dess-Martin reagent is preferred. Preferably, the resultant product is employed in the subsequent step without being purified.

In step 5, the carbonyl group of the aldehyde moiety is subjected to methylenation. The methylenation generally employs Wittig reaction. Preferably, the methylenation is performed under such conditions that the aforementioned isomerization does not occur. The methylenation may be performed through a method employing an organotitanium reagent such as Tebbe reagent, Grubbs reagent, or Nozaki-Rombert reagent. Preferably, diiodomethane is employed.

In step 6, the protective group at position 1 of the pyrrolidine ring must be removed with retention of the carbon-carbon double bond of the vinyl or vinylidene group at position 4 of the pyrrolidine ring. Such deprotection is performed through, for example, a method employing a strong acid as described above in step 3, or a method employing barium hydroxide. Preferably, the deprotection is performed through a method employing sodium-liquid ammonia.

In step 7, a carbene (or carbenoid) is added to the carbon-carbon double bond to form a cyclopropane ring. Examples of the reagent to be employed for this reaction include a diiodomethane/zinc-copper complex, diiodomethane/diethylzinc, diiodomethane/samarium iodide, a dibromomethane/nickel complex, and a diazomethane/transition metal complex such as a diazomethane/palladium complex. Preferably, a diazomethane/palladium acetate complex is employed.

Step 8 can be performed under conditions similar to those of step 3. Step 8 is performed under such conditions that the cyclopropane ring does not undergo cleavage or rearrangement through catalytic reduction (catalytic hydrolysis) employing a transition metal catalyst.

In step 9, oxidation of the aldehyde moiety can be performed by use of an oxidizing agent such as lead tetraacetate, a permanganate (e.g., potassium permanganate), sodium periodate (with use of a ruthenium catalyst), chromic acid, silver oxide, sodium hypochlorite-sodium dihydrogenphosphate, or hydrogen peroxide. Of these oxidizing agents, sodium hypochlorite-sodium dihydrogenphosphate is preferred.

In step 10, esterification of the carboxylic moiety is performed through, for example, a method in which an alcohol is caused to act on the carboxylic moiety in the presence of an acid catalyst such as sulfuric acid, p-toluenesulfonic acid, or fluoroboric acid, an esterification method employing a dehydrating agent (a method in which reaction proceeds via an active ester, or a method for activating an alcohol), an O-alkylation method employing diazomethane or a similar reagent, a method employing an alkene or an alkyne in the presence of an acid catalyst, an alkylation method in which reaction proceeds via a carboxylic salt, or a method in which reaction proceeds via an acid anhydride or an acid halide. Of these methods, a method employing diazomethane is preferred.

In step 11, an organometallic reagent is added to the ester, to thereby convert the ester into a tertiary alcohol. Examples of the reagent to be employed for this reaction include a Grignard reagent, an organolithium reagent, an organocerium reagent, an organotitanium reagent, an organozinc reagent, an organoaluminum reagent, an organocopper reagent, and an organosamarium reagent. The reaction is generally performed by use of a solvent which is inert to organic metal (e.g., an ether solvent such as diethyl ether or tetrahydrofuran). Of these organometallic reagents, a Grignard reagent, an organolithium reagent, or an organocerium reagent is preferred, with a Grignard reagent being more preferred. In order to prevent the aforementioned isomerization, preferably, the reaction is performed at a temperature of −30 to 0° C.

In step 12, the tertiary alcohol derivative is converted into an alkene through dehydration. The reaction may be generally employed dehydration (elimination) reaction. Examples of the reaction include dehydration employing an acid catalyst such as sulfuric acid or p-toluenesulfonic acid, dehydration employing alumina or the like as a catalyst, dehydration employing a sulfonating agent or an esterifying agent (e.g., thionyl chloride-pyridine), and 1,2-elimination of an ester or a sulfonic ester (e.g., causing a base to act on a substituted sulfonyloxy group). Preferably, methanesulfonyl chloride is employed.

In step 13, the carbon-carbon double bond of the vinylidene group is converted into an isopropyl group through catalytic reduction. Reduction of the carbon-carbon double bond may be performed simultaneously with deprotection at position 1 of the pyrrolidine ring. In addition to catalytic reduction employing a palladium catalyst, there may be performed catalytic hydrogenation employing ammonium formate or the like in place of hydrogen gas. So long as the other functional groups are not affected, there may be performed, for example, reduction employing an organometallic salt/metal hydride reagent (e.g., cobalt chloride/sodium hydride) or hydroboration-protonation. Preferably, a palladium-carbon catalyst is employed in a hydrogen atmosphere.

Step 14 is performed in a manner similar to that of step 3.

In step 15, the absolute configuration of the formyl group at position 4 of the pyrrolidine ring is converted from a (4S)-form to a (4R)-form. This isomerization can be performed in an appropriate solvent by use of an organic base (e.g., triethylamine or 1,8-diazabicyclo[5.4.0]undec-7-ene (DBU)) or an inorganic base (e.g., potassium carbonate or sodium hydroxide). Preferably, triethylamine is employed. The reaction is preferably performed at a temperature of −78 to 40° C. In the case where isomerization conversion is less than 100%, a necessary enantiomer [i.e., (4R)-form] can be separated and purified through chromatography or a similar technique.

Step 16 may be performed in a manner similar to that of step 5, but preferably, methyltriphenylphosphonium bromide is employed. Step 17 is performed in a manner similar to that of step 13, and step 18 is performed in a manner similar to that of step 3. Steps 16 to 18 may be performed simultaneously.

The compound (I) of the present invention can be produced from a compound represented by formula (VI-1) or (VI-2) and a compound represented by formula (VII) through, for example, a method described below. Now will be described the production method by taking, as an example, production of Compound No. 1 described below in the Examples section.

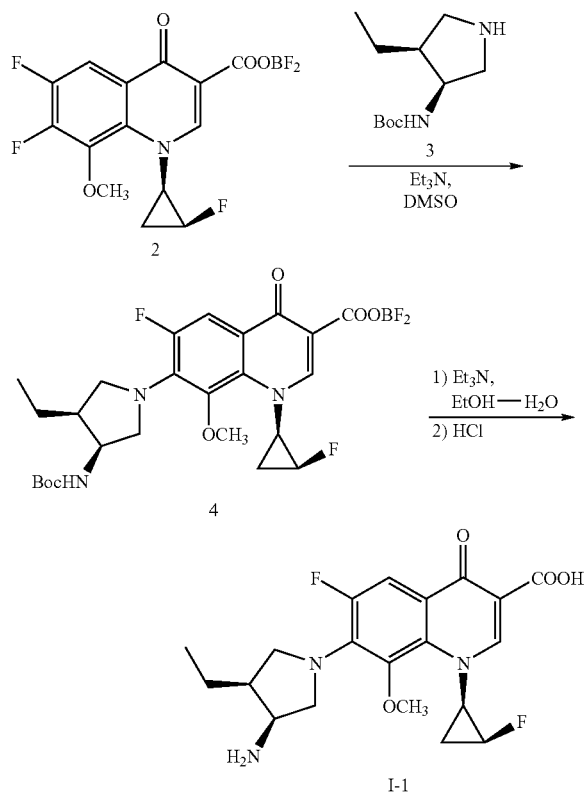

[F15]

Compound (4) can be produced by dissolving compound (2) in an appropriate solvent, and then reacting compound (2) with 3-(tert-butoxycarbonyl)amino-4-aliphatic-substituted-pyrrolidine (3) in the presence of a base. Examples of the protective group which may be employed include, in addition to a tert-butyloxycarbonyl (Boc) group, a benzyloxycarbonyl group, a p-methoxybenzyloxycarbonyl group, an acetyl group, a methoxyacetyl group, a trifluoroacetyl group, a pivaloyl group, a formyl group, a benzoyl group, a tert-butyl group, a benzyl group, a trimethylsilyl group, and an isopropyldimethylsilyl group. Examples of the base which may be employed include carbonates, hydrogencarbonates, and hydroxides of alkali metals and alkaline earth metals; trialkylamines such as triethylamine and N,N-diisopropylethylamine; pyridine; 1,8-diazabicycloundecene; and N-methylpiperidine. Preferably, triethylamine is employed. No particular limitation is imposed on the solvent to be employed, so long as it does not impede reaction. N,N-dimethylformamide, dimethyl sulfoxide, sulfolane, acetonitrile, ethanol, dimethylacetamide, tetrahydrofuran, or N-methylpyrrolidone is preferred, with dimethyl sulfoxide or sulfolane being particularly preferred.

Subsequently, compound (4) is subjected to hydrolysis, followed by deprotection of the amino protective group, to thereby yield the compound (I-1) of the present invention. Hydrolysis of compound (4) can be performed under generally employed conditions. For example, the hydrolysis can be performed by causing a base to act on compound (4) in an alcohol solvent (e.g., methanol or ethanol). The base is preferably triethylamine. The reaction is preferably performed under ice cooling. The deprotection can be performed under conditions suitable for the employed protective group. For example, the deprotection is performed by treating the above-hydrolyzed product with concentrated hydrochloric acid. After completion of reaction, the reaction mixture is treated with, for example, an aqueous sodium hydroxide solution so that the resultant reaction mixture becomes basic.

The target product may be obtained by use of a carboxylic acid compound in place of compound (4), which is a boron chelate.

The compound (I) of the present invention exhibits potent antibacterial activity almost comparable to that of a known synthetic quinolone antibacterial agent, and exhibits low convulsion-inducing effect and chromosomal-aberration-inducing effect and high safety. Therefore, the compound can be employed as a drug for humans, animals, and fish or as a preservative for agricultural chemicals and food. When the compound of the present invention is employed as a drug for humans, the daily dose for an adult is 50 mg to 1 g, preferably 100 to 500 mg. When the compound is employed for veterinary purposes, the dose differs depending on the purpose of the administration, the size of the animal to be treated, the type of the pathogenic bacteria infecting the animal, and the severity of the infection. The daily dose is generally 1 to 200 mg, preferably 5 to 100 mg per kg (the weight of the animal). The daily dose is administered once a day, or 2 to 4 times a day in a divided manner. If necessary, the daily dose may exceed the aforementioned range.

The compound (I) of the present invention is active on a broad range of microorganisms which cause various infectious diseases, and thus is useful in treatment, prevention, or alleviation of pathological conditions caused by these pathogens. Examples of bacteria or bacteria-like microorganisms on which the compound of the present invention exhibits efficacy include those belonging to the genus *Staphylococcus*, *Streptococcus pyogenes*, hemolytic streptococci, *Enterococcus*, *Streptococcus pneumoniae*, the genus *Peptostreptococcus*, *Neisseria gonorrhoeae*, *Escherichia coli*, the genus *Citrobacter*, the genus *Shigella*, *Klebsiella pneumoniae*, the genus *Enterobacter*, the genus *Serratia*, the genus *Proteus*, *Pseudomonas aeruginosa*, *Haemophilus influenzae*, the genus *Acinetobacter*, the genus *Campylobacter*, and *Chlamydia trachomatis*.

Examples of pathological conditions caused by these pathogens include folliculitis, furuncle, carbuncle, erysipelas, phelegmon, lymphangitis or lymphadenitis, panaritium, subcutaneous abscess, hidrosadenitis, aggregated acne, infectious atheroma, anal abscess, mastitis, superficial secondary infections caused by trauma, burn, operative wound, or similar wounds, laryngopharyngitis, acute bronchitis, tonsillitis, chronic bronchitis, bronchiectasis, diffuse panbronchiolitis, secondary infection caused by chronic respiratory diseases, pneumonia, pyelonephritis, cystitis, prostatitis, epididymitis, gonococcal urethritis, non-gonococcal urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, otitis media, sinusitis, periodontitis, pericoronitis, gnathitis, peritonitis, endocarditis, sepsis, meningitis, and skin infectious diseases.

Examples of acid-fast bacteria on which the compound (I) of the present invention exhibits efficacy include members of the so-called *Mycobacterium tuberculosis* complex (*Mycobacterium tuberculosis*, *M. bovis*, *M. africanum*) and atypical acid-fast bacteria (*M. kansasii*, *M. marinum*, *M. scrofulaceum*, *M. avium*, *M. intracellulare*, *M. xenopi*, *M. fortuitum*, *M. chelonae*). Acid-fast bacterial infectious diseases caused by any of these pathogens are broadly categorized into three groups; i.e., tuberculosis, atypical acid-fast bacterial disease, and lepra, based on the identity of the causal bacterium.

*Mycobacterium tuberculosis* infections can be seen not only in the lungs, but also in the thoracic cavity, trachea/bronchi, lymph nodes, systemically disseminated, bone joints, meninges or brain, digestive organs (intestine or liver), skin, mammary gland, eye, middle ear or throat, urinary tract, male genital organs, and female genital organs. Atypical acid-fast bacteriosis (nontuberculous mycobacteriosis) is primarily found in the lung, but also found in local lymphadenitis, skin soft tissue, bone joints, and systemic disseminated pathological condition.

The compound of the present invention is effective on a variety of microorganisms which cause infectious disease in animals. Examples of such microorganisms include those belonging to the genus *Escherichia*, the genus *Salmonella*, the genus *Pasteurella*, the genus *Haemophilus*, the genus *Bordetella*, the genus *Staphylococcus*, and the genus *Mycoplasma*. Specific examples of diseases include, in birds, *Escherichia coli* infections, pullorum disease, avian paratyphoid, fowl cholera, infectious coryza, staphylococcosis, and mycoplasma infections; in pigs, *Escherichia coli* infections, salmonellosis, pasteurellosis, *Haemophilus* infections, atrophic rhinitis, exudative epidermitis, mycoplasma infections; in cattle, *Escherichia coli* infections, salmonellosis, hemorrhagic septicemia, mycoplasma infections, contagious bovine pleuropneumonia, and mastitis; in dogs, *Escherichia coli septicemia, salmonella* infections, hemorrhagic septicemia, uterine empyema, and cystitis; and in cats, exudative pleurisy, cystitis, chronic rhinitis, *haemophilus* infections, kitten diarrhea, and mycoplasma infections.

Antibacterial drugs containing the compound (I) of the present invention can be prepared by selecting a suitable drug form in consideration of the manner of administration and using any of ordinarily employed preparation methods. Examples of the form of the antibacterial drugs containing the compound of the present invention include tablets, powders, granules, capsules, solutions, syrups, elixirs, oil or aqueous suspensions. Injection drugs may contain a stabilizer, a preservative, or a solubilizing agent. Alternatively, a solution which may contain any of these additives may be placed in a container and converted into solid through, for example, freeze-drying, and the thus-prepared solid preparation may be restituted before use. In this connection, a single dose or a plurality of doses may be contained into one container. Exemplary external application forms include solutions, suspensions, emulsions, ointments, gels, creams, lotions, and sprays. Solid preparations may contain pharmaceutically acceptable additives along with the active compound. Examples of such additives include fillers, binders, disintegrators, dissolution accelerators, humectants, and lubricants. Exemplary liquid preparation forms include solutions, suspensions, and emulsions, and they may contain as an additive a suspending agent, an emulsifier, or the like.

Next will be described formulation examples of antibacterial drugs containing the compound of the present invention.

FORMULATION EXAMPLE 1

Capsule

| | |
|---|---|
| Compound of Example 1 | 100.0 mg |
| Cornstarch | 23.0 mg |
| CMC calcium | 22.5 mg |
| Hydroxymethyl cellulose | 3.0 mg |
| Magnesium stearate | 1.5 mg |
| Total | 150.0 mg |

FORMULATION EXAMPLE 2

Solution

| | |
|---|---|
| Compound of Example 2 | 1 to 10 g |
| Acetic acid or sodium hydroxide | 0.5 to 2 g |
| Ethyl p-hydroxybenzoate | 0.1 g |
| Purified water | 87.9 to 98.4 g |
| Total | 100 g |

FORMULATION EXAMPLE 3

Powder for Mixing with Feed

| | |
|---|---|
| Compound of Example 3 | 1 to 10 g |
| Cornstarch | 89.5 to 98.5 g |
| Light anhydrous silicic acid | 0.5 g |
| Total | 100 g |

EXAMPLE

The present invention will next be described in more detail by way of Referential Examples and Examples, which should not be construed as limiting the invention thereto.

REFERENTIAL EXAMPLE 1

(3S,4S)-1-Benzyloxycarbonyl-3-(tert-butoxycarbonyl)amino-4-(p-toluenesulfonyloxy)methylpyrrolidine (3S,4S)-1-Benzyloxycarbonyl-3-(tert-butoxycarbonyl) amino-4-hydroxymethylpyrrolidine (5.00 g, 14.3 mmol) was dissolved in pyridine (50 mL). p-Toluenesulfonyl chloride (4.08 g, 21.4 mmol) and 4-(N,N-dimethyl)aminopyridine (174 mg, 1.43 mmol) were added thereto at room temperature, and the resultant mixture was stirred under a nitrogen atmosphere for 24 hours. Under cooling, ethyl acetate (200 mL) and 1 mol/L hydrochloric acid (200 mL) were added thereto, followed by extraction with ethyl acetate (200 mL×2). The organic layer was washed sequentially by 1 mol/L hydrochloric acid (100 mL), saturated sodium hydrogencarbonate (100 mL), and saturated brine (100 mL), and dried over anhydrous sodium sulfate. After filtration, the filtrate was concentrated under reduced pressure. The residue was purified through silica gel column chromatography (ethyl acetate:n-hexane=1:1), to thereby yield the title compound as a colorless amorphous substance (6.27 g, 87%).

$^1$H-NMR (400 MHz, CDCl$_3$) δ ppm: 1.42 (9H, s), 2.44 (3H, s), 2.58-2.68 (1H, m), 3.17-3.36 (2H, m), 3.59-3.69 (2H, m), 3.90-4.08 (1H, m), 4.22 (1H, dd, J=4.9, 10.5 Hz), 4.25-4.38 (1H, m), 4.60 (1H, d, J=29.1 Hz), 5.11 (2H, s), 7.27-7.42 (7H, m), 7.76 (2H, d, J=8.1 Hz).

MS (EI) m/z: 405 (M-Boc)$^+$.

REFERENTIAL EXAMPLE 2

(3S,4S)-1-Benzyloxycarbonyl-3-(tert-butoxycarbonyl)amino-4-ethylpyrrolidine

Under cooling with ice, a solution of methyllithium (121 mL, 1.02 M, diethyl ether solution) was added to a suspension of copper(I) iodide (11.8 g, 62.1 mmol) in diethyl ether (200 mL), followed by stirring for 30 minutes. The temperature of the reaction mixture was cooled to −78° C. A solution of (3S,4S)-1-benzyloxycarbonyl-3-(tert-butoxycarbonyl)amino-4-(p-toluenesulfonyloxy)methylpyrrolidine (6.27 g, 12.4 mmol) in diethyl ether (140 mL) was added thereto. The temperature of the mixture was elevated gradually, followed by stirring for 1 hour under cooling with ice. Under cooling with ice, a saturated aqueous ammonium chloride solution (100 mL) and 28% aqueous ammonia (25 mL) were added to the resultant mixture, and then water (100 mL) was added thereto, followed by extraction with ethyl acetate (300 mL×2). The combined organic layer was washed by saturated brine (100 mL), and dried over anhydrous sodium sulfate. The filtrate was concentrated under reduced pressure. The residue was purified through silica gel column chromatography (ethyl acetate:n-hexane=1:3 to 1:2), to thereby yield the title compound as a colorless oily substance (3.09 g, 71%).

$^1$H-NMR (400 MHz, CDCl$_3$) δ ppm: 0.93-0.97 (3H, m), 1.44 (9H, s), 1.27-1.55 (2H, m), 2.09-2.23 (1H, m), 3.02 (1H, q, J=11.1 Hz), 3.41-3.68 (3H, m), 4.24 (1H, brs), 4.47-4.64 (1H, m), 5.07-5.18 (2H, m), 7.28-7.42 (5H, m).

IR(ATR)ν cm$^{-1}$: 3321, 2966, 2937, 2877, 1684, 1525, 1454, 1417, 1363, 1331, 1244, 1161.

$[α]_D^{19.5}$ −2.49° (c1.000, CHCl$_3$).

MS (FAB+) m/z: 349 (M+1)$^+$.

HRMS (FAB+) m/z: Calcd for C$_{19}$H$_{28}$N$_2$O$_4$+H, 349.2127. Found: 349.2117.

REFERENTIAL EXAMPLE 3

(3S,4S)-3-(tert-Butoxycarbonyl)amino-4-ethylpyrrolidine

A 10% palladium carbon catalyst (50 mg) was added to a solution of (3S,4S)-1-benzyloxycarbonyl-3-(tert-butoxycarbonyl)amino-4-ethylpyrrolidine (514 mg, 1.48 mmol) in methanol (15 mL). The resultant mixture was stirred at room temperature for 2 hours under an ordinary pressure in a hydrogen atmosphere. After filtration, the filtrate was concentrated under reduced pressure, to thereby yield the title compound as a colorless oily substance (324 mg, quantitative amount).

$^1$H-NMR (400 MHz, CDCl$_3$) δ ppm: 0.94 (3H, t, J=7.4 Hz), 1.21-1.33 (1H, m), 1.44 (9H, s), 1.40-1.54 (1H, m), 1.95-2.08 (1H, m), 2.53 (1H, t, J=10.0 Hz), 2.79 (1H, dd, J=3.1, 11.1 Hz), 3.12-3.24 (2H, m), 4.16 (1H, brs), 4.75 (1H, brs).

MS (EI) m/z: 215 (M+1)$^+$.

EXAMPLE 1

7-[(3S,4S)-3-Amino-4-ethylpyrrolidin-1-yl]-6-fluoro-1-[(1R,2S)-2-fluorocyclopropyl]-8-methoxy-1,4-dihydro-4-oxoquinoline-3-carboxylic acid (Compound No. 1)

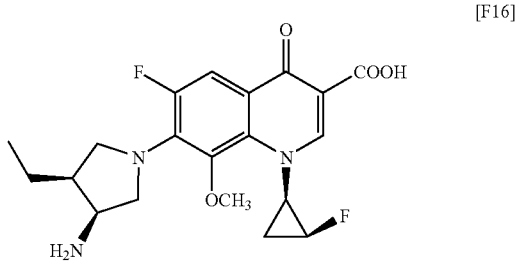

[F16]

6,7-Difluoro-1-[(1R,2S)-2-fluorocyclopropyl]-8-methoxy-1,4-dihydro-4-oxoquinoline-3-carboxylic acid difluoroboran complex (484 mg, 1.34 mmol) and triethylamine (224 μL, 1.61 mmol) were added to a solution of (3S,4S)-3-(tert-butoxycarbonyl)amino-4-ethylpyrrolidine (324 mg, 1.48 mmol) in dimethyl sulfoxide (5 mL), and the mixture was stirred at room temperature for 4 hours. Subsequently, water (100 mL) was added to the reaction mixture, and a precipitated yellow solid was collected through filtration. Ethanol (10 mL) and water (2.5 mL) were added so as to dissolve the solid, and triethylamine (2.5 mL) was added to the solution, followed by refluxing in an oil bath at 90° C. for 4 hours. The reaction mixture was concentrated under reduced pressure, and a 10% aqueous citric acid solution (20 mL) was added thereto, followed by extraction with chloroform (50 mL×2). The thus-obtained organic layer was dried over anhydrous sodium sulfate. After filtration, the filtrate was concentrated under reduced pressure to thereby obtain a yellow solid. Subsequently, concentrated hydrochloric acid (10 mL) was added to the solid at room temperature, followed by stirring for 30 minutes. The reaction mixture was washed by chloroform (50 mL×3), and the pH of the obtained aqueous layer was adjusted to 11.0 with a 10 mol/L aqueous sodium hydroxide solution under cooling with ice. The pH was adjusted again to 7.4. The resultant mixture was extracted sequentially with a methanol-chloroform mixture (1:4) (200 mL×2), and chloroform (100 mL). The combined organic layer was dried over anhydrous sodium sulfate, filtered, and concentrated under reduced pressure. The residue was recrystallized from an ethanol-28% aqueous ammonia mixture (6:1), followed by drying under reduced pressure, to thereby yield the title compound as yellow crystals (441 mg, 80%).

mp: 217-219° C.

$^1$H-NMR (400 MHz, 0.1 mol/L NaOD) δ ppm: 0.93-1.02 (3H, m), 1.36-1.57 (4H, m), 2.07-2.21 (1H, m), 3.34 (1H, d, J=10.0 Hz), 3.48-3.62 (6H, m), 3.83 (1H, s), 3.95-4.04 (1H, m), 5.01 (1H, dm, J=63.5 Hz), 7.64 (1H, d, J=14.6 Hz), 8.40 (1H, d, J=2.2 Hz).

IR(ATR)ν cm$^{-1}$: 3388, 3078, 3037, 2952, 2873, 1724, 1618, 1510, 1435, 1367, 1327, 1271, 1230.

$[α]_D^{24.2}$ −121.03° (c0.397, 0.1 mol/L NaOH).

MS (EI) m/z: 408 (M+1)$^+$.

Anal.: Calcd for C$_{20}$H$_{23}$F$_2$N$_3$O$_4$·0.25H$_2$O: C, 58.32; H, 5.75; N, 10.20%. Found: C, 58.49; H, 5.67%; N, 10.29.

EXAMPLE 2

7-[(3S,4S)-3-Amino-4-ethylpyrrolidin-1-yl]-6-fluoro-1-[(1R,2S)-2-fluorocyclopropyl]-8-methyl-1,4-dihydro-4-oxoquinoline-3-carboxylic acid (Compound No. 2)

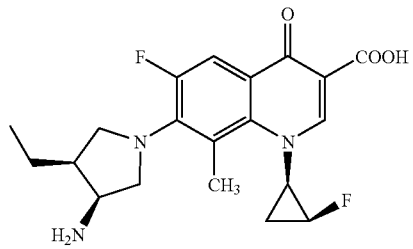

[F17]

6,7-Difluoro-1-[(1R,2S)-2-fluorocyclopropyl]-8-methyl-1,4-dihydro-4-oxoquinoline-3-carboxylic acid difluoroboran complex (455 mg, 1.32 mmol) and triethylamine (221 μL, 1.58 mmol) were added to a solution of (3S,4S)-3-(tert-butoxycarbonyl)amino-4-ethylpyrrolidine (311 mg, 1.45 mmol) in sulfolane (4 mL), and the mixture was stirred in an oil bath at 45° C. for 48 hours. Subsequently, ethanol (20 mL), water (5 mL), and triethylamine (5 mL) were added to the reaction mixture, followed by refluxing in an oil bath at 90° C. for 5 hours. The reaction mixture was concentrated under reduced pressure, and a 10% aqueous citric acid solution (30 mL) was added thereto, followed by extraction with ethyl acetate (100 mL×2). The thus-obtained organic layer was washed sequentially by water (50 mL×3) and saturated brine (50 mL), and dried over anhydrous sodium sulfate. After filtration, the filtrate was concentrated under reduced pressure. Subsequently, concentrated hydrochloric acid (10 mL) was added to the obtained bark oily substance at room temperature, and the reaction mixture was washed by chloroform (50 mL×3), and the pH of the obtained aqueous layer was adjusted to 12.0 with a 10 mol/L aqueous sodium hydroxide solution under cooling with ice. The pH was adjusted again to 7.4. The resultant mixture was extracted with chloroform (200 mL×2). The combined organic layer was dried over anhydrous sodium sulfate, filtered, and concentrated under reduced pressure. The obtained residue was recrystallized from ethanol, and dried under reduced pressure, to thereby yield the title compound as pale bark crystals (65.0 mg, 12%).

mp: 214-216° C.

$^1$H-NMR (400 MHz, 0.1 mol/L NaOD) δ ppm: 0.97 (3H, t, J=7.4 Hz), 1.15-1.28 (1H, m), 1.41-1.66 (3H, m), 2.14-2.25 (1H, m), 2.42 (3H, s), 3.13 (1H, d, J=10.3 Hz), 3.29 (1H, t, J=8.7 Hz), 3.49-3.60 (2H, m), 3.99-4.09 (2H, m), 5.02 (1H, dm, J=64.5 Hz), 7.65 (1H, d, J=14.4 Hz), 8.43 (1H, d, J=3.2 Hz).

IR(ATR)ν cm$^{-1}$: 3390, 3084, 3037, 2964, 2912, 1712, 1616, 1510, 1468, 1435, 1350, 1308.

MS (EI) m/z: 392 (M+1)$^+$.

Anal.: Calcd for $C_{20}H_{23}F_2N_3O_3 \cdot 0.25H_2O$: C, 60.67; H, 5.98; N, 10.61; F, 9.60. Found: C, 60.85; H, 5.89; N, 10.53; F, 9.55.

EXAMPLE 3

(3S)-10-[(3S,4S)-3-Amino-4-ethylpyrrolidin-1-yl]-9-fluoro-2,3-dihydro-3-methyl-7-oxo-7H-pyrido[1,2,3-de][1,4]benzoxazine-6-carboxylic acid (Compound No. 3)

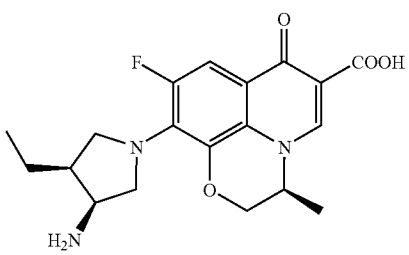

[F18]

(3S)-9,10-Difluoro-2,3-dihydro-3-methyl-7-oxo-7H-pyrido[1,2,3-de][1,4]benzoxazine-6-carboxylic acid difluoroboran complex (193 mg, 587 μmol) and triethylamine (98.2 μL, 704 μmol) were added to a solution of (3S,4S)-3-(tert-butoxycarbonyl)amino-4-ethylpyrrolidine (138 mg, 644 μmol) in dimethyl sulfoxide (3 mL), and the mixture was stirred at room temperature for 16 hours. The reaction mixture was concentrated under reduced pressure, and ethanol (4 mL) and water (1 mL) were added so as to dissolve the concentrated product. Subsequently, triethylamine (1 mL) was added to the solution, followed by refluxing in an oil bath at 90° C. for 2 hours. The reaction mixture was concentrated under reduced pressure, and dissolved in chloroform (50 mL). The solution was washed by a 10% aqueous citric acid solution (30 mL). The obtained organic layer was dried over anhydrous sodium sulfate, filtered, and concentrated under reduced pressure. Subsequently, concentrated hydrochloric acid (6 mL) was added to the obtained yellow solid at room temperature, followed by stirring for 30 minutes. The reaction mixture was transferred to a separatory funnel with 1 mol/L hydrochloric acid (20 mL), followed by washing with chloroform (50 mL). Subsequently, the pH of the obtained aqueous layer was adjusted to 12.0 with a 10 mol/L aqueous sodium hydroxide solution under cooling with ice. The pH was adjusted again to 7.4. The resultant mixture was extracted with chloroform (200 mL×2). The combined organic layer was dried over anhydrous sodium sulfate, and the solvent was removed under reduced pressure. The obtained residue was recrystallized from an ethanol-28% aqueous ammonia (10:1) solvent mixture, and dried under reduced pressure, to thereby yield the title compound as yellow crystals (176 mg, 79%).

mp: 239-241° C.

$^1$H-NMR (400 MHz, 0.1 mol/L NaOD) δ ppm: 0.95 (3H, t, J=7.3 Hz), 1.49 (3H, d, J=6.6 Hz), 1.34-1.51 (2H, m), 2.06 (1H, brs), 3.31 (1H, d, J=10.5 Hz), 3.43-3.60 (3H, m), 3.90-4.00 (1H, m), 4.24 (1H, d, J=11.2 Hz), 4.42 (1H, d, J=11.5 Hz), 4.50-4.60 (1H, m), 7.45 (1H, d, J=14.2 Hz), 8.30 (1H, s).

IR(ATR)ν cm$^{-1}$: 3388, 3035, 2972, 2871, 1697, 1612, 1520, 1431, 1400, 1344, 1315, 1273, 1203.

$[α]_D^{24.8}$ -207.15° (c0.390, 0.1 mol/L NaOH).

MS (EI) m/z: 376 (M+1)$^+$.

Anal.: Calcd for $C_{19}H_{22}FN_3O_4 \cdot 0.25H_2O$: C, 60.07; H, 5.97; N, 11.06; F, 5.00. Found: C, 60.30; H, 5.86; N, 11.12; F, 5.02.

REFERENTIAL EXAMPLE 4

(3S,4S)-1-Benzyloxycarbonyl-3-(tert-butoxycarbonyl)amino-4-propylpyrrolidine Under a nitrogen atmosphere, ethylmagnesium bromide (3.6 mL, 3.2 mmol, 0.89M tetrahydrofuran solution) was added dropwise to a suspension of copper iodide (38 mg) in diethyl ether (1 mL) at −30° C. Subsequently, a solution of (3S,4S)-1-benzyloxycarbonyl-3-(tert-butoxycarbonyl) amino-4-(p-toluenesulfonyloxy)methylpyrrolidine (400 mg, 0.792 mmol) in diethyl ether (4 mL) was added dropwise thereto. The mixture was stirred for 2 hours while the temperature thereof was gradually elevated to 10° C. A saturated aqueous ammonium chloride solution and 28% aqueous ammonia were added sequentially thereto, and then the mixture was stirred until insoluble matter was dissolved. The resultant mixture was extracted with diethyl ether (100 mL×2), washed by saturated brine (100 mL), and dried over anhydrous magnesium sulfate. After filtration, the filtrate was concentrated through solvent removal. The residue was purified through silica gel column chromatography (n-hexane: ethyl acetate=4:1), to thereby yield the title compound as colorless crystals (106 mg, 36.9%).

$^1$H-NMR (400 MHz, CDCl$_3$) δ ppm: 0.90-0.92 (3H, m), 1.24-1.45 (13H, m), 2.20-2.30 (1H, m), 3.00 (1H, q, J=10.5 Hz), 3.40-3.68 (3H, m), 4.18-4.25 (1H, m), 4.55 (1H, br), 5.12 (2H, s), 7.31-7.38 (5H, m).

IR(ATR)ν cm$^{-1}$: 3282, 2958, 2873, 1698, 1681, 1666, 1413, 1162, 1060, 696.

HRMS (FAB) m/z: Calcd for C$_{20}$H$_{31}$O$_4$N$_2$: 363.2284. Found: 363.2266.

REFERENTIAL EXAMPLE 5

(3S,4S)-3-(tert-Butoxycarbonyl)amino-4-propylpyrrolidine

A mixture of (3S,4S)-1-benzyloxycarbonyl-3-(tert-butoxycarbonyl)amino-4-propylpyrrolidine (4.02 g, 11.09 mmol) and a 10% palladium carbon catalyst (1.0 g) in ethanol (100 mL) was stirred hard for 20 hours under an ordinary pressure in a hydrogen atmosphere. Insoluble matter was removed through filtration by use of Celite, and then ethanol was removed under reduced pressure. The residue was dissolved in diethyl ether (200 mL), and the solution was washed by a 1 mol/L aqueous sodium hydroxide solution (100 mL), followed by drying over anhydrous sodium sulfate. After filtration, the filtrate was concentrated under reduced pressure, to thereby yield the title compound as a colorless oily substance (2.34 g, 92.4%).

$^1$H-NMR (400 MHz, CDCl$_3$) δ ppm: 0.91 (3H, t, J=7.0 Hz), 1.18-1.45 (13H, m), 1.76 (1H, br), 2.06-2.13 (1H, m), 2.50 (1H, t, J=10.0 Hz), 2.77 (1H, dd, J=3.0, 11.0 Hz), 3.12-3.22 (2H, m), 4.10-4.16 (1H, m), 4.65 (1H, br).

MS (ESI) m/z: 229 (M$^+$+1).

EXAMPLE 4

7-[(3S,4S)-3-Amino-4-propylpyrrolidin-1-yl]-6-fluoro-1-[(1R,2S)-2-fluorocyclopropyl]-8-methoxy-1,4-dihydro-4-oxoquinoline-3-carboxylic acid (Compound No. 4)

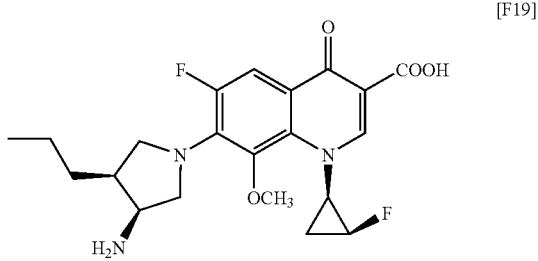

[F19]

6,7-Difluoro-1-[(1R,2S)-2-fluorocyclopropyl]-8-methoxy-1,4-dihydro-4-oxoquinoline-3-carboxylic acid difluoroboran complex (505 mg, 1.40 mmol) and triethylamine (1.0 mL) were added to a solution of (3S,4S)-3-(tert-butoxycarbonyl)amino-4-propylpyrrolidine (342 mg, 1.50 mmol) in dimethyl sulfoxide (3 mL), followed by stirring at room temperature for 7 days. Subsequently, water (100 mL) was added to the reaction mixture, and a precipitated yellow solid was collected through filtration. Ethanol (45 mL) and water (5 mL) were added so as to dissolve the solids, and triethylamine (10 mL) was added to the solution, followed by refluxing for 2 hours. The reaction mixture was concentrated under reduced pressure, and a 10% aqueous citric acid solution (20 mL) was added thereto, followed by extraction with chloroform (50 mL×2). The combined organic layer was washed by saturated brine (50 mL), and the thus-obtained organic layer was dried over anhydrous sodium sulfate. After filtration, the filtrate was concentrated under reduced pressure. Subsequently, concentrated hydrochloric acid was added so as to dissolve the obtained residue at room temperature, followed by stirring for 30 minutes. The reaction mixture was washed by chloroform (50 mL×3), and the pH of the obtained aqueous layer was adjusted to 11.0 with a 10 mol/L aqueous sodium hydroxide solution under cooling with ice. The pH was adjusted again to 7.5. The resultant mixture was extracted with chloroform (200 mL×3). The combined organic layer was dried over anhydrous sodium sulfate, filtered, and concentrated under reduced pressure. The obtained residue was recrystallized from a mixture of 2-propanol and a small amount of ethanol, and dried under reduced pressure, to thereby yield the title compound as orange-yellow crystals (380 mg, 63.7%).

mp: 79-83° C.

$^1$H-NMR (400 MHz, DMSO-d$_6$) δ ppm: 0.92 (3H, t, J=7.0 Hz), 1.27-1.54 (6H, m), 2.05-2.11 (1H, m), 3.22-3.39 (1H, m), 3.43-3.48 (2H, m), 3.52 (3H, s), 3.61 (1H, dt, J=4.0, 10.0 Hz), 3.90 (1H, dt, J=4.5, 10.5 Hz), 4.05 (1H, dt, J=5.5, 9.0 Hz), 5.00-5.20 (1H, m), 7.63 (1H, d, J=14.0 Hz), 8.58 (1H, d, J=3.5 Hz).

IR(ATR)ν cm$^{-1}$: 3383, 2929, 2871, 1616, 1541, 1429, 1313, 1051, 928, 804.

[α]$_D$ −226.08° (c0.265, DMSO).

Anal.: Calcd for C$_{21}$H$_{25}$F$_2$N$_3$O$_4$·0.25H$_2$O: C, 59.22; H, 6.03; N, 9.87; F, 8.92. Found: C, 59.18; H, 6.01; N, 9.92; F, 9.11.

EXAMPLE 5

7-[(3S,4S)-3-Amino-4-propylpyrrolidin-1-yl]-6-fluoro-1-[(1R,2S)-2-fluorocyclopropyl]-8-methyl-1,4-dihydro-4-oxoquinoline-3-carboxylic acid-hydrochloride (Compound No. 5)

[F20]

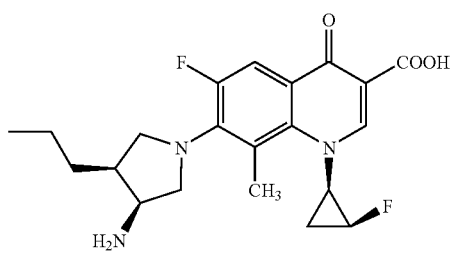

6,7-Difluoro-1-[(1R,2S)-2-fluorocyclopropyl]-8-methyl-1,4-dihydro-4-oxoquinoline-3-carboxylic acid difluoroboran complex (455 mg, 1.32 mmol) and triethylamine (1.5 mL) were added to a solution of (3S,4S)-3-(tert-butoxycarbonyl)amino-4-propylpyrrolidine (731 mg, 3.20 mmol) in dimethyl sulfoxide (5 mL), and the mixture was stirred at room temperature under a nitrogen atmosphere for 2 weeks. The reaction mixture was concentrated under reduced pressure. Subsequently, water was added to the residue, and precipitated crystals were collected through filtration. Ethanol (45 mL), water (5 mL), and triethylamine (10 mL) were added to the obtained crystals, followed by refluxing for 3 hours. The reaction mixture was concentrated under reduced pressure, and the residue was dissolved in chloroform (100 mL). The obtained organic layer was washed sequentially by a 10% aqueous citric acid solution (50 mL) and saturated brine (50 mL), dried over anhydrous sodium sulfate, filtered, and concentrated under reduced pressure. Subsequently, concentrated hydrochloric acid was added at room temperature so as to dissolve the obtained residue. The reaction mixture was washed by chloroform (50 mL×3), and the pH of the obtained aqueous layer was adjusted to 12.0 with a 10 mol/L aqueous sodium hydroxide solution under cooling with ice. The pH was adjusted again to 7.6. The resultant mixture was extracted with chloroform (200 mL×2). The combined organic layer was dried over anhydrous sodium sulfate, filtered, and concentrated under reduced pressure. The obtained residue was purified through fractional thin-layer chromatography (chloroform:methanol:water=7:3:1, developer). The obtained crystals were dissolved in concentrated hydrochloric acid, and the solution was concentrated under reduced pressure. The obtained residue was recrystallized from 2-propanol, to thereby yield the title compound as an orange crystals (190 mg, 13.2%).

mp: 197-207° C.

$^1$H-NMR (400 MHz, D$_2$O) δ ppm: 0.90 (3H, t, J=6.5 Hz), 1.08-1.60 (6H, m), 2.13-2.21 (1H, m), 2.35 (3H, s), 3.04 (1H, d, J=9.5 Hz), 3.17 (1H, t, J=8.5 Hz), 3.39-3.42 (1H, m), 3.50 (1H, t, J=9.0 Hz), 3.88-4.02 (2H, m), 4.90-5.07 (1H, m), 7.61 (1H, d, J=14.0 Hz), 8.41 (1H, d, J=3.0 Hz).

IR(ATR)ν cm$^{-1}$: 2870, 1716, 1614, 1427, 1315, 1128, 1026, 926, 806.

[α]$_D$ −299.45° (c0.309, 0.1 mol/L NaOH).

Anal.: Calcd for C$_{21}$H$_{25}$F$_2$N$_3$O$_3$—HCl.0.5H$_2$O.0.5C$_3$H$_7$OH: C, 56.19; H, 6.50; N, 8.74; F, 7.90; Cl, 7.37. Found: C, 55.88; H, 6.45; N, 8.90; F, 8.11; Cl, 7.60.

EXAMPLE 6

(3S)-10-[(3S,4S)-3-Amino-4-propylpyrrolidin-1-yl]-9-fluoro-2,3-dihydro-3-methyl-7-oxo-7H-pyrido[1,2,3-de][1,4]benzoxazine-6-carboxylic acid-hydrochloride (Compound No. 6)

[F21]

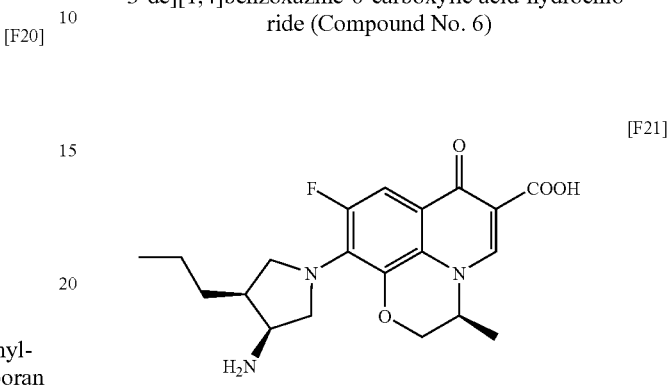

(3S)-9,10-Difluoro-2,3-dihydro-3-methyl-7-oxo-7H-pyrido[1,2,3-de][1,4]benzoxazine-6-carboxylic acid difluoroboran complex (1.65 g, 5.00 mol) and triethylamine (2 mL) were added to a solution of (3S,4S)-3-(tert-butoxycarbonyl)amino-4-propylpyrrolidine (1.26 g, 5.52 mmol) in dimethyl sulfoxide (10 mL), followed by stirring at room temperature for 6 days. The reaction mixture was concentrated under reduced pressure. Subsequently, water was added thereto, and precipitated crystals were collected through filtration. Ethanol (90 mL) and water (10 mL) were added so as to dissolve the obtained crystals, and triethylamine (20 mL) was added to the solution, followed by refluxing for 3 hours. The reaction mixture was concentrated under reduced pressure, and dissolved in chloroform (300 mL). The solution was washed sequentially by a 10% aqueous citric acid solution (200 mL) and saturated brine (100 mL). The obtained organic layer was dried over anhydrous sodium sulfate, filtered, and concentrated under reduced pressure. Subsequently, concentrated hydrochloric acid was added so as to dissolve the obtained yellow solid at room temperature, and the solution was stirred for 30 minutes. The reaction mixture was washed by chloroform (50 mL), and the thus-obtained aqueous layer was diluted. Subsequently, the precipitated crystals were collected through filtration, recrystallized from ethanol, and dried over under reduced pressure, to thereby yield the title compound as yellow crystals (1.44 g, 59.4%). Separately, the pH of the above-obtained aqueous layer acidified with hydrochloric acid was adjusted to 7.7 with an aqueous sodium hydroxide solution. The resultant mixture was extracted with chloroform (100 mL×2), and dried over anhydrous sodium sulfate. After filtration, the filtrate was concentrated under reduced pressure. The obtained crystals were recrystallized from 2-propanol, to thereby yield the title compound as a free form (90 mg, 4.6%).

Hydrochloride (crystallized with ethanol):

mp: 225-231° C.

$^1$H-NMR (400 MHz, DMSO-d$_6$) δ ppm: 0.91 (3H, t, J=7.0 Hz), 1.26-1.49 (7H, m), 1.98-2.04 (1H, m), 3.30-3.40 (2H, m), 3.52-3.58 (1H, m), 3.73 (1H, dt, J=4.0, 10.0 Hz), 4.01-4.07 (1H, m), 4.21 (1H, dd, J=1.5, 11.0 Hz), 4.49 (1H, dd, J=1.5, 11.5 Hz), 4.81-4.87 (1H, m), 7.49 (1H, d, J=14.5 Hz), 8.84 (1H, s).

IR(ATR)ν cm$^{-1}$: 3388, 3035, 2954, 2871, 1705, 1614, 1433, 1354, 1115, 980, 804.

Anal.: Calcd for $C_{20}H_{24}FN_3O_4$·HCl·0.75$H_2O$: C, 54.67; H, 6.08; N, 9.56; F, 4.32; Cl, 8.07. Found: C, 54.35; H, 5.76; N, 9.56; F, 4.40; Cl, 7.68.

Free form (crystallized with 2-propanol):
mp: 213-217° C.
$[\alpha]_D$ −257.88° (c0.264, DMSO).
Anal.: Calcd for $C_{20}H_{24}FN_3O_4$: C, 61.68; H, 6.21; N, 10.79; F, 4.88. Found: C, 61.35; H, 6.02; N, 10.66; F, 4.90.

REFERENTIAL EXAMPLE 6

(3S,4S)-1-Benzyloxycarbonyl-3-(tert-butoxycarbonyl)amino-4-formylpyrrolidine (3S,4S)-1-Benzyloxycarbonyl-3-(tert-butoxycarbonyl)amino-4-hydroxymethylpyrrolidine (1.00 g, 2.85 mmol) was dissolved in dichloromethane (40 mL). Under cooling with ice, Dess Martin reagent (1.42 g, 3.42 mmol) was added thereto, and the resultant mixture was stirred at room temperature for 2 hours under a nitrogen atmosphere. Under cooling, 5% aqueous sodium thiosulfate solution (50 mL) was added thereto, followed by stirring for 0.5 hours. The aqueous layer was extracted with dichloromethane (30 mL×1), and the organic layer was washed sequentially by a 0.05 mol/L aqueous sodium hydroxide solution (60 mL) and saturated brine (100 mL), and dried over anhydrous sodium sulfate. After filtration, the filtrate was concentrated under reduced pressure, to thereby yield the title compound as a colorless oily substance (0.90 g, 91%).

$^1$H-NMR (400 MHz, CDCl$_3$) δ ppm: 1.42 (9H, s), 3.20-3.52 (2H, m), 3.53-3.65 (1H, m), 3.65-3.77 (1H, m), 3.77-3.95 (1H, m), 4.6.4 (1H, s), 4.90-5.21 (3H, m), 7.24-7.50 (5H, m), 9.77 (1H, s).

MS (ESI) m/z: 249 (M-Boc)$^+$.

REFERENTIAL EXAMPLE 7

(3S,4S)-1-Benzyloxycarbonyl-3-(tert-butoxycarbonyl)amino-4-vinylpyrrolidine

Under cooling with ice, titanium tetrachloride (3.30 mL, 1.0M toluene solution) was added to a suspension of zinc powder (1.86 g, 28.5 mmol) in tetrahydrofuran (15 mL) over 2 minutes, followed by stirring for 5 minutes at the same temperature. A solution of diiodomethane (1.15 mL, 14.3 mL) in tetrahydrofuran (5 mL) was added thereto over 8 minutes, and the resultant mixture was stirred for 15 minutes while the temperature thereof was elevated to room temperature. A solution of (3S,4S)-1-benzyloxycarbonyl-3-(tert-butoxycarbonyl)amino-4-formylpyrrolidine (900 mg, 2.58 mmol) in tetrahydrofuran (5.0 mL) was added thereto over 7 minutes, followed by stirring for 1.5 hours. Subsequently, under cooling with ice, the resultant mixture was poured to 0.5 mol/L hydrochloric acid (10 mL), followed by dilution with diethyl ether (60 mL). The obtained aqueous layer was extracted with diethyl ether (100 mL×2). The combined organic layer was washed by saturated brine (100 mL), dried over anhydrous sodium sulfate, filtered, concentrated under reduced pressure. The obtained residue was purified through silica gel column chromatography (ethyl acetate:n-hexane=1:3), to thereby yield the title compound as a colorless oily substance (3.09 g, 31%).

$^1$H-NMR (400 MHz, CDCl$_3$) δ ppm: 1.43 (9H, s), 2.89-3.02 (1H, m), 3.25-3.48 (2H, m), 3.56-3.74 (2H, m), 4.25 (1H, s), 4.57 (1H, s), 5.06-5.30 (4H, m), 5.71-5.84 (1H, m), 7.28-7.39 (5H, m).

MS (ESI+) m/z: 347 (M+1)$^+$.

REFERENTIAL EXAMPLE 8

(3S,4S)-3-(tert-Butoxycarbonyl)amino-4-vinylpyrrolidine

A solution of (3S,4S)-1-benzyloxycarbonyl-3-(tert-butoxycarbonyl)amino-4-vinylpyrrolidine (275 mg, 0.794 mmol) in tetrahydrofuran (5 mL) and sodium (300 mg, 13.0 mmol) were sequentially added to liquid ammonia (80 mL) at −78° C., and the mixture was stirred at the same temperature for 0.5 hours. The solvent was removed, followed by dilution with chloroform (80 mL). The resultant mixture was washed sequentially by 1 mol/L sodium hydroxide (30 mL) and saturated brine (100 mL), dried over anhydrous sodium sulfate, filtered, and concentrated under reduced pressure, to thereby yield the title compound as a colorless oily substance (168 mg, 100%).

$^1$H-NMR (400 MHz, CDCl$_3$) δ ppm: 1.44 (9H, s), 2.70-2.89 (3H, m), 3.13-3.33 (2H, m), 4.13 (1H, s), 4.60 (1H, s), 5.09-5.21 (2H, m), 5.80 (1H, ddd, J=7.4, 0.5, 17.6 Hz).

MS (ESI) m/z: 213 (M+1)$^+$.

EXAMPLE 7

(3S)-10-[(3S,4S)-3-Amino-4-vinyl-1-pyrrolidinyl]-9-fluoro-2,3-dihydro-3-methyl-7-oxo-7H-pyrido[1,2,3-de][1,4]benzoxazine-6-carboxylic acid (Compound No. 7)

[F22]

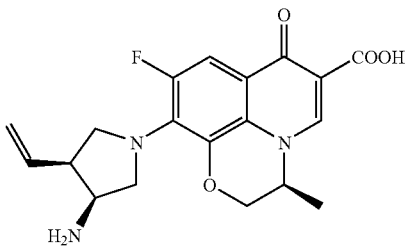

(3S)-9,10-Difluoro-2,3-dihydro-3-methyl-7-oxo-7H-pyrido[1,2,3-de][1,4]benzoxazine-6-carboxylic acid difluoroboran complex (233 mg, 709 μmol) and triethylamine (120 μL, 851 μmol) were added to a solution of (3S,4S)-3-(tert-butoxycarbonyl)amino-4-vinylpyrrolidine (180 mg, 780 μmol) in dimethyl sulfoxide (3.5 mL), followed by stirring at room temperature for 16 hours. Subsequently, water (10 mL) was added to the reaction mixture, and precipitated crystals were collected through filtration. The thus-collected crystals were suspended in a mixture of ethanol (10 mL) and water (2 mL). Thereafter, triethylamine (3 mL) was added thereto, followed by refluxing in an oil bath at 90° C. for 5 hours. The reaction mixture was concentrated under reduced pressure, and dissolved in chloroform (100 mL). The resultant solution was washed by a 10% aqueous citric acid solution (30 mL), and the obtained organic layer was dried over anhydrous sodium sulfate, filtered, concentrated under reduced pressure. Subsequently, concentrated hydrochloric acid (5 mL) was added to the obtained yellow solid under cooling with ice, followed by stirring for 45 minutes. The reaction mixture was transferred to a separatory funnel with 4 mol/L hydrochloric acid (5 mL), followed by washing with chloroform (50 mL×7). The pH of the obtained aqueous layer was adjusted to 12.0 with a 10 mol/L aqueous sodium hydroxide solution under cooling with ice. The pH was adjusted again to 7.4. The resultant mixture was extracted with chloroform (70 mL×3), and the combined organic layer was dried over anhydrous sodium sulfate, filtered, and concentrated under reduced pressure. The obtained residue was recrystallized from ethanol, and dried under reduced pressure, to thereby yield the title compound as yellow crystals (188 mg, 64%).

mp: 238-240° C.

$^1$H-NMR (400 MHz, 0.1 mol/L NaOD) δ ppm: 1.52 (3H, d, J=6.9 Hz), 2.91-3.00 (1H, m), 3.41 (1H, dq, J=10.4, 2.2 Hz), 3.56 (1H, dd, J=10.0, 5.6 Hz), 3.71-3.76 (2H, m), 3.92 (1H, ddd, J=10.5, 5.9, 2.4 Hz), 4.30 (1H, dd, J=11.4, 2.3 Hz), 4.48 (1H, dd, J=11.4, 2.1 Hz), 4.59 (1H, d, J=7.1 Hz), 5.23-5.32 (2H, m), 5.98 (1H, ddd, J=17.8, 10.1, 7.3 Hz), 7.52 (1H, d, J=14.2 Hz), 8.32 (1H, s).

IR(ATR)ν cm$^{-1}$: 3374, 2983, 2914, 1709, 1618, 1525, 1464, 1396, 1352, 1309, 1275, 1211.

$[α]_D^{24.8}$ −115.0° (c0.100, 0.1 mol/L NaOH).

MS (ESI) m/z: 374 (M+1)$^+$.

Anal.: Calcd for $C_{19}H_{22}FN_3O_4$: C, 61.12; H, 5.40; N, 11.25; F, 5.09. Found: C, 61.04; H, 5.32; N, 11.14; F, 4.95.

REFERENTIAL EXAMPLE 9

(3S,4S)-1-Benzyloxycarbonyl-3-(tert-butoxycarbonyl)amino-4-cyclopropylpyrrolidine An excessive amount of a solution of diazomethane in diethyl ether (30 mL) was added to (3S,4S)-1-benzyloxycarbonyl-3-(tert-butoxycarbonyl)amino-4-vinylpyrrolidine (270 mg, 779 mmol). Under cooling with ice, palladium acetate (10 mg) was added thereto, followed by stirring at room temperature for 2 hours. After completion of reaction, insoluble matter was removed through filtration. The filtrate was concentrated under reduced pressure, and the obtained residue was purified though silica gel column chromatography (ethyl acetate:n-hexane=1:9 to 1:4), to thereby yield the title compound as a colorless oily substance (269 mg, 96%).

$^1$H-NMR (400 MHz, CDCl$_3$) δ ppm: 0.08-0.29 (2H, m), 0.46-0.71 (3H, m), 1.45 (9H, s) 1.40-1.60 (1H, m), 3.27-3.41 (2H, m), 3.52-3.72 (2H, m), 4.24 (1H, brs), 4.70-4.90 (1H, m), 5.10-5.17 (2H, m), 7.28-7.40 (5H, m).

MS (EI) m/z: 388 (M+Na)$^+$.

REFERENTIAL EXAMPLE 10

(3S,4S)-3-(tert-Butoxycarbonyl)amino-4-cyclopropylpyrrolidine

A 10% palladium carbon catalyst (50 mg) was added to a solution of (3S,4S)-1-benzyloxycarbonyl-3-(tert-butoxycarbonyl)amino-4-cyclopropylpyrrolidine (408 mg, 1.13 mmol) in ethanol (5 mL), followed by stirring in a hydrogen atmosphere under an ordinary pressure at 45° C. for 12 hours. After filtration, the filtrate was concentrated under reduced pressure, to thereby yield the title compound as a colorless oily substance (255 mg, quantitative amount). The product was employed, without further purification, in the subsequent step.

MS (EI) m/z: 227 (M+1)$^+$.

EXAMPLE 8

7-[(3S,4S)-3-Amino-4-cyclopropylpyrrolidin-1-yl]-6-fluoro-1-[(1R,2S)-2-fluorocyclopropyl]-8-methoxy-1,4-dihydro-4-oxoquinoline-3-carboxylic acid (Compound No. 8)

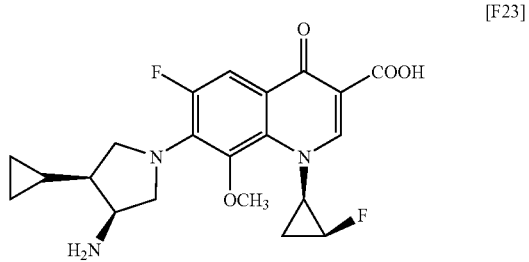

[F23]

6,7-Difluoro-1-[(1R,2S)-2-fluorocyclopropyl]-8-methoxy-1,4-dihydro-4-oxoquinoline-3-carboxylic acid difluoroboran complex (180 mg, 499 μmol) and triethylamine (83 μL, 598 μmol) were added to a solution of (3S,4S)-3-(tert-butoxycarbonyl)amino-4-cyclopropylpyrrolidine (113 mg, 499 μmol) in acetonitrile (1 mL), and the mixture was stirred at room temperature for 15 hours. The reaction mixture was concentrated under reduced pressure. Ethanol (5 mL) and water (1 mL) were added so as to dissolve the concentrated product. Subsequently, triethylamine (1 mL) was added to the solution, followed by refluxing in an oil bath at 100° C. for 4 hours. The reaction mixture was concentrated under reduced pressure, and concentrated hydrochloric acid (2 mL) was added thereto at room temperature, followed by stirring for 15 minutes. Subsequently, water (10 mL) was added to the reaction mixture, followed by washing with chloroform (20 mL). The pH of the obtained aqueous layer was adjusted to 12.0, and the resultant mixture was washed by chloroform (5 mL). The pH of the obtained aqueous layer was adjusted to 7.4, followed by extraction with chloroform (50 mL×3). The obtained organic layer was dried over anhydrous sodium sulfate, filtered, and concentrated under reduced pressure. The obtained residue was recrystallized from an ethanol-28% aqueous ammonia mixture (8:1), and dried under reduced pressure, to thereby yield the title compound as pale yellow crystals (125 mg, 60%).

mp: 211-214° C.

$^1$H-NMR (400 MHz, 0.1 mol/L NaOD) δ ppm: 0.09-0.18 (1H, m), 0.30-0.38 (1H, m), 0.43-0.52 (1H, m), 0.55-0.64 (1H, m), 0.73-0.83 (1H, m), 1.20 (1H, t, J=7.2 Hz), 1.32 (1H, J=8.1 Hz), 1.54-1.72 (2H, m), 3.33-3.43 (1H, m), 3.52 (1H, m), 3.59 (3H, s), 3.67 (2H, d, J=8.6 Hz), 3.76 (1H, t, J=8.3 Hz), 4.04-4.12 (1H, m), 4.84-5.06 (1H, m), 7.68 (1H, d, J=14.7 Hz), 8.49 (1H, s).

IR(ATR)ν cm$^{-1}$: 2954, 2885, 1988, 1610, 1568, 1523, 1495, 1454, 1377, 1356, 1288, 1267.

$[α]_D^{24.6}$ +126.60° (c0.407, 0.1 mol/L NaOH)

MS (EI) m/z: 420 (M+1)$^+$.

Anal.: Calcd for $C_{21}H_{23}F_2N_3O_4·0.5H_2O$: C, 58.87; H, 5.65; N, 9.81. Found: C, 58.81; H, 5.78; N, 9.42.

EXAMPLE 9

(3S)-10-[(3S,4S)-3-Amino-4-cyclopropylpyrrolidin-1-yl]-9-fluoro-2,3-dihydro-3-methyl-7-oxo-7H-pyrido[1,2,3-de][1,4]benzoxazine-6-carboxylic acid (Compound No. 9)

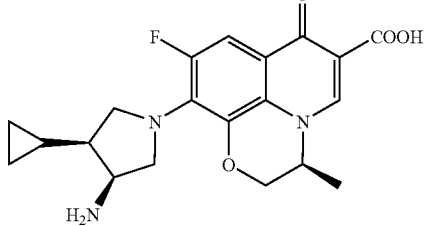

[F24]

(3S)-9,10-Difluoro-2,3-dihydro-3-methyl-7-oxo-7H-pyrido[1,2,3-de][1,4]benzoxazine-6-carboxylic acid difluoroboran complex (244 mg, 741 μmol) and triethylamine (206 μL, 1.48 mmol) were added to a solution of (3S,4S)-3-(tert-butoxycarbonyl)amino-4-cyclopropylpyrrolidine (167 mg, 741 μmol) in dimethyl sulfoxide (3 mL), and the resultant mixture was stirred at room temperature for 16 hours. (3S)-9,10-Difluoro-2,3-dihydro-3-methyl-7-oxo-7H-pyrido[1,2,3-de][1,4]benzoxazine-6-carboxylic acid difluoroboran complex (244 mg, 741 μmol) was further added thereto, followed by stirring for 3 hours. The reaction mixture was concentrated under reduced pressure, and ethanol (8 mL) and water (2 mL) were added thereto. Subsequently, triethylamine (2 mL) was added to the resultant mixture, followed by refluxing in an oil bath at 90° C. for 2 hours. The reaction mixture was concentrated under reduced pressure, and dissolved in chloroform (200 mL). The resultant solution was washed by a 10% aqueous citric acid solution (50 mL), and the obtained organic layer was dried over anhydrous sodium sulfate, filtered, and concentrated under reduced pressure. Subsequently, concentrated hydrochloric acid (10 mL) was added to the obtained yellow solid at room temperature, followed by stirring for 10 minutes. The reaction mixture was transferred to a separatory funnel with 1 mol/L hydrochloric acid (10 mL), followed by washing chloroform (50 mL×2). The pH of the obtained aqueous layer was adjusted to 12.0 with a 10 mol/L aqueous sodium hydroxide solution under cooling with ice. The pH was adjusted again to 7.4. The resultant mixture was extracted with chloroform (200 mL×3). The combined organic layer was dried over anhydrous sodium sulfate, filtered, concentrated under reduced pressure. The obtained residue was recrystallized from an ethanol-28% aqueous ammonia mixture (25:1), and dried under reduced pressure, to thereby yield the title compound as yellow crystals (130 mg, 45%).

mp: 218-220° C.
$^1$H-NMR (400 MHz, 0.1 mol/L NaOD) ppm: 0.15-0.29 (2H, m), 0.49-0.62 (2H, m), 0.77-0.88 (1H, m), 1.51 (3H, d, J=6.8 Hz), 1.47-1.54 (1H, m), 3.40-3.61 (2H, m), 3.67-3.73 (2H, m), 3.86-3.93 (1H, m), 4.28 (1H, d, J=11.5 Hz), 4.47 (1H, d, J=11.2 Hz), 4.54-4.61 (1H, m), 7.51 (1H, d, J=14.6 Hz) 8.31 (1H, s).
IR(ATR)ν cm$^{-1}$: 3043, 2983, 2875, 1705, 1618, 1525, 1444, 1396, 1350, 1323, 1279, 1209.
MS (EI) m/z: 388 (M+1)$^+$.
Anal.: Calcd for $C_{20}H_{22}FN_3O_4 \cdot 0.25H_2O$: C, 61.29; H, 5.79; N, 10.72; F, 4.85. Found: C, 61.20; H, 5.65; N, 10.78; F, 4.86.

REFERENTIAL EXAMPLE 11

(3S,4S)-1-Benzyloxycarbonyl-3-(tert-butoxycarbonyl)amino-4-carboxylpyrrolidine (3S,4S)-1-Benzyloxycarbonyl-3-(tert-butoxycarbonyl)amino-4-formylpyrrolidine (6.00 g, 12.0 mmol) was suspended in tertiary butyl alcohol (16 mL). Subsequently, 2-methyl-2-butene (12.7 mL, 120 mmol) was added to the suspension, and a suspension of sodium hypochlorite (1.09 g, 12.0 mmol) and sodium dihydrogenphosphate dihydrate (1.87 g, 12.0 mmol) in water (12 mL) was further added thereto, followed by stirring at room temperature for 12 hours. Under cooling with ice, 1 mol/L hydrochloric acid (80 mL) was added to the resultant mixture, and the obtained aqueous layer was extracted with diethyl ether (250 mL×2). The combined organic layer was washed sequentially by 5% aqueous sodium thiosulfate solution (80 mL) and saturated brine (80 mL), dried over anhydrous sodium magnesium, filtered, and concentrated under reduced pressure, to thereby yield (3S,4S)-1-benzyloxycarbonyl-3-(tert-butoxycarbonyl)amino-4-carboxylpyrrolidine as a colorless oily substance (7.10 g, quantitative amount). The product was employed, without further purification, in the subsequent step.
$^1$H-NMR (400 MHz, CDCl$_3$) δ ppm: 1.28 (9H, s), 3.25-3.30 (1H, m), 3.38-3.51 (1H, m), 3.67-3.78 (4H, m), 4.53-4.33 (1H, m), 5.12 (2H, s), 7.29-7.40 (5H, m).
MS (ESI) m/z: 265 (M-Boc)$^+$.

REFERENTIAL EXAMPLE 12

(3S,4S)-1-Benzyloxycarbonyl-3-(tert-butoxycarbonyl)amino-4-methoxycarbonylpyrrolidine The above-obtained crude (3S,4S)-1-benzyloxycarbonyl-3-(tert-butoxycarbonyl)amino-4-carboxylpyrrolidine (7.10 g, 12.0 mmol) was dissolved in a diethyl ether-dichloromethane solvent mixture (2:1) (150 mL). Subsequently, an excessive amount of a solution of diazomethane in diethyl ether (60 mL) was added to the solution, followed by stirring under cooling with ice for 10 minutes. After completion of the reaction, the reaction mixture was further stirred at room temperature for 2 hours, followed by concentration under reduced pressure. The obtained residue was recrystallized from a chloroform/n-hexane solvent mixture, and dried under reduced pressure, to thereby yield the title compound as colorless solid (3.37 g, 74%).
$^1$H-NMR (400 MHz, CDCl$_3$) δ ppm: 1.43 (9H, s), 3.19-3.28 (1H, m), 3.38-3.49 (1H, m), 3.67-3.79 (7H, m), 4.49 (1H, brs), 5.11-5.15 (2H, m), 7.31-7.40 (5H, m).
MS (ESI) m/z: 279 (M-Boc)$^+$.

REFERENTIAL EXAMPLE 13

(3S)-1-Benzyloxycarbonyl-3-(tert-butoxycarbonyl)amino-4-(1-hydroxy-1-methyl)ethylpyrrolidine (4-position isomer mixture)

(3S,4S)-1-Benzyloxycarbonyl-3-(tert-butoxycarbonyl)amino-4-methoxycarbonylpyrrolidine (1.00 g, 2.64 mmol) was dissolved in tetrahydrofuran (20 mL), and a solution of methylmagnesium bromide in tetrahydrofuran (1.00 mol/L, 8.71 mL, 8.71 mmol) was added dropwise to the solution under a nitrogen atmosphere at −10° C. over 10 minutes. After stirring of the resultant mixture at the same temperature for 10 minutes, a saturated aqueous ammonium chloride solution (20 mL) was added thereto, followed by stirring for 0.5 hours. The obtained aqueous layer was extracted with diethyl ether (50 mL×2). The obtained organic layer was washed by saturated brine (40 mL), dried over anhydrous sodium magnesium, filtered, and concentrated under reduced pressure. The obtained residue was purified through short silica gel column chromatography (ethyl acetate:n-hexane=1:2 to 1:1), to thereby yield the title compound (4-position isomer mixture) as a colorless oily substance (1.00 g, quantitative amount). The product was employed, without further purification, in the subsequent step.

$^{1}$H-NMR (400 MHz, CDCl$_{3}$) δ ppm: 1.24-1.28 (3H, m), 1.37 (3H, s), 1.44 (9H, s), 1.99-2.03 (1H, m), 2.13-2.21 (1H, m), 3.41-3.77 (4H, m), 4.09-4.18 (1H, m), 5.10-5.18 (2H, m), 7.29-7.41 (5H, m).

MS (ESI) m/z: 279 (M-Boc)$^{+}$.

REFERENTIAL EXAMPLE 14

(3S)-1-(Benzyloxycarbonyl)-3-(tert-butoxycarbonyl) amino-4-isopropenylpyrrolidine (4-position isomer mixture)

The above-obtained crude (3S)-1-benzyloxycarbonyl-3-(tert-butoxycarbonyl)amino-4-(1-hydroxy-1-methyl)ethylpyrrolidine (4-position isomer mixture) (1.00 g, 2.64 mmol) was dissolved in dichloromethane (20 mL). Subsequently, under cooling with ice, triethylamine (1.47 mL, 10.6 mmol), 4-dimethylaminopyridine (1.29 g, 10.6 mmol), and methanesulfonyl chloride (817 μL, 10.6 mmol) were added to the solution, followed by stirring at room temperature for 12 hours. Under cooling with ice, a saturated aqueous ammonium chloride solution (20 mL) was added to the resultant mixture, and the obtained aqueous layer was extracted with ethyl acetate (50 mL×2). The combined organic layer was washed by saturated brine (40 mL), and dried over anhydrous sodium sulfate. After filtration, the filtrate was concentrated under reduced pressure, and the obtained residue was purified through silica gel column chromatography (ethyl acetate:n-hexane=1:4 to 1:1), to thereby yield the title compound (4-position isomer mixture) as a colorless oily substance (450 mg, 47%).

$^{1}$H-NMR (400 MHz, CDCl$_{3}$) δ: 1.44 (9H, s), 1.57 (3H, d, J=0.5 Hz), 1.75-1.77 (2H, m), 3.55 (1H, dd, J=5.1, 12.0 Hz), 3.76 (1H, d, J=11.8 Hz), 3.96 (1H, d, J=13.2 Hz), 4.06-4.16 (1H, m), 4.63 (2H, s), 5.15 (2H, s), 7.34-7.39 (5H, m).

MS (ESI) m/z: 261 (M-Boc)$^{+}$.

REFERENTIAL EXAMPLE 15

(3S)-3-(tert-Butoxycarbonyl)amino-4-isopropylpyrrolidine(4-position isomer mixture)

A 10% palladium carbon catalyst (300 mg) was added to a solution of (3S)-1-benzyloxycarbonyl-3-(tert-butoxycarbonyl)amino-4-isopropenylpyrrolidine (300 mg, 832 μmol) in methanol (10 mL), and the resultant mixture was stirred in a hydrogen atmosphere under an ordinary pressure for 2 hours. After filtration, a 10% palladium carbon catalyst (300 mg) was added again to the filtrate, followed by stirring in a hydrogen atmosphere under an ordinary pressure for 1 hour. After filtration, the filtrate was concentrated under reduced pressure, to thereby yield (3S)-3-(tert-butoxycarbonyl)amino-4-isopropylpyrrolidine as a colorless amorphous (172 mg, quantitative amount).

MS (ESI+) m/z: 229 (M+1)$^{+}$.

EXAMPLE 10

(3S)-10-[(3S)-3-Amibo-4-isopropropyl-1-pyrrolidinyl]-9-fluoro-2,3-dihydro-3-methyl-7-oxo-7H-pyrido[1,2,3-de][1,4]benzoxazine-6-carboxylic acid (isomer A: Compound No. 10-A) and (isomer B: Compound No. 10-B)

[F25]

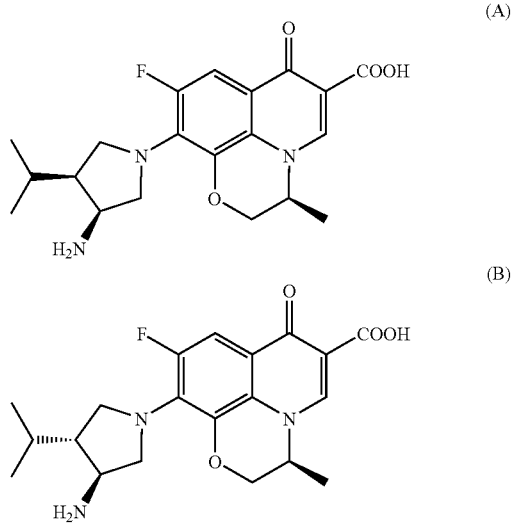

(3S)-9,10-Difluoro-2,3-dihydro-3-methyl-7-oxo-7H-pyrido[1,2,3-de][1,4]benzoxazine-6-carboxylic acid difluoroboran complex (247 mg, 752 μmol) and triethylamine (126 μL, 902 μmol) were added to a solution of (3S)-3-(tert-butoxycarbonyl)amino-4-isopropylpyrrolidine (172 mg, 752 μmol) in dimethyl sulfoxide (2 mL), and the resultant mixture was stirred at room temperature for 20 hours. The reaction mixture was concentrated under reduced pressure, and ethanol (50 mL), water (2 mL), and triethylamine (1 mL) were added thereto, followed by refluxing in an oil bath at 100° C. for 4 hours. The reaction mixture was concentrated under reduced pressure, and dissolved in ethyl acetate (100 mL×2). The solution was washed sequentially by a 10% aqueous citric acid solution (100 mL) and saturated brine (50 mL). The obtained organic layer was dried over anhydrous sodium sulfate, filtered, and concentrated under reduced pressure. Subsequently, concentrated hydrochloric acid (5 mL) was added to the obtained yellow solid under cooling with ice, and the mixture was stirred at room temperature for 10 minutes. The reaction mixture was transferred to a separatory funnel with 1 mol/L hydrochloric acid (10 mL), followed by washing with chloroform (100 mL×4). The pH of the obtained aqueous layer was adjusted to 12.0 with a 10 mol/L aqueous sodium hydroxide solution under cooling with ice. The pH was adjusted again to 7.4 with concentrated hydrochloric acid and 1 mol/L hydrochloric acid, and the resultant mixture was extracted with chloroform (150 mL×3). The combined organic layer was dried over anhydrous sodium sulfate, filtered, and concentrated under reduced pressure, to thereby yield a crude mixture of isomer A and isomer B (about, 1:4). The crude mixture was subjected to separation and purification through preparative chromatography (chloroform:methanol:water=7:3:1, developer), recrystallization from ethanol, and drying under reduced pressure, to thereby obtain isomer A (48.5 mg, 17%, a low polar compound) and isomer B (90.5 mg, 31%, a high polar compound), both being in the form of yellow crystals.

Isomer A;
mp: 249-251° C.
$^1$H-NMR (400 MHz, 0.1 mol/L NaOD) δ ppm: 0.93 (3H, d, J=6.6 Hz), 1.00 (3H, d, J=6.4 Hz), 1.52 (3H, d, J=6.9 Hz), 1.66-1.86 (1H, m), 3.34 (1H, dd, J=11.0, 1.2 Hz), 3.49-3.54 (2H, m), 3.73 (1H, td, J=10.3, 2.7 Hz), 4.08 (1H, dt, J=10.6, 3.9 Hz), 4.26 (1H, dd, J=11.3, 2.5 Hz), 4.46 (1H, dd, J=11.4, 1.8 Hz), 4.55-4.61 (1H, m), 7.52 (1H, d, J=14.5 Hz), 8.31 (1H, s).
IR(ATR)ν cm$^{-1}$: 3383, 3317, 2947, 2889, 1716, 1618, 1535, 1437, 1398, 1346, 1315, 1284, 1232.
MS (ESI+) m/z: 390 (M+1)$^+$.
Anal. Calcd for $C_{20}H_{24}FN_3O_4 \cdot 0.25H_2O$: C, 60.98; H, 6.27; N, 10.67; F, 4.82. Found: C, 61.17; H, 6.19; N, 10.63; F, 4.96.

Isomer B;
mp: 202-205° C.
$^1$H-NMR (400 MHz, 0.1 mol/L NaOD) δ ppm: 0.93 (3H, d, J=6.1 Hz), 1.01 (3H, d, J=6.4 Hz), 1.19 (1H, t, J=7.1 Hz), 1.50 (3H, d, J=6.9 Hz), 1.76-1.84 (2H, m), 3.28 (1H, q, J=6.7 Hz), 3.41-3.48 (2H, m), 3.58-3.68 (3H, m), 4.32 (1H, dd, J=11.4, 2.3 Hz), 4.48 (1H, dd, J=11.3, 2.0 Hz), 4.55-4.61 (1H, m), 7.51 (1H, d, J=14.2 Hz), 8.32 (1H, s).
IR(ATR)ν cm$^{-1}$: 2958, 2871, 1720, 1616, 1576, 1522, 1444, 1383, 1340, 1257, 1213.
MS (ESI+) m/z: 390 (M+1)$^+$.
Anal: Calcd for $C_{20}H_{24}FN_3O_4 \cdot 0.5EtOH \cdot 0.75H_2O$: C, 59.21; H, 6.74; N, 9.86; F, 4.46. Found: C, 59.30; H, 6.53; N, 9.99; F, 4.56.

REFERENTIAL EXAMPLE 16

(3S)-1-Benzyloxycarbonyl-3-(tert-butoxycarbonyl) amino-4-formylpyrrolidine

Dimethyl sulfoxide (5.10 mL, 59.3 mmol) was added to a solution of oxalylchloride (5.00 mL, 57.3 mmol) in dichloromethane (100 mL), and the mixture was stirred at −78° C. for 20 minutes. Subsequently, a solution of (3S,4S)-1-benzyloxycarbonyl-3-(tert-butoxycarbonyl)amino-4-hydroxymethylpyrrolidine (8.00 g, 22.8 mmol) in dichloromethane (85 mL) was added dropwise slowly thereto, followed by stirring at the same temperature for 30 minutes, and further at −43° C. for 1 hour. Subsequently, triethylamine (30 mL) was added thereto, and the temperature of the resultant mixture was elevated to an ice cooling temperature, followed by stirring for 45 minutes. Thereafter, a 10% aqueous citric acid solution (100 mL) was added to the resultant mixture, followed by stirring for 10 minutes. The obtained aqueous layer was extracted with dichloromethane (200 mL×2). The combined organic layer was washed by saturated brine (100 mL), and dried over anhydrous sodium sulfate. After filtration, the filtrate was concentrated under reduced pressure, to thereby yield a crude aldehyde as a pale yellow oily substance. Subsequently, triethylamine (0.50 mL, 3.59 mmol) was added to a solution of the crude aldehyde compound (2.5 g, 7.18 mmol) in dichloromethane (10 mL). The resultant mixture was stirred at room temperature for 24 hours, and triethylamine (0.50 mL, 3.59 mmol) was further added thereto, followed by stirring for another 24 hours. Thereafter, silica gel (100 g) was added to the reaction mixture, followed by stirring for 24 hours. The reaction mixture was concentrated under reduced pressure, and left to stand for 24 hours. The residue was purified through silica gel column chromatography (ethyl acetate:n-hexane=7:3), to thereby yield the title compound (an isomer mixture of (4S)-form and (4R)-form (1:3)) as a colorless oily substance (750 mg, 28%).

$^1$H-NMR (400 MHz, CDCl$_3$) δ ppm: 1.42 (9×1/4H, s), 1.44 (9×3/4H, s), 2.90-3.93 (5H, m), 4.40-5.30 (4H, m), 7.24-7.50 (5H, m), 9.71 (1×3/4H, s), 9.77 (1H×1/4, s).
MS (ESI) m/z: 249 (M-Boc)$^+$.

REFERENTIAL EXAMPLE 17

(3S)-1-Benzyloxycarbonyl-3-(tert-butoxycarbonyl) amino-4-vinylpyrrolidine

Butyl lithium (3.56 mL, 1.58 M, toluene solution) was added dropwise under cooling with ice to a suspension of methyltriphenylphosphonium bromide (2.15 g, 6.03 mmol) in tetrahydrofuran (20 mL), followed by stirring at room temperature for 20 minutes, and further at 40° C. for 5 minutes. Subsequently, a solution of (3S)-1-benzyloxycarbonyl-3-(tert-butoxycarbonyl)amino-4-formylpyrrolidine [an isomer mixture of (4S)-form: (4R)-form (1:3)] (700 mg, 2.01 mmol) in tetrahydrofuran (7.0 mL) was added under cooling with ice to the resultant mixture, followed by stirring at room temperature for 10 hours. The reaction mixture was poured to a 10% aqueous citric acid solution (20 mL), and the resultant mixture was diluted with ethyl acetate (100 mL). The obtained aqueous layer was extracted with ethyl acetate (100 mL×2). The combined organic layer was washed sequentially by saturated sodium hydrogencarbonate (100 mL) and saturated brine (100 mL), and dried over anhydrous sodium sulfate. After filtration, the filtrate was concentrated under reduced pressure. The obtained residue was purified through silica gel column chromatography (ethyl acetate:n-hexane=1:4), to thereby yield the title compound (an isomer mixture of (4S)-form and (4R)-form (1:4)) as a colorless oily substance (250 mg, 36%).

$^1$H-NMR (400 MHz, CDCl$_3$) ppm: 1.43 (9H, s), 2.50-2.75 (1×4/5H, m), 2.89-3.02 (1×1/5H, m), 3.05-3.48 (2H, m), 3.56-4.01 (3H, m), 4.25 (1×1/5H, s), 4.53 (1×4/5H, s), 5.06-5.30 (4H, m), 5.65-5.84 (1H, m), 7.28-7.40 (5H, m).
MS (ESI+) m/z: 347 (M+1)$^+$.

REFERENTIAL EXAMPLE 18

(3S)-3-(tert-Butoxycarbonyl)amino-4-ethylpyrrolidine

A 10% palladium carbon catalyst (15 mg) was added to a solution of (3S)-1-benzyloxycarbonyl-3-(tert-butoxycarbonyl)amino-4-vinylpyrrolidine [an isomer mixture of (4S)-form: (4R)-form (1:4)] (230 mg, 0.66 mmol) in ethanol (8 mL), followed by stirring in a hydrogen atmosphere under an ordinary pressure at room temperature for 12 hours. After filtration, the filtrate was concentrated under reduced pressure, to thereby yield the title compound (an isomer mixture of (4S)-form and (4R)-form (1:4)) as a colorless oily substance (148 mg, 100%).

$^1$H-NMR (400 MHz, CDCl$_3$) δ ppm: 0.94 (3H, t, J=7.4 Hz), 1.20-1.80 (3H, m), 1.44 (9H, s), 1.90-2.20 (1H, m), 2.50-2.59 (1H, m), 2.76 (1×4/5H, dd, J=4.4, 11.3 Hz), 2.79 (1×1/5H, dd, J=3.1, 11.1 Hz), 3.12-3.24 (2H, m), 3.71 (1H, s), 4.17 (1×1/5H, brs), 4.77 (1×4/5H, brs).
MS (ESI) m/z: 215 (M+1)+.

EXAMPLE 11

(3S)-10-[(3S,4R)-3-Amino-4-ethylpyrrolidin-1-yl]-9-fluoro-2,3-dihydro-3-methyl-7-oxo-7H-pyrido[1,2,3-de][1,4]benzoxazine-6-carboxylic acid (Compound No. 11)

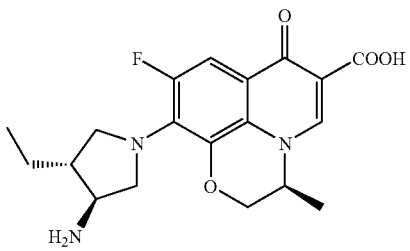

[F26]

(3S)-9,10-Difluoro-2,3-dihydro-3-methyl-7-oxo-7H-pyrido[1,2,3-de][1,4]benzoxazine-6-carboxylic acid difluoroboran complex (223 mg, 676 μmol) and triethylamine (113 μL, 812 μmol) were added to a solution of (3S)-3-(tert-butoxycarbonyl)amino-4-ethylpyrrolidine (145 mg, 676 μmol) in dimethyl sulfoxide (3 mL), and the resultant mixture was stirred at room temperature for 16 hours. Subsequently, water (10 mL) was added to the reaction mixture, and precipitated crystals were collected through filtration. The thus-collected crystals were suspended in a mixture of ethanol (10 mL) and water (2 mL), and triethylamine (3 mL) was added thereto, followed by refluxing in an oil bath at 90° C. for 5 hours. The reaction mixture was concentrated under reduced pressure, and dissolved in chloroform (100 mL). The solution was washed by a 10% aqueous citric acid solution (30 mL). The obtained organic layer was dried over anhydrous sodium sulfate, filtered, and concentrated under reduced pressure. Subsequently, concentrated hydrochloric acid (5 mL) was added to the obtained yellow solid under cooling with ice, followed by stirring for 30 minutes. The reaction mixture was transferred to a separatory funnel with 4 mol/L hydrochloric acid (4 mL), followed by washing by chloroform (50 mL×7). The pH of the obtained aqueous layer adjusted to 12.0 with a 10 mol/L aqueous sodium hydroxide solution under cooling with ice. The pH was adjusted again to 7.4, and the resultant mixture was extracted with chloroform (70 mL×3). The combined organic layer was dried over anhydrous sodium sulfate, filtered, and concentrated under reduced pressure. The obtained residue was purified through preparative chromatography (chloroform:methanol:water=7:3:1, developer), recrystallized from ethanol, and dried under reduced pressure, to thereby yield the title compound as yellow crystals (80 mg, 31%).

$^1$H-NMR (400 MHz, 0.1 mol/L NaOD) δ ppm: 0.96 (3H, t, J=7.5 Hz), 1.27-1.38 (1H, m), 1.51 (3H, d, J=6.9 Hz), 1.65-1.76 (1H, m), 1.79-1.91 (1H, m), 3.12 (1H, q, J=7.4 Hz), 3.37-3.48 (2H, m), 3.71 (2H, dd, J=16.3, 7.0 Hz), 4.32 (1H, dd, J=2.5, 11.8 Hz), 4.48 (1H, dd, J=2.2, 11.8 Hz), 4.55-4.63 (1H, m), 7.52 (1H, d, J=14.0 Hz), 8.32 (1H, s).
mp: 189-191° C.
IR(ATR)ν cm$^{-1}$: 2978, 2937, 2875, 1718, 1614, 1572, 1522, 1462, 1379, 1325, 1254, 1207.
$[\alpha]_D^{24.8}$ −43.52° (c0.125, 0.1 mol/L NaOH).
MS (ESI) m/z: 376 (M+1)+.
Anal.: Calcd for $C_{19}H_{22}FN_3O_4 \cdot 0.5H_2O$: C, 59.37; H, 6.03; N, 10.93; F, 4.94. Found: C, 59.33; H, 5.95; N, 10.95; F, 4.93.

REFERENTIAL EXAMPLE 19

(3S,4S)-1-Benzyloxycarbonyl-3-(N-tert-butoxycarbonyl-N-methyl)amino-4-ethylpyrrolidine (3S,4S)-1-Benzyloxycarbonyl-3-(tert-butoxycarbonyl)amino-4-ethylpyrrolidine (1.00 g, 2.87 mmol) was added to a suspension of sodium hydride (250 mg, 5.74 mmol) in dimethylformamide (14.4 mL), and the resultant mixture was stirred under cooling with ice for 1 hour. Subsequently, methyl iodide (715 μL, 11.5 mmol) was added to the reaction mixture under cooling with ice, followed by stirring at room temperature for 17 hours. After the reaction mixture was cooled on ice, a saturated aqueous ammonium chloride solution (30 mL) and water (50 mL) were added thereto, followed by extraction with ethyl acetate (200 mL×2). The combined organic layer was washed sequentially by water (100 mL) and saturated brine (100 mL), and obtained organic layer was dried over anhydrous sodium sulfate. After filtration, the filtrate was concentrated under reduced pressure. The obtained residue was purified through silica gel column chromatography (ethyl acetate:n-hexane=1:4 to 1:2), to thereby yield the title compound as a colorless oily substance (989 mg, 95%).
$[\alpha]_D^{23.7}$ +37.58° (c1.40, CHCl$_3$).
$^1$H-NMR (400 MHz, CDCl$_3$) δ ppm: 0.94 (3H, dt, J=6.1, 7.3 Hz), 1.19-1.33 (1H, m), 1.41-1.55 (2H, m), 1.46 (9H, d, J=3.4 Hz), 2.17-2.33 (1H, m), 2.75 (3H, s), 3.02-3.13 (1H, m), 3.55-3.77 (3H, m), 5.09-5.19 (2H, m), 7.27-7.38 (5H, m).
MS (EI) m/z: 363 (M+1)+.

REFERENTIAL EXAMPLE 20

(3S,4S)-3-(N-tert-Butoxycarbonyl-N-methyl)amino-4-ethylpyrrolidine

A 10% palladium carbon catalyst (95.2 mg) was added to a solution of (3S,4S)-1-benzyloxycarbonyl-3-(N-tert-butoxycarbonyl-N-methyl)amino-4-ethylpyrrolidine (952 mg, 2.63 mmol) in methanol (26 mL), and the resultant mixture was stirred in a hydrogen atmosphere under an ordinary pressure at room temperature for 1 hour. After filtration, the filtrate was concentrated under reduced pressure, to thereby yield the title compound as a colorless oily substance (600 mg, 100%). The product was employed, without further purification, in the subsequent step.
$^1$H-NMR (400 MHz, CDCl$_3$) δ ppm: 0.93 (3H, t, J=7.4 Hz), 1.12-1.27 (1H, m), 1.46 (9H, s), 1.46-1.50 (2H, m), 2.03-2.05 (1H, m), 2.59 (1H, t, J=10.4 Hz), 2.83 (3H, s), 3.01 (1H, dd, J=4.3, 12.1 Hz), 3.20 (1H, dd, J=8.06, 11.0 Hz), 3.23-3.31 (1H, m).
MS (EI) m/z: 229 (M+1)+.

EXAMPLE 12

7-[(3S,4S)-3-Ethyl-4-methylaminopyrrolidin-1-yl]-6-fluoro-1-[(1R,2S)-2-fluorocyclopropyl]-8-methoxy-1,4-dihydro-4-oxoquinoline-3-carboxylic acid (Compound No. 12)

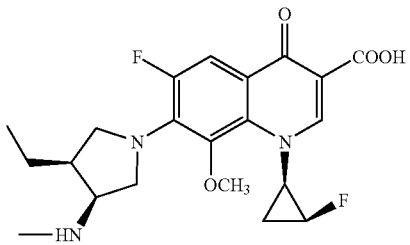

[F27]

6,7-Difluoro-1-[(1R,2S)-2-fluorocyclopropyl]-8-methoxy-1,4-dihydro-4-oxoquinoline-3-carboxylic acid difluoroboran complex (142 mg, 394 μmol) and triethylamine (65.8 μL, 472 μmol) were added to a solution of (3S,4S)-3-(N-tert-butoxycarbonyl-N-methyl)amino-4-ethylpyrrolidine (99.0 mg, 434 μmol) in dimethyl sulfoxide (2 mL), and the resultant mixture was stirred at room temperature for 24 hours. The reaction mixture was concentrated, and ethanol (20 mL) and water (1 mL) were added thereto for dissolving. Subsequently, triethylamine (2 mL) was added to the solution, followed by refluxing in an oil bath at 90° C. for 2 hours. The reaction mixture was concentrated under reduced pressure, and dissolved in chloroform (100 mL). The solution was washed by a 10% aqueous citric acid solution (30 mL). The obtained organic layer was dried over anhydrous sodium sulfate, filtered, and concentrated under reduced pressure. Subsequently, concentrated hydrochloric acid (4 mL) was added so as to dissolve the obtained yellow solid at room temperature, and water (20 mL) was added to the solution, followed by washing by chloroform (80 mL×3). The pH of the obtained aqueous layer was adjusted to 12.0 with a 10 mol/L aqueous sodium hydroxide solution under cooling with ice. The pH was adjusted to 7.4. The resultant mixture was extracted with chloroform (80 mL×2). The combined organic layer was dried over anhydrous sodium sulfate, filtered, and concentrated under reduced pressure. The obtained residue was recrystallized from ethanol, and dried under reduced pressure, to thereby yield the title compound as yellow crystals (77.0 mg, 45%).

mp: 143-145° C.

$^1$H-NMR (400 MHz, 0.1 mol/L NaOD) δ ppm: 0.97 (3H, t, J=7.3 Hz), 1.30-1.66 (4H, m), 2.21-2.30 (1H, m), 2.34 (3H, s), 3.23-3.30 (1H, m), 3.48-3.59 (5H, m), 3.63-3.80 (2H, m), 4.00-4.07 (1H, m), 4.98 (1H, d, J=64.5 Hz), 7.65 (1H, d, J=14.6 Hz), 8.43 (1H, s).

IR(ATR)ν cm$^{-1}$: 3045, 2964, 2871, 1728, 1649, 1614, 1577, 1493, 1439, 1383, 1346, 1311, 1290, 1255, 1201.

MS (EI) m/z: 422 (M+1)$^+$.

Anal.: Calcd for $C_{21}H_{25}F_2N_3O_4 \cdot 0.75H_2O$: C, 57.99; H, 6.14; N, 9.66; F, 8.74. Found: C, 57.83; H, 6.05; N, 9.38; F, 8.58.

EXAMPLE 13

(3S)-10-[(3S,4S)-3-Ethyl-4-methylaminopyrrolidin-1-yl]-9-fluoro-2,3-dihydro-3-methyl-7-oxo-7H-pyrido[1,2,3-de][1,4]benzoxazine-6-carboxylic acid (Compound No. 13)

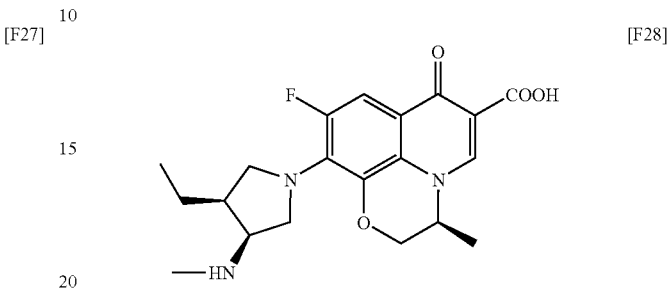

[F28]

(3S)-9,10-Difluoro-2,3-dihydro-3-methyl-7-oxo-7H-pyrido[1,2,3-de][1,4]benzoxazine-6-carboxylic acid difluoroboran complex (118 mg, 358 μmol) and triethylamine (60.0 μL, 430 μmol) were added to a solution of (3S,4S)-3-(N-tert-butoxycarbonyl-N-methyl)amino-4-ethylpyrrolidine (90.0 mg, 394 μmol) in dimethyl sulfoxide (2 mL), and the resultant mixture was stirred at room temperature for 15 hours. The reaction mixture was concentrated under reduced pressure, and ethanol (19 mL) and water (1 mL) were added thereto for dissolving. Subsequently, triethylamine (2 mL) was added to the solution, followed by refluxing in an oil bath at 90° C. for 4 hours. The reaction mixture was concentrated under reduced pressure, and dissolved in chloroform (100 mL). The solution was washed by a 10% aqueous citric acid solution (50 mL). The obtained organic layer was dried over anhydrous sodium sulfate, filtered, and concentrated under reduced pressure. Thereafter, concentrated hydrochloric acid (6 mL) was added to the obtained yellow solid, and the resultant mixture was transferred to a separatory funnel with water (20 mL), followed by washing by chloroform (100 mL×2). The pH of the obtained aqueous layer was adjusted to 11.0 with a 10 mol/L aqueous sodium hydroxide solution under cooling with ice. The pH was adjusted again to 7.4. The resultant mixture was extracted with chloroform (100 mL×3). The combined organic layer was dried over anhydrous sodium sulfate, filtered, and concentrated under reduced pressure. The obtained residue was recrystallized from ethanol, and dried under reduced pressure, to thereby yield the title compound as pale yellow crystals (89.0 mg, 64%).

mp: 211-213° C.

$^1$H-NMR (400 MHz, 0.1 mol/L NaOD) ppm: 0.95 (3H, t, J=7.2 Hz), 1.30-1.43 (1H, m), 1.46-1.55 (1H, m), 1.49 (3H, d, J=6.6 Hz), 2.10-2.23 (1H, m), 2.31 (3H, s), 3.14-3.23 (1H, m), 3.49-3.65 (3H, m), 3.74-3.85 (1H, m), 4.26 (1H, d, J=11.7 Hz), 4.43 (1H, d, J=11.2 Hz), 4.51-4.60 (1H, m), 7.46 (1H, d, J=14.4 Hz), 8.29 (1H, s).

IR(ATR)ν cm$^{-1}$: 2873, 1705, 1620, 1525, 1464, 1444, 1394, 1352, 1321, 1292, 1207, 1184.

MS (EI) m/z: 390 (M+1)$^+$.

Anal.: Calcd for $C_{20}H_{24}FN_3O_4$: C, 61.68; H, 6.21; N, 10.79; F, 4.88. Found: C, 61.27; H, 6.16; N, 10.69; F, 4.85.

REFERENTIAL EXAMPLE 21

(3S,4S)-1-Benzyloxycarbonyl-3-(tert-butoxycarbonyl)amino-4-(phenylsulfanil)methylpyrrolidine A solution of (3S,4S)-1-benzyloxycarbonyl-3-(tert-butoxycarbonyl)amino-4-hydroxymethylpyrrolidine (7.55 g, 21.55 mmol), diphenyldisulfide (6.55 g, 30 mmol), and tributylphosphine (9.97 mL, 40 mmol) in tetrahydrofuran (100 mL) was refluxed under a nitrogen atmosphere for 1 hour. The temperature of the resultant mixture was cooled to room temperature. Subsequently, a 1 mol/L aqueous sodium hydroxide solution was added to the mixture, followed by extraction with diethyl ether (200 mL×3). The combined organic layer was washed sequentially with water (100 mL) and saturated brine (100 mL). The thus-washed organic layer was dried over anhydrous sodium magnesium, filtered, and concentrated under reduced pressure. The obtained residue was purified through silica gel column chromatography (n-hexane:ethyl acetate=4:1), to thereby yield the title compound as a colorless oily substance (7.97 g, 83.6%).

$^1$H-NMR (400 MHz, CDCl$_3$) δ ppm: 1.45 (9H, s), 2.44-2.58 (1H, m), 2.70-2.80 (1H, m), 3.16-3.22 (2H, m), 3.37-3.44 (1H, m), 3.59 (1H, dd, J=5.5, 11.5 Hz), 3.67-3.78 (1H, m), 4.25-4.32 (1H, m), 4.64 (1H, br), 5.11 (2H, s), 7.18-7.24 (1H, m), 7.26-7.36 (9H, m).

IR(ATR)ν cm$^{-1}$: 3319, 2976, 1684, 1522, 1417, 1363, 1243, 1160, 737, 692.

HRMS (EI) m/z: Calcd for C$_{24}$H$_{30}$O$_4$N$_2$S: 442.1926. Found: 442.1904.

REFERENTIAL EXAMPLE 22

(3S,4S)-3-(tert-Butoxycarbonyl)amino-4-methylpyrrolidine

A suspension of (3S,4S)-1-benzyloxycarbonyl-3-(tert-butoxycarbonyl)amino-4-(phenylsulfanil)methylpyrrolidine (7.97 g, 18.01 mmol) and Raney nickel (R100) (50 mL) in ethanol (150 mL) was stirred in a hydrogen atmosphere under an ordinary pressure at an external temperature of 50° C. for 18 hours. The temperature of the resultant mixture was cooled to room temperature. Thereafter, insoluble matter was removed through filtration by use of Celite, and the filtrate was concentrated under reduced pressure. The obtained residue was dissolved in ethanol (100 mL), and a 10% palladium carbon catalyst (2.0 g) was added to the solution, followed by stirring in a hydrogen atmosphere under an ordinary pressure at room temperature for 3 hours. After insoluble matter was removed through filtration by use of Celite, the filtrate was concentrated under reduced pressure. The obtained residue was dissolved in diethyl ether. The solution was washed by a 1 mol/L aqueous sodium hydroxide solution, dried over anhydrous sodium sulfate, filtered, concentrated under reduced pressure, and dried under reduced pressure, to thereby yield the title compound as colorless crystals (2.602 g, 72.1%).

$^1$H-NMR (400 MHz, CDCl$_3$) ppm: 0.97 (3H, d, J=7.0 Hz), 1.45 (9H, s), 1.79 (1H, br), 2.21-2.28 (1H, m), 2.48 (1H, dd, J=8.5, 10.5), 2.70 (1H, dd, J=4.5, 11.0 Hz), 3.15 (1H, dd, J=8.0, 10.5 Hz), 3.25 (1H, dd, J=6.5, 11.0 Hz), 4.10 (1H, br), 4.63 (1H, br).

IR(ATR)ν cm$^{-1}$: 3365, 3217, 2956, 1678, 1520, 1365, 1244, 1167, 1061, 906, 627.

MS (FAB) m/z (%): 201 (93, M$^+$+1), 145 (100, M$^+$−55), 101 (8, M$^+$−99).

HRMS (FAB) m/z: Calcd for C$_{10}$H$_{21}$O$_2$N$_2$: 201.1603. Found: 201.1602.

REFERENTIAL EXAMPLE 23

7-[(3S,4S)-3-Amino-4-methylpyrrolidin-1-yl]-6-fluoro-1-[(1R,2S)-2-fluorocyclopropyl]-1,4-dihydro-8-methoxy-4-oxoquinoline-3-carboxylic acid-hydrochloride (Comparative Compound A)

[F29]

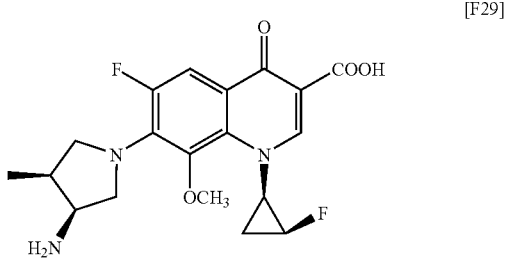

6,7-Difluoro-1-[(1R,2S)-2-fluorocyclopropyl]-8-methoxy-1,4-dihydro-4-oxoquinoline-3-carboxylic acid difluoroboran complex (1.44 g, 4.00 mmol) and triethylamine (2 mL) were added to a solution of (3S,4S)-3-(tert-butoxycarbonyl)amino-4-methylpyrrolidine (841 mg, 4.20 mmol) in dimethyl sulfoxide (6 mL), and the resultant mixture was stirred at room temperature for 16 hours. The reaction mixture was concentrated under reduced pressure. Subsequently, water was added to the obtained residue, and precipitated crystals were collected through filtration. Thereafter, 90% ethanol (100 mL) and triethylamine (20 mL) were added to the obtained crystals, followed by refluxing for 3 hours. The temperature of the resultant mixture was cooled to room temperature. The reaction mixture was concentrated under reduced pressure. The obtained residue was dissolved in chloroform (200 mL). The solution was washed sequentially by a 10% aqueous citric acid solution (100 mL) and saturated brine (50 mL), dried over anhydrous sodium sulfate, filtered, and concentrated under reduced pressure. The obtained residue was dissolved in concentrated hydrochloric acid, and the solution was washed by chloroform (50 mL). Subsequently, water was added thereto, and precipitated crystals were collected through filtration. The obtained crystals were recrystallized from ethanol, to thereby yield the title compound as yellow crystals (900 mg, 50.3%).

mp: 246-247° C.

$^1$H-NMR (400 MHz, D$_2$O) δ ppm: 1.12 (3H, d, J=7.0 Hz), 1.35-1.48 (1H, m), 1.48-1.60 (1H, m), 2.63-2.70 (1H, m), 3.42-3.48 (1H, m), 3.45 (3H, s), 3.60-3.63 (1H, m), 3.70 (1H, t, J=9.0 Hz), 3.91-3.99 (3H, m), 4.86-5.04 (1H, m), 6.69 (1H, d, J=14.0 Hz), 8.48 (1H, s).

IR(ATR)ν cm$^{-1}$: 2968, 2879, 2805, 1701, 1618, 1510, 1452, 1317, 1176, 1043, 927, 804.

Anal.: Calcd for C$_{18}$H$_{20}$FN$_3$O$_4$.HCl.H$_2$O: C, 50.95; H, 5.40; N, 9.38; F, 8.48; Cl, 7.92. Found: C, 51.02; H, 5.69; N, 9.14; F, 8.32; Cl, 7.77.

REFERENTIAL EXAMPLE 24

(3S)-10-[(3S,4S)-3-Amino-4-methylpyrrolidin-1-yl]-9-fluoro-2,3-dihydro-3-methyl-7-oxo-7H-pyrido[1,2,3-de][1,4]benzoxazine-6-carboxylic acid-hydrochloride (Comparative Compound B)

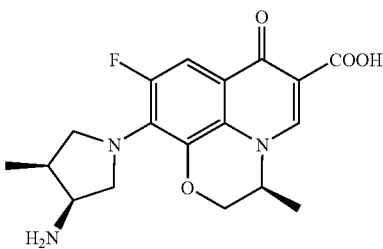

[F30]

(3S)-9,10-Difluoro-2,3-dihydro-3-methyl-7-oxo-7H-pyrido[1,2,3-de][1,4]benzoxazine-6-carboxylic acid difluoroboran complex (1.97 g, 6.00 mmol) and triethylamine (5 mL) were added to a solution of (3S,4S)-3-(tert-butoxycarbonyl)amino-4-methylpyrrolidine (1.30 g, 6.50 mmol) in dimethyl sulfoxide (25 mL), and the resultant mixture was stirred at room temperature for 7 days. The reaction mixture was concentrated under reduced pressure. Subsequently, water was added to the residue, and precipitated crystals were collected through filtration. Thereafter, 90% ethanol (100 mL) and triethylamine (20 mL) were added to the collected crystals, followed by refluxing for 3 hours. The temperature of the resultant mixture was cooled to room temperature. The reaction mixture was concentrated under reduced pressure. The obtained residue was dissolved in chloroform (300 mL). The solution was washed sequentially by a 10% aqueous citric acid solution (200 mL) and saturated brine (100 mL), dried over anhydrous sodium sulfate, filtered, and concentrated under reduced pressure. The obtained residue was dissolved in concentrated hydrochloric acid. The solution was diluted with water, and washed by chloroform (50 mL). The reaction mixture was concentrated under reduced pressure, and precipitated crystals were recrystallized from ethanol and a small amount of water, to thereby yield the title compound as yellow crystals (1.40 g, 57.5%).

mp: 249-259° C.

$^1$H-NMR (400 MHz, D$_2$O) δ ppm: 1.10 (3H, d, J=7.0 Hz), 1.45 (3H, d, J=7.0 Hz), 2.58-2.67 (1H, m), 3.55-3.61 (1H, m), 3.65-3.75 (1H, m), 3.82-3.86 (1H, m), 4.06-4.12 (1H, m), 4.23 (1H, dd, J=2.0, 12.5 Hz), 4.37 (1H, dd, J=2.0, 11.5 Hz), 4.55-4.62 (1H, m), 6.83 (1H, d, J=14.0 Hz), 8.42 (1H, s).

IR(ATR)ν cm$^{-1}$: 3217, 2993, 2808, 1701, 1620, 1523, 1458, 1360, 1277, 1068, 987, 802.

[α]$_D$ −177.20° (c0.660, H$_2$O).

Anal.: Calcd for C$_{18}$H$_{20}$FN$_3$O$_4$HCl 0.25H$_2$O: C, 53.73; H, 5.39; N, 10.44; F, 4.72; Cl, 8.81. Found: C, 53.76; H, 5.37; N, 10.48; F, 4.94; Cl, 8.89.

REFERENTIAL EXAMPLE 25

Ethyl 4-[(3S,4S)-3-(tert-butoxycarbonyl)amino-4-methylpyrrolidin-1-yl]-2,5-difluoro-3-methylbenzoate A solution of (3S,4S)-3-(tert-butoxycarbonyl)amino-4-methylpyrrolidine (1.80 g, 8.97 mmol), ethyl 3-methyl-2,4,5-trifluorobenzoate (2.18 g, 10.0 mmol), and 1,8-diazabicyclo[5.4.0]undeca-7-ene (DBU) (2.24 mL, 15 mmol) in dimethyl sulfoxide (20 mL) was stirred under a nitrogen atmosphere at an external temperature of 60° C. for 70 hours. The temperature of the mixture was cooled to room temperature. The resultant mixture was poured to a 10% aqueous citric acid solution, followed by extraction with ethyl acetate (200 mL×3), washing by water (200 mL), saturated aqueous sodium hydrogencarbonate (150 mL), and saturated brine (150 mL), and dried over anhydrous sodium magnesium. After filtration, the filtrate was concentrated under reduced pressure. The obtained residue was purified through silica gel column chromatography (n-hexane:ethyl acetate=6:1), to thereby yield the title compound as colorless crystals (2.51 g, 70.2%).

$^1$H-NMR (400 MHz, CDCl$_3$) δ ppm: 1.07 (3H, d, J=7.0 Hz), 1.38 (3H, t, J=7.0 Hz), 1.47 (9H, s), 2.20 (3H, d, J=2.5 Hz), 2.50-2.57 (1H, m), 3.06-3.12 (1H, m), 3.16 (1H, dd, J=3.0, 10.0 Hz), 3.39-3.44 (1H, m), 3.73-3.77 (1H, m), 4.27-4.33 (1H, m), 4.36 (2H, q, J=7.0 Hz), 4.71 (1H, br), 7.42 (1H, dd, J=7.0, 13.0 Hz).

MS (ESI) m/z: 399 (M$^+$+1).

REFERENTIAL EXAMPLE 26

4-[(3S,4S)-3-(tert-Butoxycarbonyl)amino-4-methylpyrrolidin-1-yl]-2,5-difluoro-3-methylbenzoic acid A 1 mol/L aqueous sodium hydroxide solution (15 mL, 15 mmol) was added under cooling with ice to a solution of ethyl 4-[(3S,4S)-3-(tert-butoxycarbonyl)amino-4-methylpyrrolidin-1-yl]-2,5-difluoro-3-methylbenzoate (2.51 g, 6.30 mmol) in ethanol (20 mL), followed by stirring at room temperature for 20 hours. The resultant mixture was neutralized with 1 mol/L hydrochloric acid under cooling with ice, and ethanol was removed under reduced pressure. Subsequently, 1 mol/L hydrochloric acid was added to the residue, and the mixture was extracted with ethyl acetate (200 mL×2), followed by drying over anhydrous sodium sulfate. After filtration, the filtrate was concentrated under reduced pressure, and dried under reduced pressure (solvent), to thereby yield the title compound as a yellow oily substance (2.20 g, quantitative amount). The product was employed, without further purification, in the subsequent step.

$^1$H-NMR (400 MHz, CDCl$_3$) δ ppm: 1.08 (3H, d, J=6.5 Hz), 1.47 (9H, s), 2.21 (3H, d, J=2.0 Hz), 2.50-2.56 (1H, m), 3.13-3.25 (2H, m), 3.43-3.49 (1H, m), 3.81 (1H, dd, J=6.0, 8.5 Hz), 4.28-4.34 (1H, m), 4.73 (1H, br), 7.48 (1H, dd, J=7.0, 13.0 Hz).

MS (ESI) m/z: 371 (M$^+$+1).

REFERENTIAL EXAMPLE 27

Ethyl 3-[((3S,4S)-3-(tert-butoxycarbonyl)amino-4-methylpyrrolidin-1-yl)-2,5-difluoro-3-methylphenyl]-3-oxopropionate 1,1'-carbonyldiimidazole (1.46 g, 9.00 mmol) was added to a solution of 4-[(3S,4S)-3-(tert-butoxycarbonyl)amino-4-methylpyrrolidin-1-yl]-2,5-difluoro-3-methylbenzoic acid (2.20 g, 6.30 mmol) in tetrahydrofuran (30 mL), and the mixture was stirred at room temperature for 3 hours. Separately, a magnesium salt was prepared potassium ethyl malonate (3.40 g, 20.0 mmol), magnesium chloride (2.38 g, 25.0 mmol), and triethylamine (4.18 mL, 30.0 mmol), and the salt was dissolved in ethyl acetate (40 mL). The reaction mixture was added dropwise to the solution under cooling with ice, followed by stirring at an external temperature of 50° C. for 16 hours. Under cooling with ice, a 10% aqueous citric acid solution was added thereto, and the resultant mixture was extracted with ethyl acetate (200 mL×2), washed by saturated sodium hydrogencarbonate (100 mL) and saturated brine (100 mL), and dried over anhydrous sodium sulfate. After filtration, the filtrate was concentrated under reduced pressure, and the obtained residue was purified through silica gel column chromatography (n-hexane:ethyl acetate=4:1), to thereby yield the title compound (2.58 g, 93.0%).

$^1$H-NMR (400 MHz, CDCl$_3$) δ ppm: 1.07 (3H, d, J=7.0 Hz), 1.24-1.38 (3H, m), 1.47 (9H, s), 2.20 (3H, d, J=2.5 Hz), 2.49-2.55 (1H, m), 3.02-3.24 (2H, m), 3.37-3.50 (1H, m), 3.69-3.84 (1H, m), 3.91-3.93 (1.4H, m), 4.18-4.30 (3H, m), 5.83 (0.3H, s), 7.35-7.48 (1H, m), 12.68 (0.3H, s).

MS (ESI) m/z: 441 (M$^+$+1).

REFERENTIAL EXAMPLE 28

Ethyl 7-[(3S,4S)-3-(tert-butoxycarbonyl)amino-4-methylpyrrolidin-1-yl]-1-cyclopropyl-6-fluoro-1,4-dihydro-4-oxoquinoline-3-carboxylate A solution of ethyl 3-[((3S,4S)-3-(tert-butoxycarbonyl)amino-4-methylpyrrolidin-1-yl)-2,5-difluoro-3-methylphenyl]-3-oxopropionate (2.58 g, 5.86 mmol) and N,N-dimethylformamide dimethylacetal (3.99 mL, 30.0 mmol) in benzene (40 mL) was refluxed for 4 hours. The temperature of the reaction mixture was cooled to room temperature. The reaction mixture was concentrated under reduced pressure. The obtained residue was dissolved in dichloromethane (20 mL), and cyclopropylamine (693 μL, 10.0 mmol) was added dropwise to the solution under cooling with ice, followed by stirring at room temperature for 18 hours. The reaction mixture was concentrated under reduced pressure. The obtained residue was dissolved in 1,4-dioxane (30 mL), and 55% oily sodium hydride (436 mg, 10.0 mmol) was added to the solution at room temperature, followed by stirring for 2 hours. Subsequently, the resultant mixture was poured to an ice-cooling saturated aqueous ammonium chloride solution. The resultant mixture was extracted with ethyl acetate (200 mL×2), washed by saturated brine (100 mL), and dried over anhydrous sodium sulfate. After filtration, the filtrate was concentrated under reduced pressure. The obtained residue was purified through silica gel column chromatography (chloroform:methanol=25:1), to thereby yield the title compound (957 mg, 33.4%).

$^1$H-NMR (400 MHz, CDCl$_3$) δ ppm: 0.82-0.95 (2H, m), 1.10 (3H, d, J=7.0 Hz), 1.13-1.23 (2H, m), 1.41 (3H, t, J=7.0 Hz), 1.47 (9H, s), 2.55-2.70 (4H, m), 3.17-3.24 (2H, m), 3.48-3.53 (1H, m), 3.82 (1H, ddd, J=1.5, 5.5, 10.0 Hz), 3.93 (1H, ddd, J=3.5, 8.0, 14.0 Hz), 4.32-4.42 (3H, m), 4.74 (1H, br), 7.91 (1H, d, J=13.5 Hz), 8.63 (1H, s).

MS (ESI) m/z: 488 (M$^+$+1).

REFERENTIAL EXAMPLE 29

7-[(3S,4S)-3-(tert-Butoxycarbonyl)amino-4-methylpyrrolidin-1-yl]-1-cyclopropyl-6-fluoro-1,4-dihydro-4-oxoquinoline-3-carboxylic acid (Comparative Compound C)

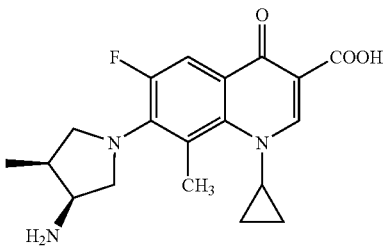

[F31]

A 1 mol/L aqueous sodium hydroxide solution (5 mL, 5 mmol) was added under cooling with ice to ethyl 7-[(3S,4S)-3-(tert-butoxycarbonyl)amino-4-methylpyrrolidin-1-yl]-1-cyclopropyl-6-fluoro-1,4-dihydro-4-oxoquinoline-3-carboxylate (957 mg, 1.96 mmol) in ethanol (10 mL), and the mixture was stirred at room temperature for 3 hours. The resultant mixture was neutralized with 1 mol/L hydrochloric acid under cooling with ice, and ethanol was removed under reduced pressure. Subsequently, 1 mol/L hydrochloric acid was added thereto, followed by extraction with ethyl acetate (100 mL×3). The ethyl acetate layer was washed by saturated brine (100 mL), and dried over anhydrous sodium sulfate. After filtration, the filtrate was concentrated under reduced pressure. The obtained residue was dissolved in concentrated hydrochloric acid (5 mL), and the solution was washed by chloroform (50 mL). The pH of the resultant mixture was adjusted to 7.8 with an aqueous sodium hydroxide solution, followed by extraction with chloroform (100 mL×3) and drying over anhydrous sodium sulfate. After filtration, the filtrate was concentrated under reduced pressure, and the obtained residue was recrystallized from ethanol, to thereby yield the title compound as pale yellow crystals (420 mg, 58.2%).

$^1$H-NMR (400 MHz, 0.1 mol/L NaOD) δ ppm: 0.71-0.85 (2H, m), 1.05 (3H, d, J=7.0 Hz), 1.09-1.21 (2H, m), 2.31-2.41 (1H, m), 2.45 (3H, s), 3.23 (1H, dd, J=3.5, 10.0 Hz), 3.29-3.34 (1H, m), 3.43-3.48 (2H, m), 3.75-3.80 (1H, m), 4.05-4.10 (1H, m), 7.61 (1H, d, J=14.5 Hz), 8.55 (1H, s).

IR(ATR)ν cm$^{-1}$: 2964, 2812, 1724, 1612, 1570, 1435, 1346, 1317, 1196, 1039, 820.

Anal.: Calcd for C$_{19}$H$_{22}$FN$_3$O$_3$.0.5H$_2$O: C, 61.94; H, 6.29; N, 11.41. Found: C, 62.05; H, 6.03; N, 11.42.

REFERENTIAL EXAMPLE 30

7-[(3S,4S)-3-Amino-4-ethylpyrrolidine-1-yl]-1-cyclopropyl-6-fluoro-8-methyl-1,4-dihydro-4-oxoquinoline-3-carboxylic acid (Comparative Compound D)

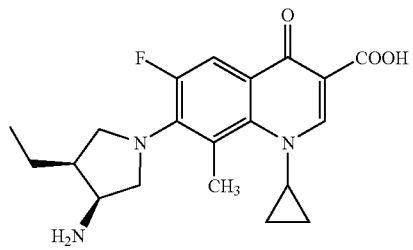

[F32]

1-Cyclopropyl-6,7-difluoro-8-methyl-1,4-dihydro-4-oxoquinoline-3-carboxylic acid difluoroboran complex (486 mg, 1.48 mmol) and triethylamine (309 μL, 2.22 mmol) were added to a solution of (3S,4S)-3-(tert-butoxycarbonyl) amino-4-ethylpyrrolidine (611 mg, 2.85 mmol) in sulfolane (4 mL), and the resultant mixture was stirred in an oil bath at 33° C. for 62 hours. Subsequently, cold water (100 mL) was poured to the reaction mixture, and a precipitated solid was collected through filtration, followed by washing by water (10 mL×3). Ethanol (100 mL), water (5 mL), and triethylamine (2 mL) were added to the obtained solid, followed by refluxing in an oil bath at 100° C. for 2 hours. The reaction mixture was concentrated under reduced pressure. Subsequently, a 10% aqueous citric acid solution (50 mL) was added thereto, and the mixture was extracted with chloroform (100 mL×2). The obtained organic layer was washed by saturated brine (50 mL), and dried over anhydrous sodium sulfate. After filtration, the filtrate was concentrated under reduced pressure. Thereafter, concentrated hydrochloric acid (10 mL) was added to the obtained yellow solid (800 mg) under cooling with ice, and the resultant mixture was stirred at room temperature for 20 minutes. The reaction mixture was washed by chloroform (50 mL×3). The pH of the obtained aqueous layer was adjusted to 12.0 with a 10 mol/L aqueous sodium hydroxide solution under cooling with ice. The pH was adjusted again to 7.4 with concentrated hydrochloric acid and 1 mol/L aqueous hydrochloric acid, and the mixture was extracted with chloroform (200 mL×7). The combined organic layer was dried over anhydrous sodium sulfate, filtered, and concentrated under reduced pressure. The obtained residue was recrystallized from ethanol, and dried under reduced pressure, to thereby yield the title compound as pale yellow crystals (367 mg, 58%).

mp: 148-150° C.

$^1$H-NMR (400 MHz, 0.1 mol/L NaOD) δ ppm: 0.72-0.79 (1H, m), 0.84-0.90 (1H, m), 0.97 (3H, t, J=7.5 Hz), 1.07-1.14 (1H, m), 1.19 (3H, t, J=7.1 Hz), 1.21-1.26 (1H, m), 1.46 (1H, q, J=7.1 Hz), 1.53 (1H, q, J=7.1 Hz), 2.16-2.23 (1H, m), 2.51 (3H, s), 3.20 (1H, d, J=10.0 Hz), 3.39 (1H, t, J=8.5 Hz), 3.45-3.53 (2H, m), 3.66 (2H, q, J=7.1 Hz), 3.90-3.94 (1H, m), 4.08-4.14 (1H, m), 7.64 (1H, d, J=14.5 Hz), 8.56 (1H, s).

IR(ATR)ν cm$^{-1}$: 3228, 2966, 2920, 2877, 1726, 1635, 1570, 1554, 1512, 1468, 1442, 1379, 1346, 1306.

Anal.: Calcd for $C_{19}H_{22}FN_3O_3 \cdot 0.5H_2O$: C, 61.94; H, 6.29; N, 11.41. Found: C, 62.05; H, 6.03; N, 11.42.

Anal.: Calcd. for $C_{25}H_{32}FN_3O_5 \cdot 1.0CH_3CH_2OH \cdot 0.25H_2O$: C, 62.32; H, 7.25; N, 9.91; F, 4.48. Found: C, 62.04; H, 7.26; N, 9.90; F, 4.65.

EXAMPLE 14

7-[(3S,4S)-3-Amino-4-ethylpyrrolidine-1-yl]-1-[(1R,2S)-2-fluorocyclopropyl]-8-methyl-1,4-dihydro-4-oxoquinoline-3-carboxylic acid (Compound No. 14)

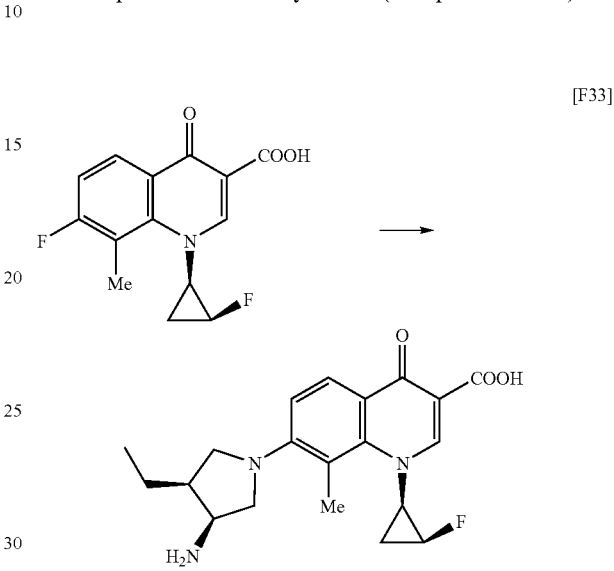

[F33]

A 10% palladium carbon catalyst (27 mg) was added to a solution of (3S,4S)-1-(benzyloxycarbonyl)-3-(tert-butoxycarbonylamino)-4-ethylpyrrolidine (270 mg, 775 μmol) in methanol (7.75 mL), and the resultant mixture was stirred under a hydrogen atmosphere at room temperature for 15 hours. After filtration, the filtrate was concentrated under reduced pressure. The obtained residue was dissolved in dimethyl sulfoxide (3 mL), and 7-fluoro-1-[(1R,2S)-2-fluorocyclopropyl]-8-methyl-1,4-dihydro-4-oxoquinoline-3-carboxylic acid (216 mg, 775 μmol) and triethylamine (130 μL, 930 μmol) were added to the solution, followed by stirring in an oil bath at 65° C. for 8 days. The reaction mixture was concentrated under reduced pressure, and the residue was dissolved in ethyl acetate (50 mL). The solution was washed sequentially with a 10% aqueous citric acid solution (30 mL), water (30 mL×2), and saturated brine (30 mL), followed by drying over anhydrous sodium sulfate. After filtration, the filtrate was concentrated under reduced pressure. Subsequently, concentrated hydrochloric acid (2 mL) was added to the obtained residue at room temperature, and the resultant mixture was transferred to a separatory funnel with water (20 mL), followed by washing by chloroform (30 mL×2). The pH of the obtained aqueous layer was adjusted to 12.0 with a 10 mol/L aqueous sodium hydroxide solution under cooling with ice. The pH was adjusted again to 7.4, and the resultant mixture was extracted with chloroform (100 mL×3). The combined organic layer was dried over anhydrous sodium sulfate, and the solvent was removed under reduced pressure. The obtained residue was recrystallized from hot ethanol, and dried under reduced pressure, to thereby yield the title compound as pale yellow crystals (145 mg, 50.1%).

mp: 232-234° C.

$^1$H-NMR (400 MHz, 0.1N-NaOD) δ ppm: 0.96 (3H, t, J=7.4 Hz), 1.13-1.29 (1H, m), 1.41-1.66 (3H, m), 2.07-2.23 (1H, m), 2.34 (3H, s), 3.06 (1H, d, J=10.3 Hz), 3.19 (1H, t, J=8.7 Hz), 3.43-3.60 (2H, m), 3.77 (1H, dd, J=4.6, 10.3 Hz), 3.99-4.04 (1H, m), 5.03 (1H, d, J=65.2 Hz), 6.98 (1H, d, J=9.0 Hz), 7.95 (1H, d, J=9.0 Hz), 8.42 (1H, d, J=3.7 Hz).

Anal.: Calcd for $C_{20}H_{24}FN_3O_3$: C, 64.33; H, 6.48; F, 5.09; N, 11.25.

Found: C, 64.01; H, 6.55; F, 4.95; N, 10.89.

MS (ESI) m/z: 374 (M+1)$^+$

IR(ATR): 3386, 3037, 2962, 2914, 2856, 1705, 1616, 1550, 1514, 1462, 1435, 1379, 1350, 1327 cm$^{-1}$

EXAMPLE 15

7-[(3S,4S)-3-Ethyl-4-methylaminopyrrolidin-1-yl]-6-fluoro-1-[(1R,2S)-2-fluorocyclopropyl]-8-methyl-1,4-dihydro-4-oxoquinoline-3-carboxylic acid (Compound No. 15)

[F34]

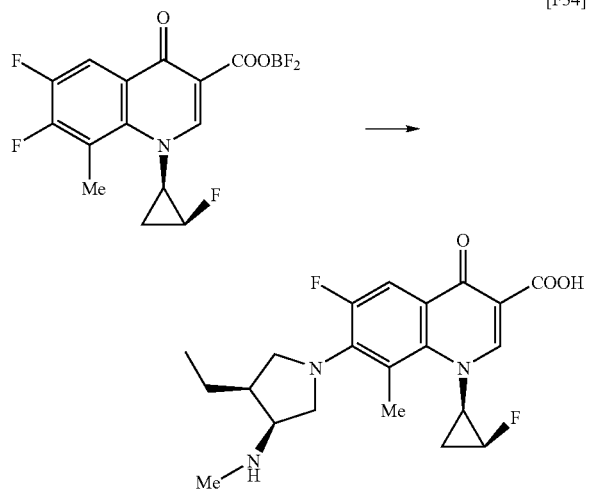

6,7-Difluoro-1-[(1R,2S)-2-fluorocyclopropyl]-8-methyl-1,4-dihydro-4-oxoquinoline-3-carboxylic acid difluoroboran complex (100 mg, 290 μmol) and triethylamine (48.5 μL, 348 μmol) were added to a solution of (3S,4S)-3-(tert-butoxycarbonyl-N-methylamino)-4-ethylpyrrolidine (410 mg, 1.80 mmol) in sulfolane (1.5 mL), and the resultant mixture was stirred at 45° C. for 5 days. Ethanol (20 mL) and water (5 mL) were added thereto, and triethylamine (5 mL) was added to the reaction mixture, followed by refluxing in an oil bath at 90° C. for 3 hours. The reaction mixture was concentrated under reduced pressure, and dissolved in ethyl acetate (200 mL). The solution was washed sequentially with a 10% aqueous citric acid solution (50 mL), water (50 mL×6), and saturated brine (50 mL). The obtained organic layer was dried over anhydrous sodium sulfate. After filtration, the filtrate was concentrated under reduced pressure. The obtained yellow oily substance was purified through preparative TLC (methanol:chloroform=1:10). Thereafter, concentrated hydrochloric acid (6 mL) was added at room temperature so as to dissolve the obtained yellow oily substance. The solution was washed with chloroform (50 mL×2). The pH of the obtained aqueous layer was adjusted to 12.0 with a 10 mol/L aqueous sodium hydroxide solution under cooling with ice. The pH was adjusted again to 7.4. The resultant mixture was extracted with chloroform (100 mL×2). The combined organic layer was dried over anhydrous sodium sulfate, and the solvent was removed under reduced pressure. The obtained residue was recrystallized from hot ethanol, and dried under reduced pressure, to thereby yield the title compound as pale yellow crystals (28.0 mg, 23.8%).

mp: 223-225° C.

$^1$H-NMR (400 MHz, 0.1N-NaOD) δ ppm: 0.97 (3H, t, J=7.4 Hz), 1.22-1.68 (4H, m), 2.24-2.34 (1H, m), 2.32 (3H, s), 2.47 (3H, s), 3.24-3.30 (1H, m), 3.35-3.57 (3H, m), 3.80-3.88 (1H, m), 4.05-4.12 (1H, m), 5.01 (1H, d, J=63.4 Hz), 7.67 (1H, d, J=14.4 Hz), 8.44 (1H, d, J=2.9 Hz).

Anal.: Calcd for $C_{21}H_{25}F_2N_3O_3$: C, 62.21; H, 6.22; F, 9.37; N, 10.36. Found: C, 61.97; H, 6.31; F, 9.50; N, 10.11.

MS (ESI) m/z: 406 (M+1)$^+$

IR(ATR): 3319, 2939, 2877, 2800, 1724, 1610, 1504, 1427, 1346, 1313, 1271, 1225, 1201, 1173, 1136, 1105 cm$^{-1}$

REFERENTIAL EXAMPLE 31

4-Isopropylidene-2-oxo-1-[(1R)-phenylethyl]pyrrolidine

[F35]

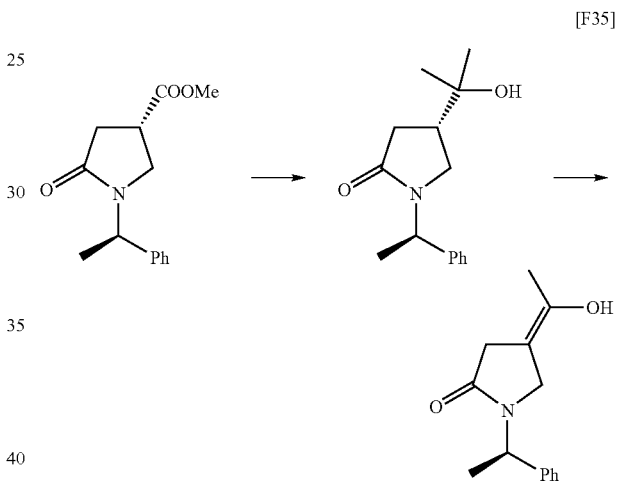

Methylmagnesium bromide in tetrahydrofuran (1 mol/L, 1.21 L, 1.21 mol) was added under cooling with ice to a solution of (3S)-5-oxo-1-[(1R)-phenylethyl]pyrrolidine-3-carboxylic acid methyl ester (100 g, 404 mmol) in tetrahydrofuran (1.20 L), and the resultant mixture was stirred at 0° C. for 30 minutes. Subsequently, a saturated aqueous ammonium chloride solution (1.00 L) was added to the reaction mixture at the same temperature. The resultant mixture was extracted with ethyl acetate (1.00 L×2), followed by extraction with saturated brine (700 mL). The organic layer was dried over anhydrous sodium sulfate, and the solvent was removed under reduced pressure, to thereby obtain crude 4-(1-hydroxy-1-methyl-ethyl)-2-oxo-1-[(1R)-phenylethyl] pyrrolidine. The product was dissolved in dichloromethane (1.00 L), and triethylamine (225 mL, 1.62 mol) and 4-dimethylaminopyridine (197 g, 1.62 mol) were added to the solution. Thereafter, methanesulfonyl chloride (125 mL, 1.62 mol) was added dropwise thereto under cooling with ice. The mixture was stirred at room temperature for 13 hours. Subsequently, a saturated aqueous ammonium chloride solution (1.00 L) was added to the reaction mixture under cooling with ice. The resultant mixture was extracted with ethyl acetate (1.00 L×2), followed by washing by saturated brine (700 mL). The obtained organic layer was dried over anhydrous sodium sulfate, and the solvent was removed under reduced pressure.

The obtained residue was purified through silica gel column chromatography (n-hexane:ethyl acetate=4:1 to 1:1), to thereby yield the title compound as colorless solid (66.0 g, 71%).

$^1$H-NMR (40 MHz, CDCl$_3$) δ ppm: 1.53 (3H, s), 1.56 (3H, d, J=7.3 Hz), 1.62 (3H, s), 3.06-3.10 (2H, m), 3.52 (1H, d, J=13.4 Hz), 3.89 (1H, d, J=13.4 Hz), 5.62 (1H, q, J=7.2 Hz), 7.25-7.38 (5H, m).

REFERENTIAL EXAMPLE 32

(4R&S)-4-Isopropyl-2-oxo-1-[(1R)-phenylethyl]pyrrolidine

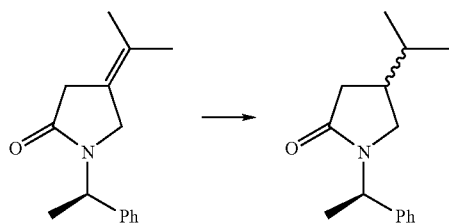

[F36]

A 10% palladium carbon catalyst (M, water content: 52.8%, 50.0 g) was added to a solution of 4-isopropylidene-2-oxo-1-[(1R)-phenylethyl]pyrrolidine (52.0 g, 225 mmol) in ethanol (1.00 L), and the resultant mixture was stirred in a hydrogen atmosphere at 40° C. for 16 hours. The catalyst was removed through filtration (washing by ethanol), and the filtrate was concentrated under reduced pressure. The residue was purified through silica gel column chromatography (n-hexane:ethyl acetate=3:1 to 1:1), to thereby yield the title compound as a colorless syrupy substance (48.0 g, 92%).

$^1$H-NMR (400 MHz, CDCl$_3$) δ ppm: 0.77-0.91 (6H, m), 1.41-1.57 (1H, m), 1.50-1.53 (3H, m), 1.89-2.21 (2H, m), 2.47-2.62 (1H, m), 2.95-3.07 (2H, m), 5.46-5.55 (1H, m), 7.26-7.36 (5H, m).

REFERENTIAL EXAMPLE 33

(3R,4S&3S,4R)-3-Hydroxy-4-isopropyl-2-oxo-1-[(1R)-phenylethyl]pyrrolidine

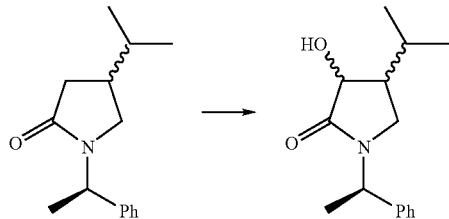

[F37]

Triethyl phosphite (38.9 mL, 227 mmol) was added to a solution of (4R&S)-4-isopropyl-2-oxo-1-[(1R)-phenylethyl]pyrrolidine (43.8 g, 189 mmol) in diethyl ether (900 mL). Subsequently, lithium diisopropylamide in tetrahydrofuran (2 mol/L, 142 mL, 284 mmol) was added dropwise to the resultant mixture at −90° C., followed by stirring at −80° C. for 20 minutes. Thereafter, oxygen was fed into the mixture at −90° C. for 1 hour. A saturated aqueous ammonium chloride solution (1.00 L) was added to the reaction mixture at the same temperature. The resultant mixture was extracted with ethyl acetate (1.00 L×2), followed by washing with water (1.00 L) and saturated brine (700 mL). The obtained organic layer was dried over anhydrous sodium sulfate, and the solvent was removed under reduced pressure. The obtained residue was recrystallized from chloroform-n-hexane, to thereby yield the title compound as colorless solid (14.1 g, 30%, a mixture of (3R,4S) form and (3S,4R) form (about 5:1)).

$^1$H-NMR (400 MHz, CDCl$_3$) δ ppm: 0.81-0.88 (3H, m), 0.99-1.06 (3H, m), 1.52-1.57 (3H, m), 1.70-1.90 (2H, m), 2.88 (1H, t, J=9.4 Hz), 3.02 (1H, t, J=9.0 Hz), 3.10-3.19 (1H, m), 4.08 (1H, dd, J=8.9, 1.8 Hz), 5.46 (1H, q, J=7.2 Hz), 7.25-7.38 (5H, m).

REFERENTIAL EXAMPLE 34

(3S,4S)-3-Azide-4-isopropyl-2-oxo-1-[(1R)-phenylethyl]pyrrolidine

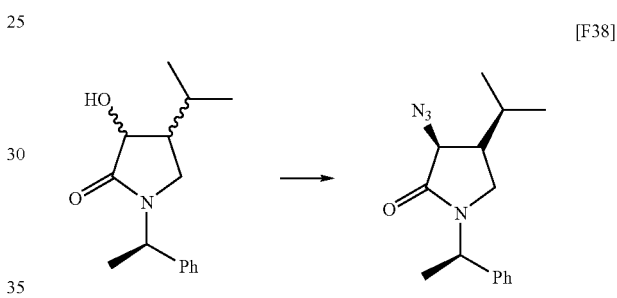

[F38]

Triethylamine (17.5 mL, 125 mmol) was added to a solution of (3R,4S&3S,4R)-3-hydroxy-4-isopropyl-2-oxo-1-[(1R)-phenylethyl]pyrrolidine (14.1 g, 57.0 mmol) in dichloromethane (280 mL). Subsequently, methanesulfonyl chloride (8.82 mL, 114 mmol) was added dropwise to the resultant mixture under cooling with ice. The mixture was stirred at the same temperature for 30 minutes. Thereafter, a saturated aqueous ammonium chloride solution (500 mL) was added to the reaction mixture under cooling with ice, followed by extraction with ethyl acetate (500 mL×2), and washing by water (200 mL) and saturated brine (200 mL). The obtained organic layer was dried over anhydrous sodium sulfate, and the solvent was removed under reduced pressure. The obtained residue was dissolved in N,N-dimethylformamide (150 mL). Subsequently, sodium azide (9.26 g, 143 mmol) was added to the solution. The resultant mixture was stirred at 60° C. for 12 hours, and further at room temperature for 48 hours. Thereafter, water (500 mL) was added to the reaction mixture under cooling with ice, followed by extraction with ethyl acetate (500 mL×2). The ethyl acetate layer was washed by water (500 mL×2) and saturated brine (500 mL). The obtained organic layer was dried over anhydrous sodium sulfate, and the solvent was removed under reduced pressure. The obtained residue was purified through silica gel column chromatography (n-hexane:ethyl acetate=9:1 to 6:1 to 1:1), to thereby yield the title compound as a colorless syrupy substance (11.9 g, 77%).

$^1$H-NMR (400 MHz, CDCl$_3$) δ ppm: 0.81 (3H, d, J=6.3 Hz), 0.97 (3H, d, J=6.1 Hz), 1.56 (3H, d, J=7.1 Hz), 1.76-1.89

(2H, m), 2.96 (1H, dd, J=9.6, 7.2 Hz), 3.04 (1H, t, J=9.0 Hz), 4.06 (1H, d, J=6.3 Hz), 5.47 (1H, q, J=7.2 Hz), 7.26--7.38 (5H, m).

REFERENTIAL EXAMPLE 35

(3S,4S)-3-(tert-Butoxycarbonylamino)-4-isopropyl-2-oxo-1-[(1R)-phenylethyl]pyrrolidine

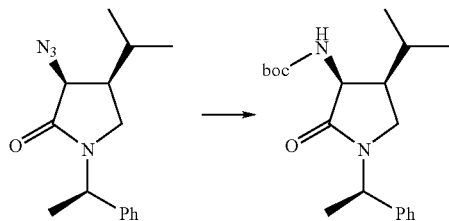

[F39]

A 10% palladium carbon catalyst (M, water content: 52.8%, 1.20 g) was added to a solution of (3S,4S)-3-azide-4-isopropyl-2-oxo-1-[(1R)-phenylethyl]pyrrolidine (11.9 g, 43.7 mmol) in ethanol (500 mL), and the resultant mixture was stirred in a hydrogen gas atmosphere for 1 hour. Subsequently, di-tert-butyldicarbonate (19.1 g, 87.4 mmol) was added thereto. The reaction mixture was further stirred in a hydrogen gas atmosphere for 14 hours. Thereafter, the catalyst was removed through filtration (washing by ethanol), and the filtrate was concentrated under reduced pressure. The obtained residue was purified through silica gel column chromatography (n-hexane:ethyl acetate=4:1), to thereby yield the title compound as colorless solid (13.9 g, 92%).

$^1$H-NMR (400 MHz, CDCl3) δ ppm: 0.74 (3H, d, J=6.1 Hz), 0.92 (3H, d, J=5.9 Hz), 1.46 (9H, d, J=1.2 Hz), 1.57 (3H, dd, J=7.1, 1.0 Hz), 1.82-1.91 (1H, m), 2.38 (1H, brs), 2.89 (1H, dd, J=9.9, 7.4 Hz), 3.11 (1H, d, J=10.5 Hz), 4.27-4.33 (1H, m), 5.02-5.05 (1H, m), 5.49 (1H, q, J=7.0 Hz), 7.25-7.37 (5H, m).

REFERENTIAL EXAMPLE 36

(3S,4S)-3-(tert-Butoxycarbonylamino)-4-isopropyl-1-[(1R)-phenylethyl]pyrrolidine

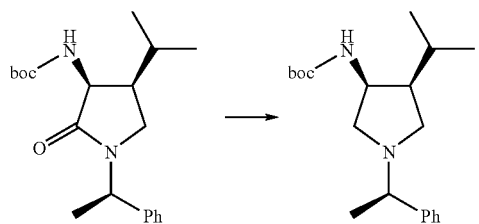

[F40]

A solution of boran-tetrahydrofuran complex in tetrahydrofuran (1.00 mol/L, 63.9 mL, 63.9 mmol) was added dropwise to a solution of (3S,4S)-3-(tert-butoxycarbonylamino)-4-isopropyl-2-oxo-1-[(1R)-phenylethyl]pyrrolidine (7.38 g, 21.3 mmol) in tetrahydrofuran (150 mL) under cooling with ice, and the resultant mixture was stirred at room temperature for 15 hours. The reaction mixture was concentrated under reduced pressure. Subsequently, ethanol and water mixture solution (9:1) (176 mL) and triethylamine (7 mL) were added to the residue, followed by refluxing for 2 hours. The reaction system was concentrated under reduced pressure, and the residue was dissolved in chloroform (150 mL×2). The solution was washed by water (100 mL) and saturated brine (100 mL). The obtained organic layer was dried over anhydrous sodium sulfate, and the solvent was removed under reduced pressure. The obtained residue was purified through silica gel column chromatography (chloroform:methanol=19:1), to thereby yield the title compound as yellow crystals (6.90 g, 97%).

$^1$H-NMR (400 MHz, CDCl3) δ ppm: 0.76 (3H, d, J=6.6 Hz), 0.91 (3H, d, J=6.4 Hz), 1.31 (3H, d, J=6.6 Hz), 1.46 (10H, s), 1.73-1.83 (1H, m), 2.34 (1H, t, J=9.4 Hz), 2.50 (1H, t, J=9.7 Hz), 2.67 (1H, dd, J=9.2, 4.0 Hz), 2.79 (1H, d, J=9.3 Hz), 3.37 (1H, q, J=6.6 Hz), 4.17-4.24 (1H, m), 4.92 (1H, d, J=10.0 Hz), 7.20-7.34 (5H, m).

EXAMPLE 16

7-[(3S,4S)-3-Amino-4-isopropylpyrrolidine-1-yl]-6-fluoro-1-[(1R,2S)-2-fluorocyclopropyl]-8-methyl-1,4-dihydro-4-oxoquinoline-3-carboxylic acid (Compound No. 16)

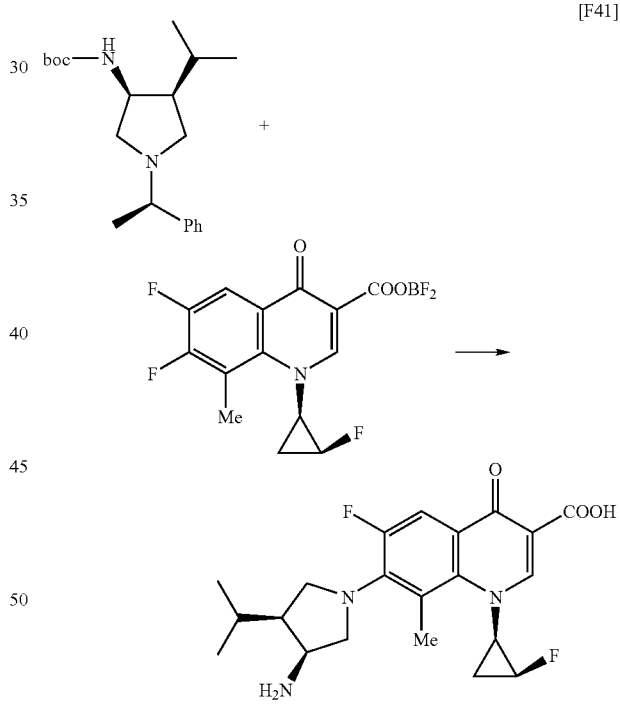

[F41]

A 10% palladium carbon catalyst (M, water content: 52.8%, 5.00 g) was added to a solution of (3S,4S)-3-(tert-butoxycarbonylamino)-4-isopropyl-1-[(1R)-phenylethyl]pyrrolidine (5.68 g, 17.1 mmol) in ethanol (240 mL), and the resultant mixture was stirred under a hydrogen gas atmosphere at 40° C. for 17 hours. The catalyst was removed through filtration (washing by ethanol), and the filtrate was concentrated under reduced pressure. Subsequently, a 1 mol/L aqueous sodium hydroxide solution (2 mL) was added to the residue, followed by extraction with chloroform (50 mL×5), and drying over anhydrous sodium sulfate. The solvent was removed under reduced pressure. To a solution of the obtained (3S,4S)-3-(N-tert-butoxycarbonyl-N-methyl) amino-4-isopropylpyrrolidine (4.00 g, 17.1 mmol) sulfolane (20 mL), triethylamine (1.43 mL, 10.2 mmol) and 6,7-difluoro-1-[(1R,2S)-2-fluorocyclopropyl]-8-methyl-1,4-dihydro-4-oxoquinoline-3-carboxylic acid-difluoroboran complex (2.95 g, 8.54 mmol) were added, and the resultant mixture was stirred for 7 days. Thereafter, an ethanol-water mixture (9:1) (200 mL) and triethylamine (2 mL) were added to the reaction mixture, followed by refluxing for 30 minutes. The reaction system was concentrated under reduced pressure, and the residue was dissolved in ethyl acetate (300 mL). The obtained solution was washed by a 10% aqueous citric acid solution (100 mL), water (100 mL×3), and saturated brine (100 mL). The obtained organic layer was dried over anhydrous sodium sulfate, and the solvent was removed under reduced pressure. The obtained residue was purified through short silica gel column chromatography (chloroform:methanol=49:1 to 9:1). The thus-purified product was dissolved in concentrated hydrochloric acid (10 mL) under cooling with ice, and the resultant solution was stirred at room temperature for 15 minutes. Subsequently, the reaction mixture was washed by chloroform (150 mL×3). The pH of the obtained aqueous layer was adjusted to 11.0 with a 10 mol/L aqueous sodium hydroxide solution under cooling with ice. The pH was adjusted again to 7.4 with hydrochloric acid, followed by extraction with chloroform (200 mL×4). The combined organic layer was dried over anhydrous sodium sulfate, and the solvent was removed under reduced pressure. The obtained residue was recrystallized from ethanol (in the presence of activated carbon), and dried under reduced pressure, to thereby yield the title compound as pale yellow crystals (1.32 g, 37%).

mp: 124-127° C.

$^1$H-NMR (400 MHz, 0.1N-NaOD) δ ppm: 0.97 (6H, dd, J=32.2, 6.1 Hz), 1.16-1.28 (1H, m), 1.61 (1H, dd, J=16.4, 6.1 Hz), 1.69-1.78 (1H, m), 1.88-1.97 (1H, m), 2.43 (3H, s), 3.13 (1H, d, J=10.3 Hz), 3.29 (1H, t, J=8.3 Hz), 3.54 (1H, s), 3.68 (1H, dd, J=17.5, 7.7 Hz), 4.03-4.11 (2H, m), 5.02 (1H, d, J=64.0 Hz), 7.66 (1H, d, J=14.2 Hz), 8.42 (1H, d, J=3.4 Hz).

Anal.: Calcd for $C_{21}H_{25}F_2N_3O_3 \cdot 1H_2O$: C, 59.56; H, 6.43; F, 8.97; N, 9.92. Found: C, 59.38; H, 6.33; F, 9.06; N, 10.00.

IR(ATR): 3444, 2956, 2929, 2871, 1728, 1618, 1545, 1506, 1468, 1431, 1358, 1306, 1230, cm$^{-1}$.

REFERENTIAL EXAMPLE 37

(3S,4S)-3-(N-tert-Butoxycarbonyl-N-methyl)amino-4-isopropyl-2-oxo-1-[(1R)-phenylethyl]pyrrolidine

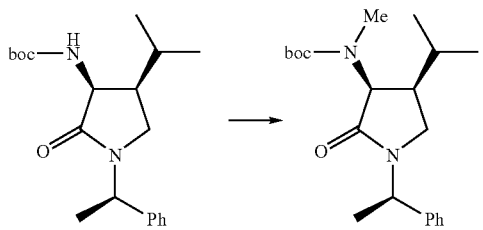

[F42]

Sodium hydride (55%, 723 mg, 16.6 mmol) was added to a solution of (3S,4S)-3-(tert-butoxycarbonylamino)-4-isopropyl-2-oxo-1-[(1R)-phenylethyl]pyrrolidine (2.87 g, 8.28 mmol) in N,N-dimethylformamide (29 mL), and the resultant mixture was stirred at 0° C. for 10 minutes. Subsequently, methyl iodide (0.774 mL, 12.4 mmol) was added thereto at the same temperature, followed by stirring for 30 minutes. Thereafter, a saturated aqueous ammonium chloride solution (50 mL) was added to the reaction mixture, followed by extraction with ethyl acetate (50 mL×2), and washing by water (30 mL×2) and saturated brine (30 mL). The obtained organic layer was dried over anhydrous sodium sulfate, and the solvent was removed under reduced pressure. The obtained residue was purified through silica gel column chromatography (n-hexane ethyl acetate=4:1 to 2:1), to thereby yield the title compound as colorless solid (2.59 g, 87%).

$^1$H-NMR (400 MHz, CDCl$_3$) δ ppm: 0.81-0.87 (3H, m), 0.96 (3H, t, J=7.0 Hz), 1.46-1.48 (10H, m), 1.55 (3H, d, J=7.4 Hz), 1.84-1.97 (1H, m), 2.75 (3H, s), 3.05 (2H, dt, J=23.4, 9.5 Hz), 4.85 (1H, d, J=8.8 Hz), 5.57 (1H, q, J=7.0 Hz), 7.26-7.38 (5H, m).

REFERENTIAL EXAMPLE 38

(3S,4S)-3-(N-tert-Butoxycarbonyl-N-methyl)amino-4-isopropyl-1-[1-(R)-phenylethyl]pyrrolidine

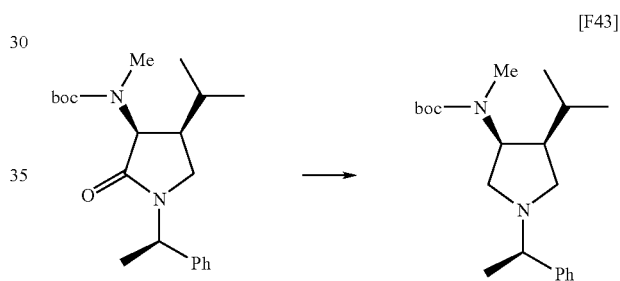

[F43]

A solution of boran-tetrahydrofuran complex in tetrahydrofuran (1.07 mol/L, 21.5 mL, 23.0 mmol) was added dropwise under cooling with ice to a solution of (3S,4S)-3-(N-tert-butoxycarbonyl-N-methyl)amino-4-isopropyl-2-oxo-1-[(1R)-phenylethyl]pyrrolidine (2.59 g, 7.28 mmol) in tetrahydrofuran (50 mL), and the resultant mixture was stirred at room temperature for 15 hours. The reaction mixture was concentrated under reduced pressure. Subsequently, an ethanol and water mixture (9:1) (55 mL) and triethylamine (3 mL) were added to the residue, followed by refluxing for 2 hours. The reaction system was concentrated under reduced pressure, and the residue was dissolved in chloroform (150 mL×2), followed by washing by water (100 mL) and saturated brine (100 mL). The obtained organic layer was dried over anhydrous sodium sulfate, and the solvent was removed under reduced pressure. The obtained residue was purified through silica gel column chromatography (chloroform:methanol=19:1), to thereby yield the title compound as yellow crystals (2.09 g, 84%).

$^1$H-NMR (400 MHz, CDCl$_3$) δ ppm: 0.85 (3H, dd, J=36.5, 5.6 Hz), 1.33 (3H, d, J=5.9 Hz), 1.44 (9H, s), 1.86-2.00 (1H, m), 2.45 (1H, t, J=9.9 Hz), 2.61-2.91 (4H, m), 3.01 (3H, s), 3.38 (1H, q, J=6.5 Hz), 4.85 (1H, brs), 7.26 (5H, t, J=13.0 Hz).

REFERENTIAL EXAMPLE 39

(3S,4S)-3-(N-tert-Butoxycarbonyl-N-methyl)amino-4-isopropylpyrrolidine

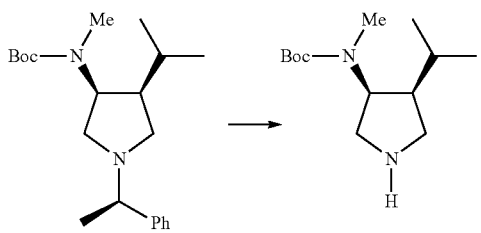

[F44]

(3S,4S)-3-(N-tert-Butoxycarbonyl-N-methyl)amino-4-isopropyl-1-[1-(R)-phenylethyl]pyrrolidine (1.39 g, 4.00 mmol) was dissolved in ethanol (56 mL). Subsequently, a 10% palladium carbon catalyst (M, water content: 50.9%, 1.00 g) was added to the resultant solution, followed by stirring under hydrogen float at 40° C. for 12 hours. The catalyst was removed through filtration (washing by ethanol), and the filtrate was concentrated under reduced pressure. Thereafter, a 1 mol/L aqueous sodium hydroxide solution (2 mL) was added to the residue. The resultant mixture was extracted with chloroform (50 mL×5), followed by drying over anhydrous sodium sulfate. The solvent was removed under reduced pressure, to thereby yield the unpurified title compound as colorless syrup (942 mg, 97%).

$^1$H-NMR (400 MHz, CDCl$_3$) δ ppm: 1.47 (9H, s), 2.54-2.68 (1H, m), 2.85 (3H, s), 2.97 (1H, dd, J=11.3, 7.1 Hz), 3.07 (1H, dd, J=11.5, 5.6 Hz), 3.16-3.23 (2H, m), 4.36 (1H, ddd, J=47.6, 9.3, 6.4 Hz), 4.48 (1H, ddd, J=46.8, 9.1, 5.1 Hz), 4.41-4.48 (1H, m).

EXAMPLE 17

6-Fluoro-1-[(1R,2S)-2-fluorocyclopropyl]-7-[(3S,4S)-3-isopropyl-4-methylaminopyrrolidin-1-yl]-8-methyl-1,4-dihydro-4-oxoquinoline-3-carboxylic acid (Compound No. 17)

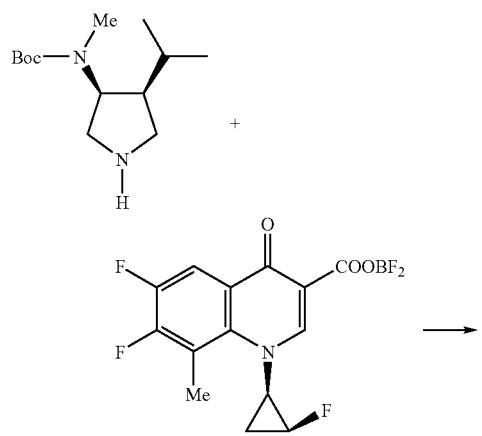

[F45]

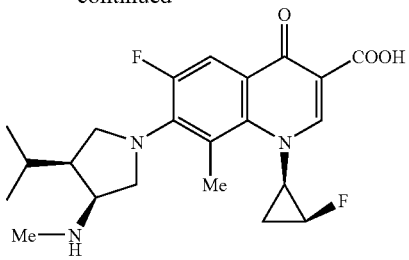

Triethylamine (0.335 mL, 2.40 mmol) and 6,7-difluoro-1-[(1R,2S)-2-fluorocyclopropyl]-8-methyl-1,4-dihydro-4-oxoquinoline-3-carboxylic acid-difluoroboran complex (690 mg, 2.00 mmol) were added to a solution of (3S,4S)-3-(N-tert-butoxycarbonyl-N-methyl)amino-4-isopropylpyrrolidine (942 mg, 3.89 mmol) in sulfolane (5 mL), and the resultant mixture was stirred at room temperature for 12 days. Subsequently, cold water (100 mL) was added to the reaction mixture, and a precipitated solid was collected through filtration. Thereafter, an ethanol and water mixture (9:1) (100 mL) and triethylamine (1 mL) were added to the obtained solid, followed by refluxing for 30 minutes. The reaction system was concentrated under reduced pressure, and the residue was dissolved in ethyl acetate (150 mL×2). The solution was washed by a 10% aqueous citric acid solution (100 mL), water (100 mL×2), and saturated brine (100 mL). The obtained organic layer was dried over anhydrous sodium sulfate, and the solvent was removed under reduced pressure. The obtained residue was purified through short silica gel column chromatography (chloroform:methanol=19:1 to 4:1). The purified product was dissolved under cooling with ice in concentrated hydrochloric acid (5 mL), followed by stirring at room temperature for 30 minutes. Thereafter, the reaction mixture was washed by chloroform (50 mL×3). The pH of the obtained aqueous layer was adjusted to 12.0 with a 10 mol/L aqueous sodium hydroxide solution under cooling with ice. The pH was adjusted again to 7.4 with hydrochloric acid. The resultant mixture was extracted with chloroform (100 mL×3). The combined organic layer was dried over anhydrous sodium sulfate, and the solvent was removed under reduced pressure. The obtained residue was purified through preparative chromatography, recrystallized from ethanol-diethyl ether, and dried under reduced pressure, to thereby yield the title compound as yellow crystals (49.0 mg, 6%).

mp: 168-171° C.

$^1$H-NMR (400 MHz, 0.1N-NaOD) δ ppm: 1.26-1.38 (1H, m), 1.58-1.69 (1H, m), 2.36 (3H, s), 2.54 (3H, s), 2.82-2.93 (1H, m), 3.41 (1H, q, J=5.0 Hz), 3.49 (1H, q, J=5.8 Hz), 3.58 (2H, d, J=6.9 Hz), 3.79 (1H, ddd, J=9.6, 6.1, 1.5 Hz), 4.12 (1H, dt, J=8.6, 5.4 Hz), 4.72-4.80 (2H, m), 5.00 (1H, d, J=65.0 Hz), 7.70 (1H, d, J=14.0 Hz), 8.48 (1H, d, J=2.7 Hz).

Anal.: Calcd for $C_{22}H_{27}F_2N_3O_3 \cdot 0.75H_2O$: C, 61.03; H, 6.63; F, 8.78; N, 9.70. Found: C, 60.68; H, 6.14; F, 9.04; N, 9.59.

IR(ATR): 3082, 2960, 2935, 2870, 2796, 1716, 1614, 1508, 1466, 1431, 1360, 1335, 1313, 1257, 1225 cm$^{-1}$.

TEST EXAMPLE 1

Antibacterial Activity

The antimicrobial activities of the compounds of the present invention were determined according to a standard method designated by the Japan Society of Chemotherapy. The results are expressed by MIC (μg/mL) (Table 1). In Table 1, *S. aureus* 870307 and *S. pneumonia* J24 are quinolone-resistant bacteria.

TABLE 1

| Bacterium | Compound No. 1 | Compound No. 2 | Compound No. 3 | Compound No. 5 | Compound No. 8 | Compound No. 16 |
|---|---|---|---|---|---|---|
| E. coli NIHJ | 0.006 | ≦0.003 | 0.006 | 0.006 | 0.006 | 0.006 |
| S. flexneri 2A 5503 | 0.006 | ≦0.003 | 0.006 | 0.006 | 0.025 | 0.006 |
| P. Vulgalis 08601 | 0.012 | 0.006 | 0.006 | 0.012 | 0.025 | 0.025 |
| K. pneumoniae TYPE I | 0.025 | 0.025 | 0.05 | 0.025 | 0.05 | 0.025 |
| S. marcescens 10100 | 0.1 | 0.025 | 0.025 | 0.05 | 0.1 | 0.05 |
| P. aeruginosa 32104 | 0.2 | 0.05 | 0.1 | 0.2 | 0.2 | 0.2 |
| P. aeruginosa 32121 | 0.1 | 0.025 | 0.05 | 0.1 | 0.1 | 0.1 |
| S. maltophilia IID 1275 | 0.05 | 0.05 | 0.2 | 0.05 | 0.2 | 0.05 |
| S. aureus FDA 209P | 0.006 | 0.006 | 0.012 | 0.006 | 0.012 | 0.006 |
| S. epidermidis 56500 | 0.05 | 0.025 | 0.05 | 0.025 | 0.1 | 0.025 |
| S. pyogenes G-36 | 0.05 | 0.025 | 0.1 | 0.025 | 0.1 | 0.025 |
| E. faevcalis ATCC 19433 | 0.1 | 0.1 | 0.1 | 0.1 | 0.1 | 0.1 |
| S. aureus 870307 | 0.2 | 0.39 | 0.78 | 0.2 | 0.39 | 0.1 |
| S. pneumoniae J24 | 0.025 | 0.025 | 0.1 | 0.025 | 0.1 | 0.05 |

| Bacterium | Comparative Compound A | Comparative Compound B | Comparative Compound C | LVFX | CPFX | MFLX |
|---|---|---|---|---|---|---|
| E. coli NIHJ | 0.006 | 0.012 | 0.012 | 0.012 | ≦0.003 | 0.006 |
| S. flexneri 2A 5503 | 0.006 | 0.012 | 0.025 | 0.025 | 0.006 | 0.012 |
| P. Vulgalis 08601 | 0.006 | 0.006 | 0.05 | 0.012 | ≦0.003 | 0.025 |
| K. pneumoniae TYPE I | 0.05 | 0.05 | 0.05 | 0.1 | 0.025 | 0.05 |
| S. marcescens 10100 | 0.05 | 0.05 | 0.2 | 0.1 | 0.025 | 0.1 |
| P. aeruginosa 32104 | 0.1 | 0.1 | 0.39 | 0.2 | 0.05 | 0.39 |
| P. aeruginosa 32121 | 0.05 | 0.025 | 0.2 | 0.1 | 0.025 | 0.2 |
| S. maltophilia IID 1275 | 0.1 | 0.39 | 0.2 | 0.39 | 0.78 | 0.1 |
| S. aureus FDA 209P | 0.012 | 0.012 | 0.025 | 0.2 | 0.1 | 0.025 |
| S. epidermidis 56500 | 0.05 | 0.1 | 0.1 | 0.39 | 0.2 | 0.1 |
| S. pyogenes G-36 | 0.05 | 0.1 | 0.2 | 0.78 | 1.56 | 0.2 |
| E. faevcalis ATCC 19433 | 0.1 | 0.2 | 0.2 | 0.78 | 0.78 | 0.2 |
| S. aureus 870307 | 0.39 | 3.13 | 1.56 | >6.25 | >6.25 | 0.78 |
| S. pneumoniae J24 | 0.025 | 0.1 | 0.1 | 0.78 | 0.39 | 0.025 |

As is clear from Table 1, the compound of the present invention exhibited antibacterial activity against a broad range of both Gram-positive bacteria, including quinolone-resistant bacteria, and Gram-negative bacteria, and the activity was found to be almost comparable to that of any of the known synthetic quinolone antibacterial agents.

TEST EXAMPLE 2

Effect of Inducing Convulsion (1) Sample to be Tested and Administration

The compounds (Compound Nos. 1, 2, and 3) of the present invention and Comparative Compounds A and B were individually dissolved in 5% glucose, to thereby prepare several samples to be tested. Groups of six-week-old Slc:ddY male mice (body weight: 23.9 to 27.4 g), each group consisting of 6 mice, were employed in the test. Each of the above-prepared samples was administered intracisternally to each mouse belonging to each group at concentrations shown in Tables 2 and 3 (5 μL/mouse). During 30 minutes after administration, it was observed whether each mouse suffered convulsion or died in an individual cage. Administration was performed according to the method described by Ueda, et al. (Reference 1).

Reference 1: Ueda H, Amano H, Shiomi H, Takagi H: Comparison of the analgesic effects of various opioid peptides by a newly devised intracisternal injection technique in conscious mice. Eur J Pharmacol. 1979; 56: 265-8.

(2) Statistical Analysis

Significant difference test between groups was performed in terms of incidence of convulsion according to the Fisher's direct probability calculation method (one-sided test, level of significance: P<0.05). On the basis of percentile incidence of convulsion, $CD_{50}$ (50% concentration for inducing convulsion) and 95% confidence limit were calculated by the Probit method. The results are shown in Tables 2, 3, and 4.

TABLE 2

| Dose (μg/5 μL/mouse, i.cist.) | Effect of inducing convulsion | |
|---|---|---|
| | Compound No. 1 | Compound A |
| 0 | 0/6 | 0/6 |
| 3.125 | — | 0/6 |
| 6.25 | — | 1/6 |
| 12.5 | 0/6 | 3/6 |
| 25 | 0/6 | 5/6**,## |
| 37.5 | 0/6 | — |
| 50 | 4/6* | — |
| $CD_{50}$ | 49.2[b] | 12.7 (7.7-24.9)[a] |

Control: 5% glucose
i.cist.: Intracisternally administration
*P < 0.05,
**P < 0.01: significant difference between incidence of convulsion of test group and that of control group (calculated by the Fisher's direct probability calculation method)
P < 0.01: significant difference between incidence of convulsion of group employing Compound No. 1 and that of each of the other groups
[a] 95% confidence limit
[b] 95% confidence limit could not be analyzed
$CD_{50}$: 50% concetration for inducing convulsion
—: Not testable

TABLE 3

| Dose ($\mu$g/5 $\mu$L/mouse, i.cist.) | Effect of inducing convulsion | |
|---|---|---|
| | Compound No. 3 | Comp. Compound B |
| 0 | 0/6 | 0/6 |
| 12.5 | — | 0/6 |
| 25 | 0/6 | 3/6 |
| 50 | 1/6 | 5/6**,# |
| 75 | 4/6* | — |
| 100 | 6/6** | — |
| CD$_{50}$ | 64.5 (47.7-80.8) | 28.6 (16.8-48.5)$^{a)}$ |

TABLE 4

| Dose ($\mu$g/5 $\mu$L/mouse, i.cist.) | Effect of inducing convulsion Compound No. 2 |
|---|---|
| 0 | 0/6 |
| 5 | 0/6 |

TABLE 4-continued

| Dose ($\mu$g/5 $\mu$L/mouse, i.cist.) | Effect of inducing convulsion Compound No. 2 |
|---|---|
| 15 | 5/6 |
| 50 | 6/6 |

As is clear from Tables 2 to 4, the compound of the present invention was found to have low effect of inducing convulsion.

TEST EXAMPLE 3

Effect of Inducing Chromosomal Aberration

Preparation of Specimen

Compound Nos. 1, 2, and 3 of the present invention, and Comparable Compounds C, D, and E were individually dissolved in 0.1 mol/L NaOH, to thereby prepare six sample solutions. From each sample solution, samples to be tested having a concentration of 1, 3, 10, 30, 50, and 100 $\mu$g/mL (as reduced to free form) were prepared. As a negative control, 0.1 mol/L NaOH was employed.

Chinese hamster lung (CHL/IU) cells in logarithmic growth phase were employed. The cells were treated in a culture solution containing each sample to be tested for 24 hours. Subsequently, a chromosome specimen was prepared from the thus-treated cells. The culture solution employed was an Eagle's MEM (product of NISSUI PHARMACEUTICAL CO., LTD.) medium containing 15% fetal bovine serum (15% FBS-MEM).

Observation of Chromosomal Aberration

In each sample concentration, 100 cells during metaphase were observed, to thereby record types and numbers of the chromosomal aberration.

Statistical Analysis

Incidence of cells exhibiting chromosomal aberration was determined through analysing difference between incidence of each negative control group and incidence of each sample-treated group by $\chi^2$-test with Yates correction at a one-side significance level of 5%. The percentage of the results without gap (TA) (percentile induction of structural aberration TA %) was shown in Table 5.

Reference 1: "Atlas of chromosome aberration by chemicals" (Asakura Publishing Co., Ltd. 1998), edited by Japanese Environmental Mutagen Society•MMS study group Reference 2: Iyakusingikai No. 1604, Guideline for Genotoxicity Test

TABLE 5

| | Percentile induction of structural aberration (TA %) | | | | | |
|---|---|---|---|---|---|---|
| Concentration ($\mu$g/mL) | Compound No. 1 | Compound No. 2 | Compound No. 3 | Comp. Compound E | Comp. Compound C | Comp. Compound D |
| Negative control | 2 | 4 | 2 | 4 | 4 | 4 |
| 1 | 0 | 1 | 3 | 0 | 3 | 4 |
| 3 | 1 | 1 | 0 | 3 | 4 | 0 |
| 10 | 2 | 1 | 2 | 1 | 5 | 3 |
| 30 | 3 | 2 | 1 | 6 | 72* | 63* |
| 50 | 2 | 3 | 5 | TOX*$^1$ | 98* | 98* |
| 100 | 7 | 8 | 9 | TOX*$^1$ | TOX*$^2$ | 100* |

*Significant difference between incidence of cells exhibiting chromosomal aberration of test group and that of nagative control (calculated by $\chi^2$-test with Yates correction, p < 0.05)
*$^1$C-mitosis was observed
*$^2$No metaphase was observed Comparative Compound E: 5-amino-7-[(3S,4S)-3-amino-4-ethyl-1-pyrrolidinyl]-1-cyclopropyl-6-fluoro-1,4-dihydro-8-methyl-4-oxoquinoline-3-carboxylic acid (see Patent Document 9)

As is clear from Table 5, in the case where Compound Nos. 1, 2, and 3 of the present invention were employed, significant increase in number of the cells exhibiting chromosomal aberration was not observed at a concentration of up to 100 $\mu$g/mL. In the chromosomal aberration test, a compound causing chromosomal aberration in 10% or less cells is evaluated negative.

In the case of Comparative Compound E, significant increase in number of the cells exhibiting chromosomal aberration was not observed at a concentration of up to 30 $\mu$g/mL. However, at a concentration of 50 $\mu$g/mL or more, C-mitosis, which may be caused by inhibition of cell division, and ski-pair-like chromosomes are observed considerably, resulting in fail to be evaluated. Comparative Compounds C and D exhibited effects of inducing chromosomal aberration at a concentration of 30 $\mu$g/mL or more. Particularly, in the case of Comparative Compound C, chromosomes could not be observed at a concentration of 100 $\mu$g/mL due to its cytotoxicity.

The invention claimed is:

1. A compound of formula (I):

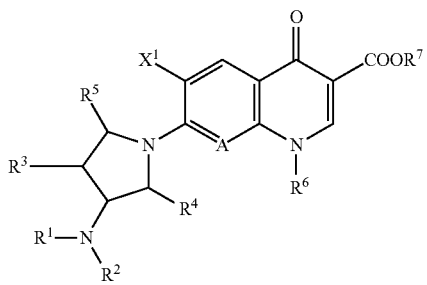

wherein
- $R^1$ represents a hydrogen atom, a $C_1$-$C_6$ alkyl group, or a substituted carbonyl group derived from an amino acid, a dipeptide, or a tripeptide;
- $R^2$ represents a hydrogen atom or a $C_1$-$C_6$ alkyl group, and, when either one or each of $R^1$ and $R^2$ is an alkyl group, the alkyl group may be substituted with a group selected from the group consisting of a hydroxyl group, an amino group, a halogen atom, a $C_1$-$C_6$ alkylthio group, and a $C_1$-$C_6$ alkoxy group;
- $R^3$ represents a $C_2$-$C_6$ alkyl group, a $C_2$-$C_6$ alkenyl group, or a $C_3$-$C_6$ cycloalkyl group;
- $R^4$ and $R^5$ each independently represents a hydrogen atom or a $C_1$-$C_6$ alkyl group;
- $R^6$ represents a $C_3$-$C_6$ halogenocycloalkyl group;
- $R^7$ represents a hydrogen atom, a phenyl group, an acetoxymethyl group, a pivaloyloxymethyl group, an ethoxycarbonyl group, a choline group, a dimethylaminoethyl group, a 5-indanyl group, a phthalidyl group, a 5-alkyl-2-oxo-1,3-dioxol-4-ylmethyl group, a 3-acetoxy-2-oxobutyl group, a $C_1$-$C_6$ alkyl group, a $C_2$-$C_7$ alkoxymethyl group, or a phenylalkyl group formed of a $C_1$-$C_6$ alkylene group and a phenyl group;
- $X^1$ represents a hydrogen atom or a halogen atom; and
- A represents a nitrogen atom or a partial structure represented by the following formula (II):

wherein $X^2$ represents a $C_1$-$C_6$ alkyl group or a $C_1$-$C_6$ alkoxy group; a salt, or a hydrate thereof.

2. The compound as described in claim 1, a salt, or a hydrate thereof, wherein the compound of formula (I) is a compound represented by the following formula:

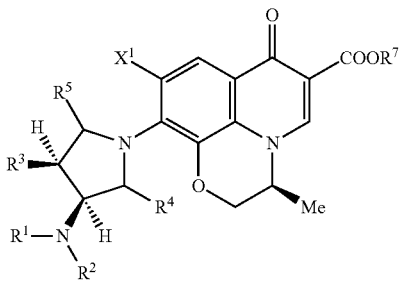

wherein
$R^1, R^2, R^3, R^4, R^5, R^6, R^7, X^1$, and A are as defined in claim 1.

3. The compound as described in claim 1, a salt, or a hydrate thereof, wherein each of $R^1$ and $R^2$ in formula (I) is a hydrogen atom.

4. The compound as described in claim 1, a salt, or a hydrate thereof, wherein one of $R^1$ and $R^2$ in formula (I) is a hydrogen atom, and the other is a methyl group.

5. The compound as described in claim 1, a salt, or a hydrate thereof, wherein $R^3$ in formula (I) is an ethyl group, an n-propyl group, a vinyl group, an isopropyl group, or a cyclopropyl group.

6. The compound as described in claim 1, a salt, or a hydrate thereof, wherein $R^3$ in formula (I) is an ethyl group.

7. The compound as described in claim 1, a salt, or a hydrate thereof, wherein each of $R^4$ and $R^5$ in formula (I) is a hydrogen atom.

8. The compound as described in claim 1, a salt, or a hydrate thereof, wherein $X^1$ in formula (I) is a fluorine atom.

9. The compound as described in claim 1, a salt, or a hydrate thereof, wherein $R^7$ in formula (I) is a hydrogen atom.

10. The compound as described in claim 1, a salt, or a hydrate thereof, wherein A in formula (I) is a C-methyl group or a C-methoxy group.

11. The compound as described in claim 1, a salt, or a hydrate thereof, wherein $R^6$ in formula (I) is a 1,2-cis-2-halogenocyclopropyl group.

12. The compound as described in claim 1, a salt, or a hydrate thereof, wherein $R^6$ in formula (I) is a stereochemically single 1,2-cis-2-halogenocyclopropyl group.

13. The compound as described claim 1, a salt, or a hydrate thereof, wherein $R^6$ in formula (I) is a (1R,2S)-2-fluorocyclopropyl group.

14. The compound as described in claim 1, a salt, or a hydrate thereof, wherein a compound of formula (I) is a stereochemically single compound.

15. 7-[(3S,4S)-3-Amino-4-ethylpyrrolidine-1-yl]-6-fluoro-1-[(1R,2S)-2-fluorocyclopropyl]-1,4-dihydro-8-methoxy-4-oxoquinoline-3-carboxylic acid, a salt, or a hydrate thereof.

16. 7-[(3S,4S)-3-Amino-4-ethylpyrrolidine-1-yl]-6-fluoro-1-[(1R,2S)-2-fluorocyclopropyl]-1,4-dihydro-8-methyl-4-oxoquinoline-3-carboxylic acid, a salt, or a hydrate theroef.

17. A drug containing, as an active ingredient, the compound as recited in claim 1, a salt, or a hydrate thereof.

18. An antibacterial drug containing, as an active ingredient, the compound as recited in claim 1, a salt, or a hydrate thereof.

19. An infectious disease treating drug containing, as an active ingredient, the compound as recited in claim 1, a salt, or a hydrate thereof.

* * * * *

UNITED STATES PATENT AND TRADEMARK OFFICE
CERTIFICATE OF CORRECTION

PATENT NO. : 7,977,327 B2
APPLICATION NO. : 11/596318
DATED : July 12, 2011
INVENTOR(S) : Hisashi Takahashi et al.

It is certified that error appears in the above-identified patent and that said Letters Patent is hereby corrected as shown below:

IN THE CLAIMS:

Column 65, lines 51-65, and Column 66, lines 1-3, (claim 2) should read:

-- 2. The compound as described in claim 1, a salt, or a hydrate thereof, wherein the compound of formula (I) is a compound represented by the following formula:

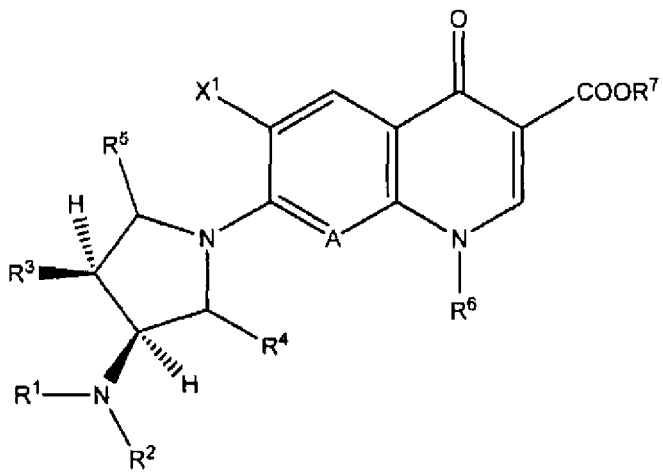

wherein
$R^1$, $R^2$, $R^3$, $R^4$, $R^5$, $R^6$, $R^7$, $X^1$ and A are as defined in claim 1. --

Signed and Sealed this
Twenty-fourth Day of April, 2012

David J. Kappos
*Director of the United States Patent and Trademark Office*